(12) United States Patent
Wilson et al.

(10) Patent No.: US 10,138,295 B2
(45) Date of Patent: Nov. 27, 2018

(54) COMPOSITIONS COMPRISING AAV EXPRESSING DUAL ANTIBODY CONSTRUCTS AND USES THEREOF

(71) Applicant: The Trustees of the University of Pennsylvania, Philadelphia, PA (US)

(72) Inventors: James M. Wilson, Philadelphia, PA (US); Anna Tretiakova, Woburn, MA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/310,555

(22) PCT Filed: May 13, 2015

(86) PCT No.: PCT/US2015/030533
§ 371 (c)(1),
(2) Date: Nov. 11, 2016

(87) PCT Pub. No.: WO2015/175639
PCT Pub. Date: Nov. 19, 2015

(65) Prior Publication Data
US 2017/0081392 A1 Mar. 23, 2017

Related U.S. Application Data
(60) Provisional application No. 61/992,649, filed on May 13, 2014.

(51) Int. Cl.
| | |
|---|---|
| A61K 48/00 | (2006.01) |
| C12N 7/00 | (2006.01) |
| C12Q 1/68 | (2018.01) |
| A61K 38/00 | (2006.01) |
| C07K 16/00 | (2006.01) |
| C07K 16/10 | (2006.01) |
| C12N 15/86 | (2006.01) |
| A61K 39/00 | (2006.01) |

(52) U.S. Cl.
CPC ...... *C07K 16/1018* (2013.01); *A61K 48/0008* (2013.01); *C12N 7/00* (2013.01); *C12N 15/86* (2013.01); *A61K 2039/507* (2013.01); *C07K 2317/14* (2013.01); *C07K 2317/31* (2013.01); *C07K 2317/51* (2013.01); *C07K 2317/515* (2013.01); *C07K 2317/52* (2013.01); *C07K 2317/622* (2013.01); *C12N 2750/14121* (2013.01); *C12N 2750/14143* (2013.01); *C12N 2830/205* (2013.01); *C12N 2830/30* (2013.01); *C12N 2830/50* (2013.01); *C12N 2840/203* (2013.01)

(58) Field of Classification Search
CPC ............ A61K 48/00; A61K 38/00; C12N 2750/14143; A01K 2217/075; C07K 14/4703

See application file for complete search history.

(56) References Cited

U.S. PATENT DOCUMENTS

| | | |
|---|---|---|
| 5,139,941 A | 8/1992 | Muzyczka et al. |
| 5,741,683 A | 4/1998 | Zhou et al. |
| 5,811,524 A | 9/1998 | Brams et al. |
| 5,891,994 A | 4/1999 | Goldstein |
| 5,972,596 A | 10/1999 | Pavlakis et al. |
| 6,057,152 A | 5/2000 | Samulski et al. |
| 6,193,981 B1 | 2/2001 | Goldstein |
| 6,204,059 B1 | 3/2001 | Samulski et al. |
| 6,268,213 B1 | 7/2001 | Samulski et al. |
| 6,491,907 B1 | 12/2002 | Rabinowitz et al. |
| 6,596,535 B1 | 7/2003 | Carter |
| 6,660,514 B1 | 12/2003 | Zolotukhin et al. |
| 6,780,639 B1 * | 8/2004 | Chtarto ............... A61K 38/185 424/93.21 |
| 6,951,753 B2 | 10/2005 | Shenk et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,442,373 B2 | 10/2008 | Morrow et al. |
| 7,465,583 B2 | 12/2008 | Samulski et al. |

(Continued)

FOREIGN PATENT DOCUMENTS

| | | |
|---|---|---|
| WO | WO-1999/016884 | 4/1999 |
| WO | WO-2001/054719 | 8/2001 |

(Continued)

OTHER PUBLICATIONS

Grieger et al. "Packaging capacity of adeno-associated virus serotypes: impact of larger genomes on infectivity and postentry steps." Journal of virology 79.15 (2005): 9933-9944. (Aug. 2005).

(Continued)

*Primary Examiner* — Barry A Chestnut
(74) *Attorney, Agent, or Firm* — Howson and Howson LLP

(57) ABSTRACT

A recombinant adeno-associated virus (AAV) having an AAV capsid and packaged therein a heterologous nucleic acid which expresses two functional antibody constructs in a cell is described. Also described are antibodies comprising a heavy chain and a light chain from a heterologous antibody. In one embodiment, the antibodies are co-expressed from a vector containing: a first expression cassette which encodes at least a first open reading frame (ORF) for a first immunoglobulin under the control of regulatory control sequences which direct expression thereof; and a second expression cassette which comprises a second ORF, a linker, and a third ORF under the control of regulatory control sequences which direct expression thereof, wherein the second and third ORF encode for a second and third immunoglobulin construct. The vector co-expressing these two antibody constructs is in one embodiment an AAV, in which the 5' and 3' ITRs flank the expression cassettes and regulatory sequences.

21 Claims, 8 Drawing Sheets

Specification includes a Sequence Listing.

(56) References Cited

U.S. PATENT DOCUMENTS

| | | | |
|---|---|---|---|
| 7,588,772 | B2 | 9/2009 | Kay et al. |
| 7,790,449 | B2 | 9/2010 | Gao et al. |
| 7,906,111 | B2 | 3/2011 | Wilson et al. |
| 8,187,601 | B2 | 5/2012 | Weng et al. |
| 9,198,984 | B2 | 12/2015 | Lock et al. |
| 2006/0136184 | A1 | 6/2006 | Gustafsson et al. |
| 2011/0065779 | A1 | 3/2011 | Fang et al. |
| 2011/0076265 | A1 | 3/2011 | Burioni et al. |
| 2011/0236353 | A1 | 9/2011 | Wilson et al. |
| 2012/0232133 | A1* | 9/2012 | Balazs ............... C07K 16/1045 514/44 R |
| 2012/0282695 | A1 | 11/2012 | Blain et al. |
| 2014/0032186 | A1 | 1/2014 | Gustafsson et al. |
| 2014/0037637 | A1* | 2/2014 | McNally ............... C07K 16/26 424/139.1 |
| 2014/0065666 | A1 | 3/2014 | Simpson et al. |
| 2014/0094392 | A1 | 4/2014 | Bowers et al. |
| 2014/0127749 | A1 | 5/2014 | Mason et al. |

FOREIGN PATENT DOCUMENTS

| | | | |
|---|---|---|---|
| WO | WO-2003/042397 | | 5/2003 |
| WO | WO-2004/009618 | A2 | 1/2004 |
| WO | WO-2005/033321 | | 4/2005 |
| WO | WO-2006/110689 | | 10/2006 |
| WO | WO-2008/156763 | | 12/2008 |
| WO | WO-2009/115972 | | 9/2009 |
| WO | WO-2010/010466 | | 1/2010 |
| WO | WO-2010/111367 | A1 | 9/2010 |
| WO | WO-2010/130636 | | 11/2010 |
| WO | WO-2010/140114 | | 12/2010 |
| WO | WO-2010/151673 | A1 | 12/2010 |
| WO | WO2010151673 | * | 12/2010 |
| WO | WO-2010/119991 | A3 | 1/2011 |
| WO | WO-2011/126868 | | 10/2011 |
| WO | WO-2011/143318 | A2 | 11/2011 |
| WO | WO-2011/160119 | A2 | 12/2011 |
| WO | WO-2012/020006 | A2 | 2/2012 |
| WO | WO-2012/125124 | A1 | 9/2012 |
| WO | WO-2012/138975 | A1 | 10/2012 |
| WO | WO-2012/145572 | A1 | 10/2012 |
| WO | WO-2013/046704 | | 4/2013 |
| WO | WO-2013/049492 | | 4/2013 |
| WO | WO-2013/059206 | A2 | 4/2013 |
| WO | WO-2013/076186 | | 5/2013 |
| WO | WO-2013/155222 | | 10/2013 |
| WO | WO-2013/163427 | A1 | 10/2013 |
| WO | WO-2015/012924 | | 1/2015 |
| WO | WO-2015/142661 | A1 | 9/2015 |
| WO | WO-2015/175639 | A1 | 11/2015 |

OTHER PUBLICATIONS

Grieger et al. "Separate basic region motifs within the adeno-associated virus capsid proteins are essential for infectivity and assembly." Journal of virology 80.11 (2006): 5199-5210. (Jun. 2006).

Grieger et al. "Adeno-associated virus as a gene therapy vector: Vector development, production and clinical applications," Adv. Biochem. Engin/Biotechnol. 99: 119-145 (Oct. 2005).

Alexander et al., "Insulin stimulates glyceraldehyde-3-phosphate dehydrogenase gene expression through cis-acting DNA sequences." Proceedings of the National Academy of Sciences 85.14 (1988): 5092-5096. (Jul. 1988).

Amara et al, "Control of a mucosal challenge and prevention of AIDS by a multiprotein DNA/MVA vaccine." Science 292.5514 (2001): 69-74. (Apr. 6, 2001).

An et al, "Active retrotransposition by a synthetic L1 element in mice." Proceedings of the National Academy of Sciences 103.49 (2006): 18662-18667. (Epub Nov. 21, 2006.).

Andersson et al, "An atlas of active enhancers across human cell types and tissues." Nature 507.7493 (2014): 455-461. (Published online Mar. 26, 2014).

Barouch et al, "Elicitation of high-frequency cytotoxic T-lymphocyte responses against both dominant and subdominant simian-human immunodeficiency virus epitopes by DNA vaccination of rhesus monkeys." Journal of virology 75.5 (2001): 2462-2467. (Mar. 2001).

Brinster et al. "Regulation of metallothionein-thymidine kinase fusion plasmids injected into mouse eggs." (1982): 39-42. (Mar. 4, 1982).

Buning et al., 2008, "Recent developments in adeno-associated virus vector technology," J. Gene Med. 10:717-733 (Jul. 2008).

Ercolani et al., "Isolation and complete sequence of a functional human glyceraldehyde-3-phosphate dehydrogenase gene." Journal of Biological Chemistry 263.30 (1988): 15335-15341. (Oct. 25, 1988).

Gossen et al, "Tight control of gene expression in mammalian cells by tetracycline-responsive promoters." Proceedings of the National Academy of Sciences 89.12 (1992): 5547-5551. (Jun. 1992).

Lai Chng et al., "Antisense RNA complementary to 3'coding and noncoding sequences of creatine kinase is a potent inhibitor of translation in vivo." Proceedings of the National Academy of Sciences 86.24 (1989): 10006-10010. (Dec. 1989).

Levitt et al, "Definition of an efficient synthetic poly (A) site." Genes & Development 3.7 (1989): 1019-1025. (Jul. 1989).

Mayo et al. "The mouse metallothionein-I gene is transcriptionally regulated by cadmium following transfection into human or mouse cells." Cell 29.1 (1982): 99-108.

McCarty et al, "Self-complementary recombinant adeno-associated virus (scAAV) vectors promote efficient transduction independently of DNA synthesis", Gene Therapy, Aug. 2001, vol. 8, No. 16, pp. 1248-1254 (Aug. 2001).

Medicines in Development Biologics, 2013 Report, pp. 1-87, a publication of PhRMA's Communications & Public Affairs Department. (202) 835-3460 (Feb. 7, 2013).

Ng et al. "Regulation of the human β-actin promoter by upstream and intron domains." Nucleic acids research 17.2 (1989): 601-615. (Jan. 25, 1989).

Quitschke et al, "The beta actin promoter. High levels of transcription depend upon a CCAAT binding factor." Journal of Biological Chemistry 264.16 (1989): 9539-9546. (Jun. 5, 1989).

Radcliffe et al, "Multiple gene products from a single vector:'self-cleaving'2A peptides." Gene Therapy 11.23 (2004): 1673-1673.

Sawada-Hirai et al, "Human anti-anthrax protective antigen neutralizing monoclonal antibodies derived from donors vaccinated with anthrax vaccine adsorbed." Journal of immune based therapies and vaccines 2.1 (2004): 5 . . . (on-line May 12, 2004).

Scharfmann et al., "Long-term in vivo expression of retrovirus-mediated gene transfer in mouse fibroblast implants." Proceedings of the National Academy of Sciences 88.11 (1991): 4626-4630. (Jun. 1, 1991).

Searle et al. "Building a metal-responsive promoter with synthetic regulatory elements." Molecular and Cellular Biology 5.6 (1985): 1480-1489. (Jun. 1985).

Sui et al, "Structural and functional bases for broad-spectrum neutralization of avian and human influenza A viruses." Nature structural & molecular biology 16.3 (2009): 265-273. (Mar. 2009).

Thomson et al, Nucl. Acids. Res., "A comprehensive comparison of multiple sequence alignments", 27(13):2682-2690 (1999). (Jul. 1, 1999).

Xia et al, "siRNA-mediated gene silencing in vitro and in vivo." Nature biotechnology 20.10 (2002): 1006-1010. Epub Sep. 16, 2002.

Zhang et al., 2009, "Adenovirus-adeno-associated virus hybrid for large-scale recombinant adeno-associated virus production," Human Gene Therapy 20:922-929 (Jul. 20, 2009).

International Search Report and Written Opinion of the International Searching Authority /U.S. issued on PCT/US2015/030533 dated Aug. 14, 2015.

Drug Information of Pertuzumab (Accession No. DB06366) retrieved from: https://www.drugbank.ca/drugs/DB06366 on Jan. 25, 2017.

Drug Information of Trastuzumab (Accession No. DB00072 (BTD00098, BIOD00098)) retrieved from: https://www.drugbank.ca/drugs/DB00072 on Jan. 25, 2017.

(56) References Cited

OTHER PUBLICATIONS

Choi et al. AAV hybrid serotypes: improved vectors for gene delivery. Curr Gene Ther. Jun. 2005;5(3):299-310. (Jun. 2005).
Extended European Search Report issued in the corresponding European Patent Application No. 15792528.0 dated Sep. 20, 2017.
Communication pursuant to Rules 70(2) and 70a(2) EPC issued in the corresponding European Patent Application No. 15792528.0 dated Oct. 9, 2017.
Lewis, AD, et al. Generation of Neutralizing Activity against Human Immunodeficiency Virus Type 1 in Serum by Antibody Gene Transfer, J Virol. Sep. 2002;76(17):8769-75.
Office Action issued in the counterpart Colombian Patent Application No. NC2016/0005185, dated Mar. 21, 2018, with unofficial translation.
Office Action issued in the counterpart Mexican Patent Application No. MX/a/2016/014813, dated Mar. 9, 2018, with unofficial translation.
Office Action issued in the corresponding Chilean Patent Application No. 2016-02840 dated Nov. 24, 2017 and Correspondence from Chilean agent with English translation, with confidential information redacted.
Office Action issued in the corresponding Panamanian Patent Application No. 91414 dated Nov. 24, 2017.

\* cited by examiner

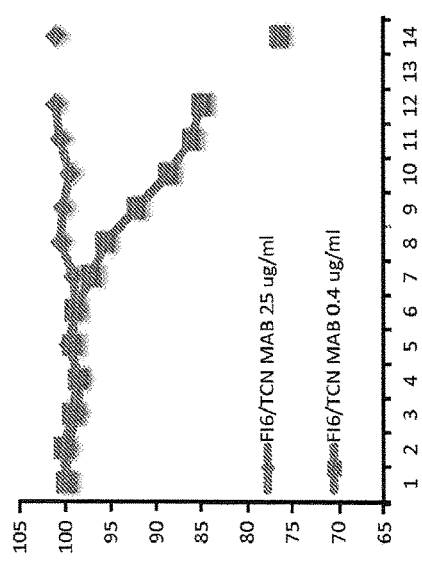
FIG 8A
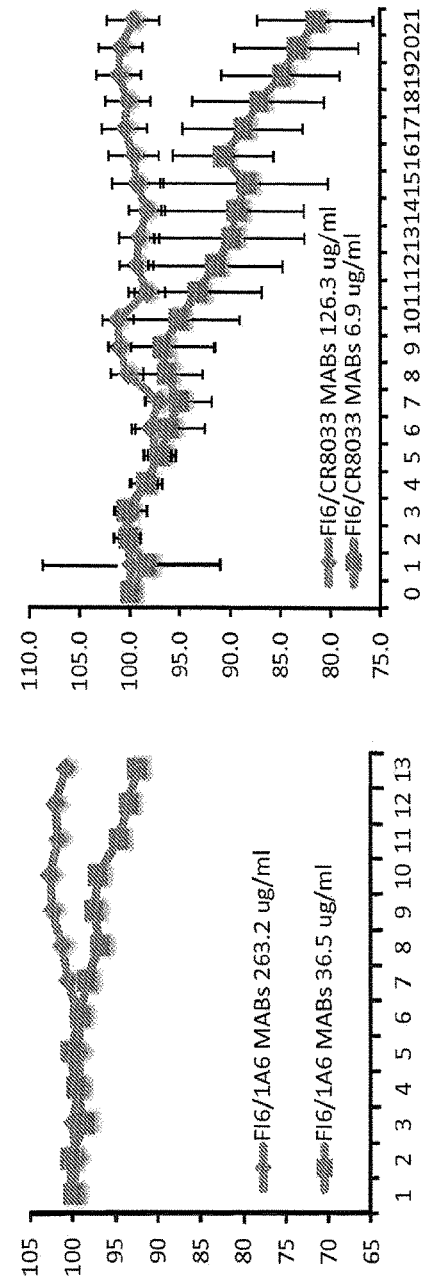
FIG 8B
FIG 8C

US 10,138,295 B2

COMPOSITIONS COMPRISING AAV EXPRESSING DUAL ANTIBODY CONSTRUCTS AND USES THEREOF

CROSS-REFERENCE TO RELATED APPLICATIONS

This is a 371 national stage of PCT/US2015/030533, filed May 13, 2015, which claims the benefit under 35 USC 119(e) of U.S. Provisional Patent Application No. 61/992,649, filed May 13, 2014.

STATEMENT REGARDING FEDERALLY SPONSORED RESEARCH OR DEVELOPMENT

This invention was made with government support under grant number ARO No. 64047- LS-DRP awarded by Defense Advanced Research Projects Agency (DARPA). The government has certain rights in the invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "14-7032PCT_Seq Listing_ST25.txt".

BACKGROUND OF THE INVENTION

Monoclonal antibodies have been proven as effective therapeutics for cancer and other diseases. Current antibody therapy often involves repeat administration and long term treatment regimens, which are associated with a number of disadvantages, such as inconsistent serum levels and limited duration of efficacy per administration such that frequent re-administration is required and high cost. The use of antibodies as diagnostic tools and therapeutic modalities has found increasing use in recent years. The first FDA-approved monoclonal antibody for cancer treatment, Rituxan® (Rituximab) was approved in 1997 for the treatment of patients with non-Hodgkin's lymphoma and soon thereafter in 1995, Herceptin®, a humanized monoclonal antibody for treatment of patients with metastatic breast cancer, was approved. Numerous antibody-based therapies that are in various stages of clinical development are showing promise. Given the success of various monoclonal antibody therapies, it has been suggested the next generation of biopharmaceuticals will involve cocktails, i.e., mixtures, of antibodies.

One limitation to the widespread clinical application of antibody technology is that typically large amounts of antibody are required for therapeutic efficacy and the costs associated with production are significant. Chinese Hamster Ovarian (CHO) cells, SP20 and NSO2 myeloma cells are the most commonly used mammalian cell lines for commercial scale production of glycosylated human proteins such as antibodies. The yields obtained from mammalian cell line production typically range from 50-250 mg/L for 5-7 day culture in a batch fermenter or 300-1000 mg/L in 7-12 days in fed batch fermenters.

Adeno associated virus (AAV) is a desirable vector for delivering therapeutic genes due to its safety profile and capability of long term gene expression in vivo. Recombinant AAV vectors (rAAV) have been previously used to express single chain and full length antibodies in vivo. Due to the limited transgene packaging capacity of AAV, it has been a technical challenge to have a tightly regulated system to express heavy and light chains of an antibody using a single AAV vector in order to generate full length antibodies.

There remains a need in the art for delivering two antibodies in a single composition for therapeutic use.

SUMMARY OF THE INVENTION

A recombinant adeno-associated virus (AAV) having an AAV capsid which has packaged therein a heterologous nucleic acid which expresses two functional antibodies in a cell is provided herein. In one embodiment, the recombinant AAV contains an ORF encoding an immunoglobulin light chain, a second ORF encoding a first immunoglobulin heavy chain and a third ORF encoding a second heavy chain, whereby the expressed functional antibody constructs have two different heavy chains with different specificities which share a light chain. In one embodiment, the two antibodies with different specificities are co-expressed, with a third, bispecific antibody having the specificities of the two monospecific antibodies.

In one embodiment, the rAAV comprises: a 5' AAV inverted terminal repeat (ITR); a first expression cassette which encodes at least a first open reading frame (ORF) for a first immunoglobulin under the control of regulatory control sequences which direct expression thereof; a second expression cassette which comprises a second ORF, a linker, and a third ORF under the control of regulatory control sequences which direct expression thereof, wherein the second and third ORF encode for a second and third immunoglobulin construct; and a 3' AAV ITR.

A pharmaceutical composition is provided which comprises a recombinant AAV which expresses at least two functional antibody constructs and pharmaceutically acceptable carrier. In one embodiment, the at least two functional antibodies have different specificities. Optionally, also co-expressed is a bispecific antibody.

A composition comprising at least two functional antibodies having different specificities is provided, wherein each of the antibodies has the same light chain and a different heavy chain. The light chain is from a different source than the heavy chain for one or both of the antibodies. In one embodiment, two functional monospecific antibodies and a bifunctional antibody are expressed. In one embodiment, the ratio of antibodies is about 25:about 50:about 25, homodimeric:bispecific:homodimeric.

A method of delivering two functional antibodies to a subject is provided which comprises administering a recombinant AAV to the subject.

Still other aspects and advantages of the invention will be readily apparent from the following detailed description of the invention.

BRIEF DESCRIPTION OF THE DRAWINGS

FIG. 4A is a bar chart showing binding to protein A captures total monoclonal antibody in the mixture (negative control is represented by the bar on the left, antibody mixture by the bar on the right). FIG. 4B is a graph showing that binding to the TSG101 peptide captures only the MAB containing 1A6 heavy chain (upper line). These data demonstrate that when co-expressed with FI6v3k2, 1A6 antibody retained the binding specificity of antibody from which its heavy chains originated.

FIG. 6A is a line graph showing percent change in weight. The circle represents the AAV9 construct with a bidirectional promoter expressing synthetic FI6v3 and CR8033 monoclonal antibodies having the same heterologous light chain. The square represents a positive control, i.e., AAV9 expressing a single antibody type FI6 also delivered at $1 \times 10^{11}$ GC, and the triangle represents naïve animals. FIG. 6B shows survival post-challenge.

FIG. 7A is a line graph showing percent change in weight. The circle represents the AAV9 construct with a bidirectional promoter expressing synthetic FI6 and CR8033 monoclonal antibodies having the same heterologous light chain. The square represents a positive control, i.e., AAV9 expressing a single antibody type CR8033 also delivered at $1 \times 10^{11}$ GC, and the triangle represents naïve animals. FIG. 7B shows survival post-challenge.

FIG. 8A is a chart showing protection in a mouse model following administration of an AAV which expresses both FI6v3 and TCN monoclonal antibodies, as expressed by weight of the mouse over days. The top line (diamonds) represents a dose of 25 micrograms (μg/mL) and the bottom line represents 0.4 μg/mL.

FIG. 8B is a chart showing protection in a mouse model following administration of an AAV which expresses both FI6v3 and IA6 monoclonal antibodies, as expressed by weight of the mouse over days. The top line (diamonds) represents a dose of 263.2 micrograms (μg/mL) and the bottom line represents 36.5 μg/mL.

FIG. 8C is a chart showing protection in a mouse model following administration of an AAV which expresses both FI6v3 and CR8033 monoclonal antibodies, as expressed by weight of the mouse over days. The top line (diamonds) represents a dose of 126.3 micrograms (μg/mL) and the bottom line represents 6.9 μg/mL.

DETAILED DESCRIPTION OF THE INVENTION

Figure 1A:
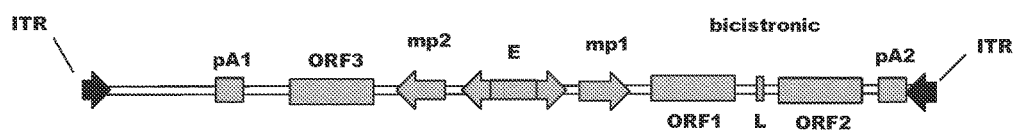
FIG. 1A is a cartoon illustrating an exemplary arrangement for a vector expressing two monospecific antibody constructs containing a first and a second heavy chain and a light chain, which may be from an antibody heterologous to one or both of the antibodies from which the first and second heavy chain originate, and a third, bispecific antibody. This arrangement utilizes a shared enhancer which is bidirectional and which separates a first expression cassette and a second expression cassette. Three open reading frames (ORF) are illustrated. L refers to a linker. pA1 refers to a first polyA and pA2 refers to a second polyA. MP1 refers to a first minimal promoter and MP2 refers to a second minimal promoter. The polyA and the MP may be the same or different for each expression cassette.

A vector is provided herein which delivers at least two functional antibodies by co-expressing two different heavy chains and single light chain which when expressed in a cell form two functional antibodies with different specificities, i.e., which recognize different antigens (or ligands). A third functional antibody may also be expressed and is bispecific, having the heavy chain of each of the two monospecific antibodies. Typically, the third antibody is expressed at a lower level than the two monospecific antibodies. A vector may be used in vivo for efficient production of compositions which will utilize the at least two antibodies or an antibody-producing host cell may be engineered to contain the expression cassettes for the two, different heavy chains and a single type of light chain. Thus, the invention also encompasses a host cell expressing a mixture of two monospecific antibodies, wherein each antibody has a distinct specificity but contains the same light chain, and a third antibody which is bispecific. In one desired embodiment, the vector is designed to deliver the three different antibody constructs in a subject to which the vector is administered.

In one embodiment, the vector is a recombinant AAV which has packaged within an AAV capsid a nucleic acid molecule containing sequences encoding two different heavy chains and a single light chain, which when co-expressed forms two functional monospecific antibodies, i.e., first antibody with a first heavy chain and the light chain and a second antibody with the second heavy chain and the light chain, and a third antibody that has one of each of the heavy chains and the same light chain to make a bispecific antibody.

A "functional antibody" may be an antibody or immunoglobulin which binds to a selected target (e.g., an antigen on a cancer cell or a pathogen, such as a virus, bacteria, or parasite) with sufficient binding affinity to effect a desired physiologic result, which may be protective (e.g., passive immunization) or therapeutic.

The AAV vector provided herein may contain 1, 2, or 3 open reading frames (ORF) for up to ten immunoglobulin domains. As used herein, an "immunoglobulin domain" refers to a domain of an antibody heavy chain or light chain as defined with reference to a conventional, full-length antibody. More particularly, a full-length antibody contains a heavy (H) chain polypeptide which contains four domains: one N-terminal variable (VH) region and three C-terminal constant (CH1, CH2 and CH3) regions and a light (L) chain polypeptide which contains two domains: one N-terminal variable (VL) region and one C-terminal constant (CL) region. An Fc region contains two domains (CH2-CH3). A Fab region may contain one constant and one variable domain for each the heavy and light chains.

In an AAV vector described herein, two full-length heavy chain polypeptides may be expressed (4 domains each) and a light chain polypeptide (two domains). In one desirable embodiment, the two heavy chain polypeptides have different specificities, i.e., are directed to different targets. Thus, the vectors are useful alone or in combination, for expressing mixtures of antibodies.

As used herein, "different specificities" indicates that the referenced immunoglobulin constructs (e.g., a full-length antibody, a heavy chain, or other construct capable of binding a specific target) bind to a different target site. Suitably, in a dual expressed antibody construct, the two specificities are non-overlapping and/or non-interfering, and may optionally enhance each other. Two antibody (immunoglobulin) constructs as described herein confer different specificity by binding to a different target site on the same pathogen or target site (e.g., a virus protein or tumor). Such different target antigens may be different strains of the same viral type (e.g., two different influenza strains), or two different antigens (e.g., an antiviral and anti-cancer, two different anti-cancer constructs, amongst others). For example, a first heavy chain polypeptide may combine with the light chain to form an antibody construct having a first specificity, the second heavy chain polypeptide may combine with the light chain to form a second antibody construct having a second specificity, and the first and second heavy chain may combine with the light chain to form a bispecific antibody. The antibodies may optionally both be directed to different antigenic sites (epitopes) on a single target (e.g., different target sites on a selected viral, bacterial, fungal or parasite pathogen) or to different targets. For example, heavy chains from the two antibodies may be directed to the influenza virus, and may be co-expressed to form two monospecific antibodies (e.g., heavy chains from influenza viruses FI6, CR8033 and C05 may be selected) and expressed with a selected light chain, and a bispecific antibody. Examples of suitable influenza antibody and other anti-airborne pathogen antibody constructs and a method for delivering same are described in, e.g., WO 2012/145572A1. The antibodies may also be directed to different targets (e.g., an anti-viral antibody, including chronic viral infections, viral infections associated with cancers, or different anti-neoplastic cell surface proteins or other targets). Examples of suitable viral targets include the influenza hemagglutinin protein or other viral proteins, human immunodeficiency virus (HIV), human papilloma virus (HPV), Epstein-Barr virus, human herpes virus, respiratory syncytial virus, amongst others. Thus, the invention is particularly well suited for use in therapeutics and passive prophylaxis for which combinations of antibodies are desired.

The term "immunoglobulin" is used herein to include antibodies, and functional fragments thereof. Antibodies may exist in a variety of forms including, for example, polyclonal antibodies, monoclonal antibodies, camelized single domain antibodies, intracellular antibodies ("intrabodies"), recombinant antibodies, multispecific antibody (bispecific), antibody fragments, such as, Fv, Fab, F(ab)$_2$, F(ab)$_3$, Fab', Fab'-SH, F(ab')$_2$, single chain variable fragment antibodies (scFv), tandem/bis-scFv, Fc, pFc', scFvFc (or scFv-Fc), disulfide Fv (dsfv), bispecific antibodies (bc-scFv) such as BiTE antibodies; camelid antibodies, resurfaced antibodies, humanized antibodies, fully human antibodies, single-domain antibody (sdAb, also known as NANOBODY®), chimeric antibodies, chimeric antibodies comprising at least one human constant region, and the like. "Antibody fragment" refers to at least a portion of the variable region of the immunoglobulin that binds to its target, e.g., the tumor cell. In one embodiment, immunoglobulin is an IgG. However, other types of immunoglobulin may be selected. In another embodiment, the IgG subtype selected is an IgG1. However, other isotypes may be selected. Further, any of the IgG1 allotypes may be selected.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous. The term "heterologous light chain" is a light chain containing a variable domain and/or constant domain from an antibody which has a different target specificity from the specificity of the heavy chain.

The two or more ORF(s) carried by the nucleic acid molecule packaged within the vector may be expressed from two expression cassettes, one or both of which may be bicistronic. Because the expression cassettes contain heavy chains from two different antibodies, it is desirable to introduce sequence variation between the two heavy chain sequences to minimize the possibility of homologous recombination. Typically there is sufficient variation between the variable domains of the two antibodies (VH-Ab1 and VH-Ab2). However, it is desirable to ensure there is sufficient coding sequence variation between the constant regions of the first antibody (Ab1) and the second antibody (Ab2), most preferably in each of the CH1, CH2, and CH3 regions. For example, in one embodiment, the heavy chain constant regions of a first antibody may have the sequence of nt 1 to 705 of SEQ ID NO: 1 (which encodes amino acids 1-233 of SEQ ID NO:2) or a sequence which is about 95% to about 99% identical thereto without any introducing any amino acid changes. In one embodiment, variation in the sequence of these regions is introduced in the form of synonymous codons (i.e., variations of the nucleic acid sequence are introduced without any changes at the amino acid level). For example, the second heavy chain may have constant regions which are at least 15%, at least about 25%, at least about 35%, divergent (i.e., about 65% to about 85% identical) over CH1, CH2 and/or CH3.

Once the target and immunoglobulin are selected, the coding sequences for the selected immunoglobulin (e.g., heavy and/or light chain(s)) may be obtained and/or synthesized. Methods for sequencing a nucleic acid (e.g., RNA and DNA) are known to those of skill in the art. Once the sequence of a nucleic acid is known, the amino acid can be deduced and subsequently, there are web-based and commercially available computer programs, as well as service based companies which back translate the amino acids sequences to nucleic acid coding sequences. See, e.g., backtranseq by EMBOSS, www.ebi.ac.uk/Tools/st/; Gene Infinity www.geneinfinity.org/sms/sms_backtranslation.html);

ExPasy www.expasy.org/tools/). In one embodiment, the RNA and/or cDNA coding sequences are designed for optimal expression in human cells. Methods for synthesizing nucleic acids are known to those of skill in the art and may be utilized for all, or portions, of the nucleic acid constructs described herein.

Codon-optimized coding regions can be designed by various different methods. This optimization may be performed using methods which are available on-line (e.g., GeneArt,), published methods, or a company which provides codon optimizing services, e.g., as DNA2.0 (Menlo Park, Calif.). One codon optimizing algorithm is described, e.g., in WO 2015/012924, which is incorporated by reference herein. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

Optionally, amino acid substitutions may be introduced into a heavy chain constant region in order to increase sequence diversity between the two antibody heavy chains and/or for another purpose. Methods and computer programs for preparing such alignments are available and well known to those of skill in the art. Substitutions may also be written as (amino acid identified by single letter code)-position #-(amino acid identified by single letter code) whereby the first amino acid is the substituted amino acid and the second amino acid is the substituting amino acid at the specified position. The terms "substitution" and "substitution of an amino acid" and "amino acid substitution" as used herein refer to a replacement of an amino acid in an amino acid sequence with another one, wherein the latter is different from the replaced amino acid. Methods for replacing an amino acid are well known to the skilled in the art and include, but are not limited to, mutations of the nucleotide sequence encoding the amino acid sequence. Methods of making amino acid substitutions in IgG are described, e.g., for WO 2013/046704, which is incorporated by reference for its discussion of amino acid modification techniques.

The term "amino acid substitution" and its synonyms described above are intended to encompass modification of an amino acid sequence by replacement of an amino acid with another, substituting amino acid. The substitution may be a conservative substitution. The term conservative, in referring to two amino acids, is intended to mean that the amino acids share a common property recognized by one of skill in the art. The term non-conservative, in referring to two amino acids, is intended to mean that the amino acids which have differences in at least one property recognized by one of skill in the art. For example, such properties may include amino acids having hydrophobic nonacidic side chains, amino acids having hydrophobic side chains (which may be further differentiated as acidic or nonacidic), amino acids having aliphatic hydrophobic side chains, amino acids having aromatic hydrophobic side chains, amino acids with polar neutral side chains, amino acids with electrically charged side chains, amino acids with electrically charged acidic side chains, and amino acids with electrically charged basic side chains. Both naturally occurring and non-naturally occurring amino acids are known in the art and may be used as substituting amino acids in embodiments. Thus, a conservative amino acid substitution may involve changing a first amino acid having a hydrophobic side chain with a different amino acid having a hydrophobic side chain; whereas a non-conservative amino acid substitution may involve changing a first amino acid with an acidic hydrophobic side chain with a different amino acid having a different side chain, e.g., a basic hydrophobic side chain or a hydrophilic side chain. Still other conservative or non-conservative changes can be determined by one of skill in the art. In still other embodiments, the substitution at a given position will be to an amino acid, or one of a group of amino acids, that will be apparent to one of skill in the art in order to accomplish an objective identified herein.

In order to express a selected immunoglobulin domain, a nucleic acid molecule may be designed which contains codons which have been selected for optimal expression of the immunoglobulin polypeptides in a selected mammalian species, e.g., humans. Further, the nucleic acid molecule may include a heterologous leader sequence for each heavy chain and light chain of the selected antibody, which encodes the wild-type or a mutated IL-2 signal leader peptide fused upstream of the heavy and light chain polypeptides composed of the variable and constant regions. However, another heterologous leader sequence may be substituted for one or both of the IL-2 signal peptide. Signal/leader peptides may be the same or different for each the heavy chain and light chain immunoglobulin constructs. These may be signal sequences which are natively found in an immunoglobulin (e.g., IgG), or may be from a heterologous source. Such heterologous sources may be a cytokine (e.g., IL-2, IL12, IL18, or the like), insulin, albumin, β-glucuronidase, alkaline protease or the fibronectin secretory signal peptides, amongst others.

As used herein, an "expression cassette" refers to a nucleic acid sequence which comprises at least a first open reading frame (ORF) and optionally a second ORF. An ORF may contain two, three, or four antibody domains. For example, the ORF may contain a full-length heavy chain. Alternatively, an ORF may contain one or two antibody domains. For example, the ORF may contain a heavy chain variable domain and a single heavy chain constant domain. In another example, the ORF may contain a light chain variable and a light chain constant region. Thus, an expression cassette may be designed to be bicistronic, i.e., to contain regulatory sequences which direct expression of the ORFs thereon from shared regulatory sequences. In this instance, the two ORFs are typically separated by a linker. Suitable linkers, such as an internal ribozyme binding site (IRES) and/or a furin-2a self-cleaving peptide linker (F2a), [see, e.g., Radcliffe and Mitrophanous, Gene Therapy (2004), 11, 1673-1674] are known in the art. Suitably, the ORF are operably linked to regulatory control sequences which direct expression in a target cell. Such regulatory control sequences may include a polyA, a promoter, and an enhancer. In order to facilitate co-expression from an AAV vector, at least one of the enhancer and/or polyA sequence may be shared by the first and second expression cassettes.

In one embodiment, the rAAV has packaged within the selected AAV capsid, a nucleic acid molecule comprising: a 5' ITR, a first expression cassette, a bidirectional enhancer, and a second expression cassette, where the bidirectional enhancer separates the first and second expression cassettes, and a 3' ITR. FIG. 1A is provided herein as an example of this embodiment. For example, in such an embodiment, a first promoter for a first expression cassette is located to the left of the bidirectional enhancer, followed by at least a first open reading frame, and a polyA sequence, and a second promoter. Further, a second promoter for the second expression cassette is located to the right of the bidirectional enhancer, followed by at least a second open reading frame and a polyA. The first and second promoters and the first and second polyA sequences may be the same or different. A minimal promoter and/or a minimal polyA may be selected in order to conserve space. Typically, in this embodiment, each promoter is located either adjacent (either to the left or the right (or 5' or 3')) to the enhancer sequence and the polyA sequences are located adjacent to the ITRs, with the ORFs there between. While FIG. 1A is illustrative, the order of the ORFs may be varied, as may the immunoglobulin domains encoded thereby. For example, the light chain constant and variable sequences may be located to the left of the enhancer and the two heavy chains may be encoded by ORFs located to the right of the enhancer. Alternatively, one of the heavy chains may be located to the left of the enhancer and the ORFs to the right of the enhancer encode a second heavy chain and a light chain. Alternatively, the opposite configuration is possible, and the expression cassette to the left of the enhancer may be bicistronic. Alternatively, depending upon what domains are encoded, both expression cassettes may be monocistronic (e.g., encoding two immunoadhesins), or both can be bicistronic (e.g., encoding two complete FABs).

Figure 1B:
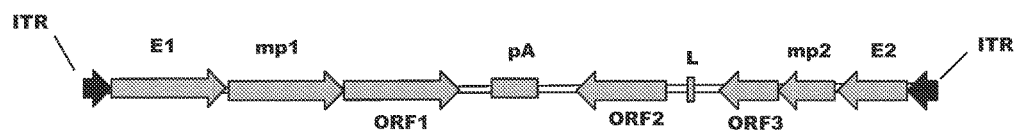
FIG. 1B is a cartoon illustrating an alternative exemplary arrangement for a vector expressing two antibody constructs containing a first and a second heavy chain and a light chain, which may be from an antibody heterologous to one or both of the antibodies from which the first and second heavy chain originate, and a third, bispecific antibody. This arrangement utilizes a shared polyA. E1 refers to a first enhancer and E2 refers to a second enhancer. These may be same or different enhancers for each of the expression cassettes. Similarly MP1 and MP2 may the same or different.

In another embodiment, the rAAV has packaged within the selected AAV capsid, a nucleic acid molecule comprising: a 5' ITR, a first expression cassette, a polyA which functions bidirectionally, and a second expression cassette, where the bidirectional polyA separates and functions for both the first and the second expression cassettes, and a 3' ITR. FIG. 1B is provided herein as an example of this embodiment. In this embodiment, a first enhancer and a first promoter (or enhancer/promoter combination) is located to the right of the 5' ITR, followed by the ORF(s) and the bidirectional polyA. The second expression cassette is separated from the first expression cassette by the bidirectional polyA and is transcribed in the opposite orientation. In this expression cassette, the enhancer and promoter (or promoter/enhancer combination) is located adjacent to the 3' ITR and the ORF(s) are adjacent to the bidirectional polyA. While FIG. 1B is illustrative, the order of the ORFs may be varied, as may the immunoglobulin domains encoded thereby. For example, the light chain constant and variable sequences may be located to the left of the polyA and the two heavy chains may be encoded by ORF(s) located to the right of the polyA. Alternatively, one of the heavy chains may be located to the left of the polyA and the ORFs to the right of the polyA encode a second heavy chain and a light chain. Alternatively, the opposite configuration is possible, and the expression cassette to the left of the polyA may be bicistronic. Alternatively, depending upon what domains are encoded, both expression cassettes may be monocistronic (e.g., encoding two immunoadhesins), or both can be bicistronic.

Optionally, the expression configuration exemplified in FIGS. 1A and 1B and described herein may be used to co-express other immunoglobulin constructs. For example, two immunoadhesins (IA) may be expressed from two monocistronic expression cassettes. An immunoadhesin includes a form of antibody that is expressed as single open reading frame containing a single chain variable fragment (scFv) unit (i.e., VH linked to VL or VL linked to VH) fused to an Fc domain (CH2-CH3), (e.g., VH-VL-CH2-CH3 or VL-VH-CH2-CH3). Alternatively, up to four scFvs could be expressed from two bicistronic expression cassettes. In another alternative, an IA may be co-expressed with a full-length antibody. In another alternative, one complete FABS may be co-expressed with a full-length antibody or two complete FABs may be co-expressed. In still another embodiment, other combinations of full-length antibody, IA, or FAB fragment may be co-expressed.

Suitable regulatory control sequences may be selected and obtained from a variety of sources. In one embodiment, a minimal promoter and/or a minimal polyA may be utilized to conserve size.

As used herein, the term "minimal promoter" means a short DNA sequence comprised of a TATA-box and other sequences that serve to specify the site of transcription initiation, to which regulatory elements are added for control of expression. In one embodiment, a promoter refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. In one embodiment, the minimal promoter is a Cytomegalovirus (CMV) minimal promoter. In another embodiment, the minimal promoter is derived from human CMV (hCMV) such as the hCMV immediate early promoter derived minimal promoter (see, US 20140127749, and Gossen and Bujard (Proc. Natl. Acad. Sci. USA, 1992, 89: 5547-5551), which are incorporated herein by reference). In another embodiment, the minimal promoter is derived from a viral source such as, for example: SV40 early or late promoters, cytomegalovirus (CMV) immediate early promoters, or Rous Sarcoma Virus (RSV) early promoters; or from eukaryotic cell promoters, for example, beta actin promoter (Ng, Nuc. Acid Res. 17:601-615, 1989; Quitsche et al., J. Biol. Chem. 264:9539-9545, 1989), GADPH promoter (Alexander, M. C. et al., Proc. Nat. Acad. Sci. USA 85:5092-5096, 1988, Ercolani, L. et al., J. Biol. Chem. 263:15335-15341, 1988), TK-1 (thymidine kinase) promoter, HSP (heat shock protein) promoters, UbB or UbC promoter, PGK, Ef1-alpha promoter or any eukaryotic promoter containing a TATA box (US Published Application No. 2014/0094392). In another embodiment, the minimal promoter includes a mini-promoter, such as the CLDN5 mini-promoter described in US Published Application No. 2014/0065666. In another embodiment, the minimal promoter is the Thymidine Kinase (TK) promoter. In one embodiment, the minimal promoter is tissue specific, such as one of the muscle-cell specific promoters, minimal TnISlow promoter, a minimal TnIFast promoter or a muscle creatine kinase promoter (US Published Application No. 2012/0282695). Each of these documents is incorporated herein by reference.

In one embodiment, the polyadenylation (poly(A)) signal is a minimal poly(A) signal, i.e., the minimum sequence required for efficient polyadenylation. In one embodiment, the minimal poly(A) is a synthetic poly(A), such as that described in Levitt et al, Genes Dev., 1989 July, 3(7):1019-25; and Xia et al, Nat Biotechnol. 2002 October; 20(10): 1006-10. Epub 2002 Sep. 16. In another embodiment, the poly(A) is derived from the rabbit beta-globin poly(A). In one embodiment, the polyA acts bidirectionally (An et al, 2006, PNAS, 103(49): 18662-18667. In one embodiment, the poly(A) is derived from the SV40 early poly A signal sequence. Each of these documents is incorporated herein by reference.

As described herein, in one embodiment, a single enhancer, or the same enhancer, may regulate the transcription of multiple heterologous genes in the plasmid construct. Various enhancers suitable for use in the invention are known in the art and include, for example, the CMV early enhancer, Hoxc8 enhancer, nPE1 and nPE2. Additional enhancers useful herein are described in Andersson et al, Nature, 2014 March, 507(7493):455-61, which is incorporated herein by reference. Still other enhancer elements may include, e.g., an apolipoprotein enhancer, a zebrafish enhancer, a GFAP enhancer element, and tissue specific enhancers such as described in WO 2013/1555222, woodchuck hepatitis post-transcriptional regulatory element. Additionally, or alternatively, other, e.g., the hybrid human cytomegalovirus (HCMV)-immediate early (IE)-PDGR promoter or other promoter-enhancer elements may be selected. To enhance expression the other elements can be introns (like promega intron or chimeric chicken globin-human immunoglobulin intron). Other promoters and enhancers useful herein can be found in the Mammalian Promoter/Enhancer Database found at promoter.cdb.riken.jp/.

The constructs described herein may further contain other expression control or regulatory sequences such as, e.g., include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A promoter may be selected from amongst a constitutive promoter, a tissue-specific promoter, a cell-specific promoter, a promoter responsive to physiologic cues, or an regulatable promoter [see, e.g., WO 2011/126868 and WO 2013/049492].

These control sequences are "operably linked" to the immunoglobulin construct gene sequences. As used herein, the term "operably linked" refers to both expression control sequences that are contiguous with the gene of interest and expression control sequences that act in trans or at a distance to control the gene of interest.

Examples of constitutive promoters suitable for controlling expression of the antibody domains include, but are not limited to chicken β-actin (CB) or beta actin promoters from other species, human cytomegalovirus (CMV) promoter, the early and late promoters of simian virus 40 (SV40), U6 promoter, metallothionein promoters, EF1α promoter, ubiquitin promoter, hypoxanthine phosphoribosyl transferase (HPRT) promoter, dihydrofolate reductase (DHFR) promoter (Scharfmann et al., Proc. Natl. Acad. Sci. USA 88:4626-4630 (1991)), adenosine deaminase promoter, phosphoglycerol kinase (PGK) promoter, pyruvate kinase promoter, phosphoglycerol mutase promoter, the β-actin promoter (Lai et al., Proc. Natl. Acad. Sci. USA 86: 10006-10010 (1989)), UbB, UbC, the long terminal repeats (LTR) of Moloney Leukemia Virus and other retroviruses, the thymidine kinase promoter of Herpes Simplex Virus and other constitutive promoters known to those of skill in the art. Examples of tissue- or cell-specific promoters suitable for use in the present invention include, but are not limited to, endothelin-I (ET-I) and Flt-I, which are specific for endothelial cells, FoxJ1 (that targets ciliated cells).

Inducible promoters suitable for controlling expression of the antibody domains include promoters responsive to exogenous agents (e.g., pharmacological agents) or to physiological cues. These response elements include, but are not limited to a hypoxia response element (EIRE) that binds HIF-Iα and β, a metal-ion response element such as described by Mayo et al. (1982, Cell 29:99-108); Brinster et al. (1982, Nature 296:39-42) and Searle et al. (1985, Mol. Cell. Biol. 5:1480-1489); or a heat shock response element such as described by Nouer et al. (in: Heat Shock Response, ed. Nouer, L., CRC, Boca Raton, Fla., pp I67-220, 1991).

In one embodiment, expression of an open reading frame is controlled by a regulatable promoter that provides tight control over the transcription of the ORF (gene), e.g., a pharmacological agent, or transcription factors activated by a pharmacological agent or in alternative embodiments, physiological cues. Examples of regulatable promoters which are ligand-dependent transcription factor complexes that may be used include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. Examples of such systems, include, without limitation, the ARGENT™ Transcriptional Technology (ARIAD Pharmaceuticals, Cambridge, Mass.). Examples of such promoter systems are described, e.g., in WO 2012/145572, which is incorporated by reference herein.

Still other promoters may include, e.g., human cytomegalovirus (CMV) immediate-early enhancer/promoter, the SV40 early enhancer/promoter, the JC polvomavirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter. The promoters may the same or different for each expression cassette.

For use in producing an AAV viral vector (e.g., a recombinant (r) AAV), the expression cassettes can be carried on any suitable vector, e.g., a plasmid, which is delivered to a packaging host cell. The plasmids useful in this invention may be engineered such that they are suitable for replication and packaging in prokaryotic cells, mammalian cells, or both. Suitable transfection techniques and packaging host cells are known and/or can be readily designed by one of skill in the art.

Methods for generating and isolating AAVs suitable for use as vectors are known in the art. See generally, e.g., Grieger & Samulski, 2005, "Adeno-associated virus as a gene therapy vector: Vector development, production and clinical applications," *Adv. Biochem. Engin/Biotechnol.* 99: 119-145; Buning et al., 2008, "Recent developments in adeno-associated virus vector technology," *J. Gene Med.* 10:717-733; and the references cited below, each of which is incorporated herein by reference in its entirety. For packaging a transgene into virions, the ITRs are the only AAV components required in cis in the same construct as the nucleic acid molecule containing the expression cassettes. The cap and rep genes can be supplied in trans.

As described above, the term "about" when used to modify a numerical value means a variation of ±10%, unless otherwise specified.

As used throughout this specification and the claims, the terms "comprise" and "contain" and its variants including, "comprises", "comprising", "contains" and "containing", among other variants, is inclusive of other components, elements, integers, steps and the like. The term "consists of" or "consisting of" are exclusive of other components, elements, integers, steps and the like.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., any one of the modified ORFs provided herein) when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Generally, these programs are used at default settings, although one skilled in the art can alter these settings as needed. Alternatively, one of skill in the art can utilize another algorithm or computer program that provides at least the level of identity or alignment as that provided by the referenced algorithms and programs. This definition also refers to, or can be applied to, the compliment of a sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of an amino acid or nucleic acid sequences.

Typically, when an alignment is prepared based upon an amino acid sequence, the alignment contains insertions and deletions which are so identified with respect to a reference AAV sequence and the numbering of the amino acid residues is based upon a reference scale provided for the alignment. However, any given AAV sequence may have fewer amino acid residues than the reference scale. In the present invention, when discussing the parental sequence, the term "the same position" or the "corresponding position" refers to the amino acid located at the same residue number in each of the sequences, with respect to the reference scale for the aligned sequences. However, when taken out of the alignment, each of the proteins may have these amino acids located at different residue numbers. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCK-MAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, *Nucl. Acids. Res.*, "A comprehensive comparison of multiple sequence alignments", 27(13):2682-2690 (1999).

In one embodiment, the expression cassettes described herein are engineered into a genetic element (e.g., a shuttle plasmid) which transfers the immunoglobulin construct sequences carried thereon into a packaging host cell for production a viral vector. In one embodiment, the selected genetic element may be delivered to a an AAV packaging cell by any suitable method, including transfection, electroporation, liposome delivery, membrane fusion techniques, high velocity DNA-coated pellets, viral infection and protoplast fusion. Stable AAV packaging cells can also be made. Alternatively, the expression cassettes may be used to generate a viral vector other than AAV, or for production of mixtures of antibodies in vitro. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, N.Y. (2012).

AAV Vectors

A recombinant AAV vector (AAV viral particle) may comprise, packaged within an AAV capsid, a nucleic acid molecule containing a 5' AAV ITR, the expression cassettes described herein and a 3' AAV ITR. As described herein, an expression cassette may contain regulatory elements for an open reading frame(s) within each expression cassette and the nucleic acid molecule may optionally contain additional regulatory elements.

The AAV vector may contain a full-length AAV 5' inverted terminal repeat (ITR) and a full-length 3' ITR. A shortened version of the 5' ITR, termed ΔITR, has been described in which the D-sequence and terminal resolution site (trs) are deleted. The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

Where a pseudotyped AAV is to be produced, the ITRs are selected from a source which differs from the AAV source of the capsid. For example, AAV2 ITRs may be selected for use with an AAV capsid having a particular efficiency for a selected cellular receptor, target tissue or viral target. In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. However, other sources of AAV ITRs may be utilized.

A variety of AAV capsids have been described. Methods of generating AAV vectors have been described extensively in the literature and patent documents, including, e.g., WO 2003/042397; WO 2005/033321, WO 2006/110689; U.S. Pat. No. 7,588,772 B2. The source of AAV capsids may be selected from an AAV which targets a desired tissue. For example, suitable AAV may include, e.g., AAV9 [U.S. Pat. No. 7,906,111; US 2011-0236353-A1], rh10 [WO 2003/042397] and/or hu37 [see, e.g., U.S. Pat. No. 7,906,111; US 2011-0236353-A1]. However, other AAV, including, e.g., AAV1, AAV2, AAV3, AAV4, AAV5, AAV6, AAV7, AAV8, [U.S. Pat. No. 7,790,449; U.S. Pat. No. 7,282,199] and others. However, other sources of AAV capsids and other viral elements may be selected, as may other immunoglobulin constructs and other vector elements.

A single-stranded AAV viral vector is provided. Methods for generating and isolating AAV viral vectors suitable for delivery to a subject are known in the art. See, e.g., U.S. Pat. No. 7,790,449; U.S. Pat. No. 7,282,199; WO 2003/042397; WO 2005/033321, WO 2006/110689; and U.S. Pat. No. 7,588,772 B2]. In one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

Uses and Regimens

The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, maltose, and water. The selection of the carrier is not a limitation of the present invention. Optionally, the compositions of the invention may contain, in addition to the rAAV and carrier(s), other conventional pharmaceutical ingredients, such as preservatives, or chemical stabilizers.

Methods for using these rAAV, e.g., for passive immunization are described, e.g., in WO 2012/145572. Other methods of delivery and uses will be apparent to one of skill in the art. For example, a regimen as described herein may comprise, in addition to one or more of the combinations described herein, further combination with one or more of a biological drug, a small molecule drug, a chemotherapeutic agent, immune enhancers, radiation, surgery, and the like. A biological drug as described herein, is based on a peptide, polypeptide, protein, enzyme, nucleic acid molecule, vector (including viral vectors), or the like.

In a combination therapy, the AAV-delivered immunoglobulin construct described herein is administered before, during, or after commencing therapy with another agent, as well as any combination thereof, i.e., before and during, before and after, during and after, or before, during and after commencing the therapy. For example, the AAV can be administered between 1 and 30 days, preferably 3 and 20 days, more preferably between 5 and 12 days before commencing radiation therapy. In another embodiment of the invention, chemotherapy is administered concurrently with or, more preferably, subsequent to AAV-mediated immunoglobulin (antibody) therapy. In still other embodiments, the compositions of the invention may be combined with other biologics, e.g., recombinant monoclonal antibody drugs, antibody-drug conjugates, or the like. Further, combinations of different AAV-delivered immunoglobulin constructs such as are discussed above may be used in such regimens.

Any suitable method or route can be used to administer AAV-containing compositions as described herein, and optionally, to co-administer other active drugs or therapies in conjunction with the AAV-mediated antibodies described herein. Routes of administration include, for example, systemic, oral, intravenous, intraperitoneal, subcutaneous, or intramuscular administration.

Targets for the immunoglobulin constructs described herein may be selected from a variety of pathogens, including, e.g., bacterial, viral, fungal and parasitic infectious agents. Suitable targets may further include cancer or cancer-associated antigens, or the like. Still other targets may include an autoimmune condition such as rheumatoid arthritis (RA) or multiple sclerosis (MS).

Examples of viral targets include influenza virus from the orthomyxovirudae family, which includes: Influenza A, Influenza B, and Influenza C. The type A viruses are the most virulent human pathogens. The serotypes of influenza A which have been associated with pandemics include, H1N1, which caused Spanish Flu in 1918, and Swine Flu in 2009; H2N2, which caused Asian Flu in 1957; H3N2, which caused Hong Kong Flu in 1968; H5N1, which caused Bird Flu in 2004; H7N7; H1N2; H9N2; H7N2; H7N3; and H10N7.

Broadly neutralizing antibodies against influenza A have been described. As used herein, a "broadly neutralizing antibody" refers to a neutralizing antibody which can neutralize multiple strains from multiple subtypes. For example, CR6261 [The Scripps Institute/Crucell] has been described as a monoclonal antibody that binds to a broad range of the influenza virus including the 1918 "Spanish flu" (SC1918/H1) and to a virus of the H5N1 class of avian influenza that jumped from chickens to a human in Vietnam in 2004 (Viet04/H5). CR6261 recognizes a highly conserved helical region in the membrane-proximal stem of hemagglutinin, the predominant protein on the surface of the influenza virus. This antibody is described in WO 2010/130636, incorporated by reference herein. Another neutralizing antibody, F10 [XOMA Ltd] has been described as being useful against H1N1 and H5N1. [Sui et al, Nature Structural and Molecular Biology (Sui, et al. 2009, 16(3):265-73)] Other antibodies against influenza, e.g., Fab28 and Fab49, may be selected. See, e.g., WO 2010/140114 and WO 2009/115972, which are incorporated by reference. Still other antibodies, such as those described in WO 2010/010466, US Published Patent Publication US/2011/076265, and WO 2008/156763, may be readily selected.

Other target pathogenic viruses include, arenaviruses (including funin, machupo, and Lassa), filoviruses (including Marburg and Ebola), hantaviruses, picornaviridae (including rhinoviruses, echovirus), coronaviruses, paramyxovirus, morbillivirus, respiratory syncytial virus, togavirus, coxsackievirus, parvovirus B19, parainfluenza, adenoviruses, reoviruses, variola (Variola major (Smallpox)) and Vaccinia (Cowpox) from the poxvirus family, and varicella-zoster (pseudorabies).

Viral hemorrhagic fevers are caused by members of the arenavirus family (Lassa fever) (which family is also associated with Lymphocytic choriomeningitis (LCM)), Filovirus (ebola virus), and hantavirus (puremala). The members of picornavirus (a subfamily of rhinoviruses), are associated with the common cold in humans. The coronavirus family includes a number of non-human viruses such as infectious bronchitis virus (poultry), porcine transmissible gastroenteric virus (pig), porcine hemagglutinatin encephalomyelitis virus (pig), feline infectious peritonitis virus (cat), feline enteric coronavirus (cat), canine coronavirus (dog). The human respiratory coronaviruses, have been putatively associated with the common cold, non-A, B or C hepatitis, and sudden acute respiratory syndrome (SARS). The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus (RSV). The parvovirus family includes feline parvovirus (feline enteritis), feline panleucopeniavirus, canine parvovirus, and porcine parvovirus.

The adenovirus family includes viruses (EX, AD7, ARD, O.B.) which cause respiratory disease.

A neutralizing antibody construct against a bacterial pathogen may also be selected for use in the present invention. In one embodiment, the neutralizing antibody construct is directed against the bacteria itself. In another embodiment, the neutralizing antibody construct is directed against a toxin produced by the bacteria. Examples of airborne bacterial pathogens include, e.g., *Neisseria meningitidis* (meningitis), *Klebsiella pneumonia* (pneumonia), *Pseudomonas aeruginosa* (pneumonia), *Pseudomonas pseudomallei* (pneumonia), *Pseudomonas mallei* (pneumonia), *Acinetobacter* (pneumonia), *Moraxella catarrhalis, Moraxella lacunata, Alkaligenes, Cardiobacterium, Haemophilus influenzae* (flu), *Haemophilus parainfluenzae, Bordetella pertussis* (whooping cough), *Francisella tularensis* (pneumonia/fever), *Legionella pneumonia* (Legionnaires disease), *Chlamydia psittaci* (pneumonia), *Chlamydia pneumoniae* (pneumonia), *Mycobacterium tuberculosis* (tuberculosis (TB)), *Mycobacterium kansasii* (TB), *Mycobacterium avium* (pneumonia), *Nocardia asteroides* (pneumonia), *Bacillus anthracis* (anthrax), *Staphylococcus aureus* (pneumonia), *Streptococcus pyogenes* (scarlet fever), *Streptococcus pneumoniae* (pneumonia), *Corynebacteria diphtheria* (diphtheria), *Mycoplasma pneumoniae* (pneumonia).

The causative agent of anthrax is a toxin produced by *Bacillus anthracis*. Neutralizing antibodies against protective agent (PA), one of the three peptides which form the toxoid, have been described. The other two polypeptides consist of lethal factor (LF) and edema factor (EF). Anti-PA neutralizing antibodies have been described as being effective in passively immunization against anthrax. See, e.g., U.S. Pat. No. 7,442,373; R. Sawada-Hirai et al, J Immune Based Ther Vaccines. 2004; 2: 5. (on-line 2004 May 12). Still other anti-anthrax toxin neutralizing antibodies have been described and/or may be generated. Similarly, neutralizing antibodies against other bacteria and/or bacterial toxins may be used to generate an AAV-delivered anti-pathogen construct as described herein.

Other infectious diseases may be caused by airborne fungi including, e.g., *Aspergillus* species, *Absidia corymbifera, Rhixpus stolonifer, Mucor plumbeaus, Cryptococcus neoformans, Histoplasm capsulatum, Blastomyces dermatitidis, Coccidioides immitis, Penicillium* species, *Micropolyspora faeni, Thermoactinomyces vulgaris, Alternaria alternate, Cladosporium species, Helminthosporium*, and *Stachybotrys* species.

In addition, passive immunization may be used to prevent fungal infections (e.g., athlete's foot), ringworm, or viruses, bacteria, parasites, fungi, and other pathogens which can be transmitted by direct contact. In addition, a variety of conditions which affect household pets, cattle and other livestock, and other animals. For example, in dogs, infection of the upper respiratory tract by canine sinonasal aspergillosis causes significant disease. In cats, upper respiratory disease or feline respiratory disease complex originating in the nose causes morbidity and mortality if left untreated. Cattle are prone to infections by the infectious bovine rhinotracheitis (commonly called IBR or red nose) is an acute, contagious virus disease of cattle. In addition, cattle are prone to Bovine Respiratory Syncytial Virus (BRSV) which causes mild to severe respiratory disease and can impair resistance to other diseases. Still other pathogens and diseases will be apparent to one of skill in the art. See, e.g., U.S. Pat. No. 5,811,524, which describes generation of anti-respiratory syncytial virus (RSV) neutralizing antibodies. The techniques described therein are applicable to other pathogens. Such an antibody may be used intact or its sequences (scaffold) modified to generate an artificial or recombinant neutralizing antibody construct. Such methods have been described [see, e.g., WO 2010/13036; WO 2009/115972; WO 2010/140114].

Anti-neoplastic immunoglobulins as described herein may target a human epidermal growth factor receptor (HER), such as HER2. For example, trastuzumab is a recombinant IgG1 kappa, humanized monoclonal antibody that selectively binds with high affinity in a cell-based assay (Kd=5 nM) to the extracellular domain of the human epidermal growth factor receptor protein. The commercially available product is produced in CHO cell culture. See, e.g., www.drugbank.ca/drugs/DB00072. The amino acid sequences of the trastuzumab light chains 1 and 2 and heavy chains 1 and 2, as well as sequences obtained from a study of the x-ray structure of trastuzumab, are provided on this database at accession number DB00072, which sequences are incorporated herein by reference. See, also, 212-Pb-TCMC-trastuzumab [Areva Med, Bethesda, Md.]. Another antibody of interest includes, e.g., pertuzumab, a recombinant humanized monoclonal antibody that targets the extracellular dimerization domain (Subdomain II) of the human epidermal growth factor receptor 2 protein (HER2). It consists of two heavy chains and two lights chains that have 448 and 214 residues respectively. FDA approved Jun. 8, 2012. The amino acid sequences of its heavy chain and light chain are provided, e.g., in www.drugbank.ca/drugs/DB06366 (synonyms include 2C4, MOAB 2C4, monoclonal antibody 2C4, and rhuMAb-2C4) on this database at accession number DB06366. In addition to HER2, other HER targets may be selected.

For example, MM-121/SAR256212 is a fully human monoclonal antibody that targets the HER3 receptor [Merrimack's Network Biology] and which has been reported to be useful in the treatment of non-small cell lung cancer (NSCLC), breast cancer and ovarian cancer. SAR256212 is an investigational fully human monoclonal antibody that targets the HER3 (ErbB3) receptor [Sanofi Oncology]. Another anti-Her3/EGFR antibody is RG7597 [Genentech], described as being useful in head and neck cancers. Another antibody, margetuximab (or MGAH22), a next-generation, Fc-optimized monoclonal antibody (mAb) that targets HER [MacroGenics], may also be utilized.

Alternatively, other human epithelial cell surface markers and/or other tumor receptors or antigens may be targeted. Examples of other cell surface marker targets include, e.g., 5T4, CA-125, CEA (e.g., targeted by labetuzumab), CD3, CD19, CD20 (e.g., targeted by rituximab), CD22 (e.g., targeted by epratuzumab or veltuzumab), CD30, CD33, CD40, CD44, CD51 (also integrin $\alpha_v\beta_3$), CD133 (e.g., glioblastoma cells), CTLA-4 (e.g., Ipilimumab used in treatment of, e.g., neuroblastoma)), Chemokine (C-X-C Motif) Receptor 2 (CXCR2) (expressed in different regions in brain; e.g., Anti-CXCR2 (extracellular) antibody #ACR-012 (Alomene Labs)); EpCAM, fibroblast activation protein (FAP) [see, e.g., WO 2012020006 A2, brain cancers], folate receptor alpha (e.g., pediatric ependymal brain tumors, head and neck cancers), fibroblast growth factor receptor 1 (FGFR1) (see, et al, WO2012125124A1 for discussion treatment of cancers with anti-FGFR1 antibodies), FGFR2 (see, e.g., antibodies described in WO2013076186A and WO2011143318A2), FGFR3 (see, e.g., antibodies described in U.S. Pat. No. 8,187,601 and WO2010111367A1), FGFR4 (see, e.g., anti-FGFR4 antibodies described in WO2012138975A1), hepatocyte growth factor (HGF) (see, e.g., antibodies in WO2010119991A3), integrin $\alpha_5\beta_1$, IGF-1 receptor, gangioloside GD2 (see, e.g., antibodies described in WO2011160119A2), ganglioside GD3, transmembrane glycoprotein NMB (GPNMB) (associated with gliomas, among others and target of the antibody glembatumumab (CR011), mucin, MUC1, phosphatidylserine (e.g., targeted by bavituximab, Peregrine Pharmaceuticals, Inc], prostatic carcinoma cells, PD-L1 (e.g., nivolumab (BMS-936558, MDX-1106, ONO-4538), a fully human gG4, e.g., metastatic melanoma], platelet-derived growth factor receptor, alpha (PDGFR $\alpha$) or CD140, tumor associated glycoprotein 72 (TAG-72), tenascin C, tumor necrosis factor (TNF) receptor (TRAIL-R2), vascular endothelial growth factor (VEGF)-A (e.g., targeted by bevacizumab) and VEGFR2 (e.g., targeted by ramucirumab).

Other antibodies and their targets include, e.g., APN301 (hu14.19-1L2), a monoclonal antibody [malignant melanoma and neuroblastoma in children, Apeiron Biolgics, Vienna, Austria]. See, also, e.g., monoclonal antibody, 8H9, which has been described as being useful for the treatment of solid tumors, including metastatic brain cancer. The monoclonal antibody 8H9 is a mouse IgG1 antibody with specificity for the B7H3 antigen [United Therapeutics Corporation]. This mouse antibody can be humanized. Still other immunoglobulin constructs targeting the B7-H3 and/or the B7-H4 antigen may be used in the invention. Another antibody is S58 (anti-GD2, neuroblastoma). Cotara™ [Perregrince Pharmaceuticals] is a monoclonal antibody described for treatment of recurrent glioblastoma. Other antibodies may include, e.g., avastin, ficlatuzumab, medi-575, and olaratumab. Still other immunoglobulin constructs or monoclonal antibodies may be selected for use in the invention. See, e.g., Medicines in Development Biologics, 2013 Report, pp. 1-87, a publication of PhRMA's Communications & Public Affairs Department. (202) 835-3460, which is incorporated by reference herein.

For example, immunogens may be selected from a variety of viral families. Example of viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies).

Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bunyaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected as targets. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. No. 5,891,994 and U.S. Pat. No. 6,193,981.] See, also, the HIV and SIV proteins described in D. H. Barouch et al, J. Virol., 75(5):2462-2467 (March 2001), and R. R. Amara, et al, *Science,* 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins has been described or could readily be made by one of skill in the art. See, e.g., the modified gag protein that is described in U.S. Pat. No. 5,972,596.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family includes feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek's disease virus, and rhadinovirus. The poxvirus family includes the sub-family chordopoxvirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxvirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

Other pathogenic targets for antibodies may include, e.g., bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; pseudomonas, acinetobacteria and eikenella; melioidosis; salmonella; shigella; haemophilus; moraxella; *H. ducreyi* (which causes chancroid); brucella; *Franisella tularensis* (which causes tularemia); yersinia (pasteurella); streptobacillus moniliformis and spirillum; Gram-positive bacilli include listeria monocytogenes; erysipelothrix rhusiopathiae; *Corynebacterium diphtheria* (diphtheria); cholera; *B. anthracia* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of mycoplasma and chlamydial infections include: *mycoplasma pneumoniae*; lymphogranuloma venereum; psittacosis; and perinatal chlamydial infections. Pathogenic eukaryotes encompass pathogenic protozoa and helminthes and infections produced thereby include: amebiasis; malaria; leishmaniasis; trypanosomiasis; toxoplasmosis; *Pneumocystis carinii; Trichans; Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Health and Human Services, USA], as agents which have potential for use in biological attacks. For example, some of these biological agents, include, *Bacillus anthracia* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); *Brucella* species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to target antigens from these organisms, viruses, their toxins or other by-products, which will prevent and/or treat infection or other adverse reactions with these biological agents.

The following examples are illustrative only and are not a limitation on the invention described herein.

Example 1: Generation of Vectors Containing Full-Length Antibody Co-Expression Cassettes A series of cis-plasmids were prepared for use in generating an AAV viral particle containing a nucleic acid molecule for delivery to a host target cell. The nucleic acid molecules comprise AAV2 5' and 3' ITR sequences at each terminus, a shared CMV enhancer flanked by two expression cassettes in opposite orientations, where a first expression cassette is controlled by a first minimal CMV promoter and a second expression cassette is controlled by a second minimal CMV promoter. All sequences located between AAV2 ITRs were de novo synthesized by a commercial vendor (GeneArt). All coding sequences for immunoglobulin variable domains were flanked with the unique restriction enzymes to allow convenient shuttling of the desired variable domains. To create constructs with heterologous light chain sequence (kgl), a coding sequence encoding germline light chain (IGKV4-1*01) was de novo synthesized and used to replace FI6 variable light sequence.

Figure 2:
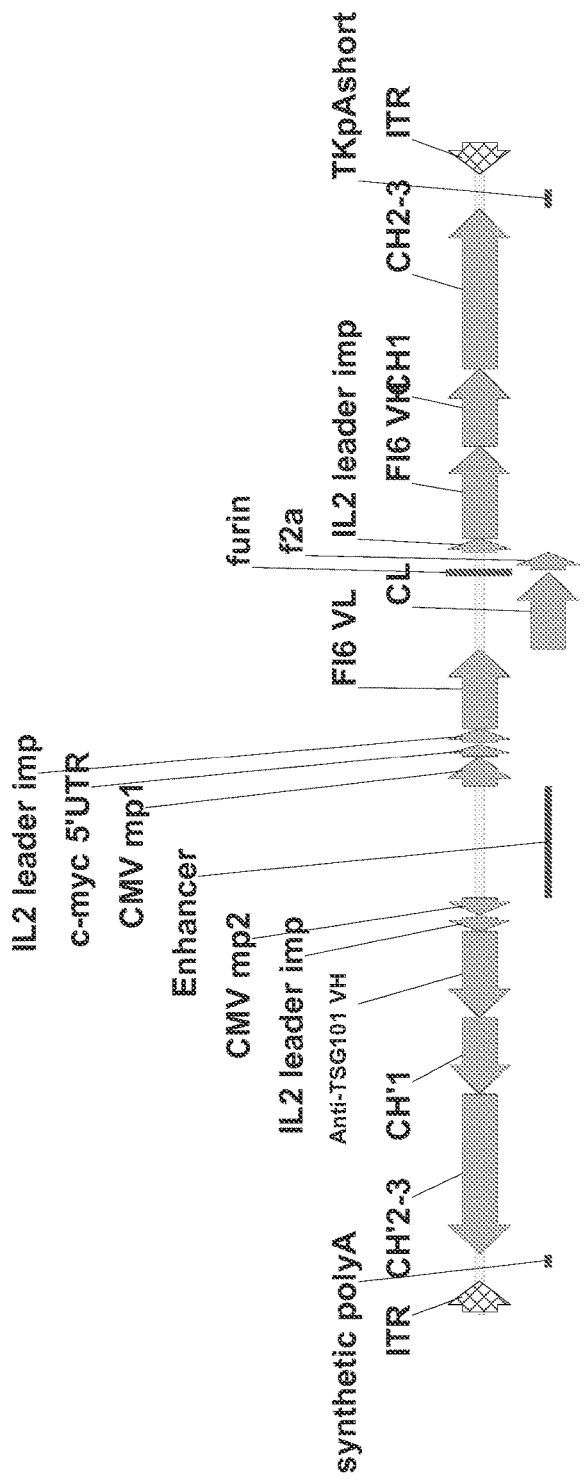
FIG. 2 illustrates a nucleic acid molecule carried by a plasmid for packaging into an AAV capsid, which is used for co-expression of an anti-TSG 101 heavy chain, FI6 influenza heavy chain, and FI6 light chain. These antibody chains utilize heterologous leader from interleukin 2 (IL2). The human CMV enhancer was used in conjunction with CMV promoters. The bicistronic expression cassette contains a furin recognition site and a 2A linker sequence separating the ORF containing the FI6 VL and CL regions from the ORF containing the FI6 heavy chain. The polyA for the expression cassette on the right is a shortened thymidine kinase polyA. The polyA for the expression cassette on the left is a synthetic polyA sequence.
Figure 3:
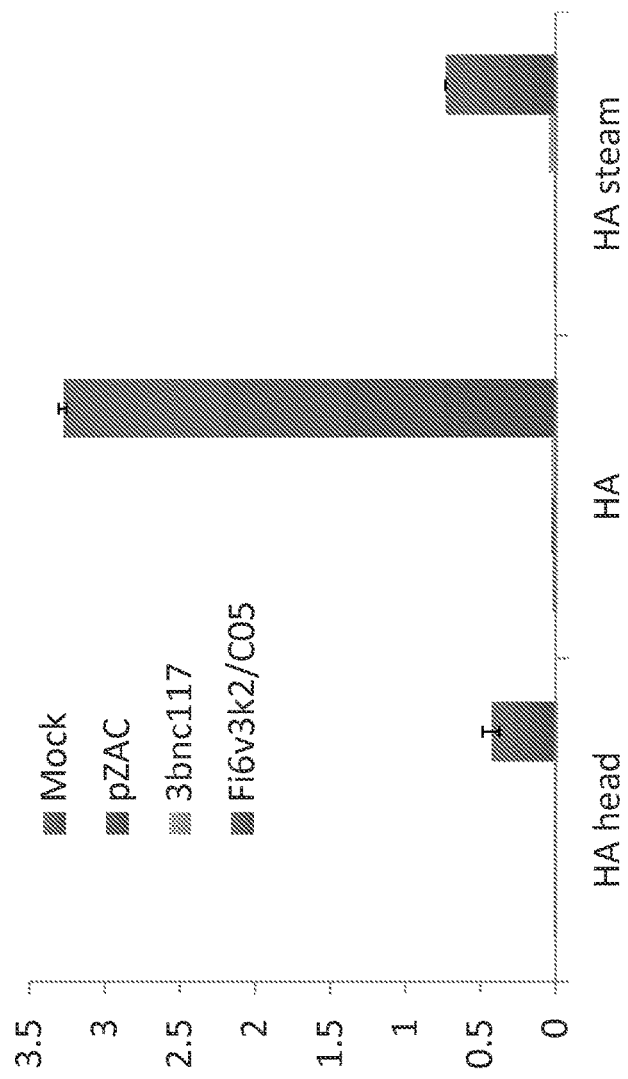
FIG. 3 illustrates the binding ability of an FI6v3k2 antibody co-expressed with a C05 antibody from a recombinant AAV8 prepared as described herein. The results demonstrate the expected binding to full-length HA and the HA stem characteristic of FI6 and binding to HA and HA head only (no stem) characteristic of C05.
Figure 4:
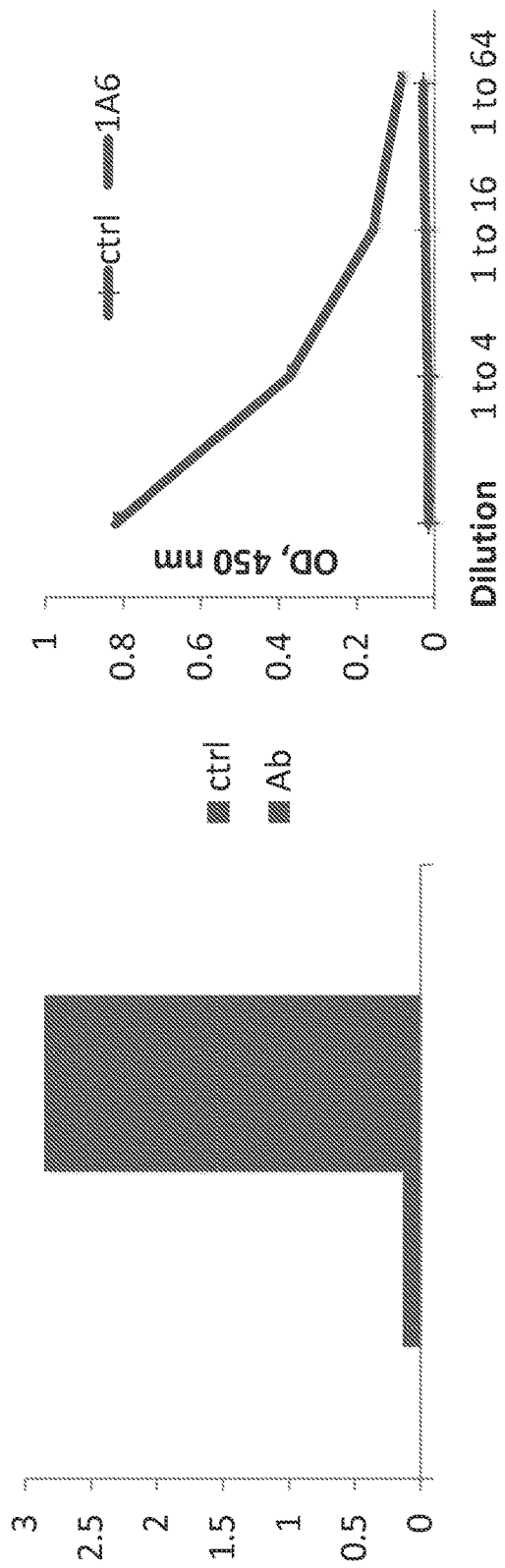
FIGS. 4A-4B illustrates the binding ability of an FI6v3k2 antibody co-expressed with a 1A6 antibody (anti-TSG 101) from a recombinant AAV8 prepared as described herein.
Figure 5:
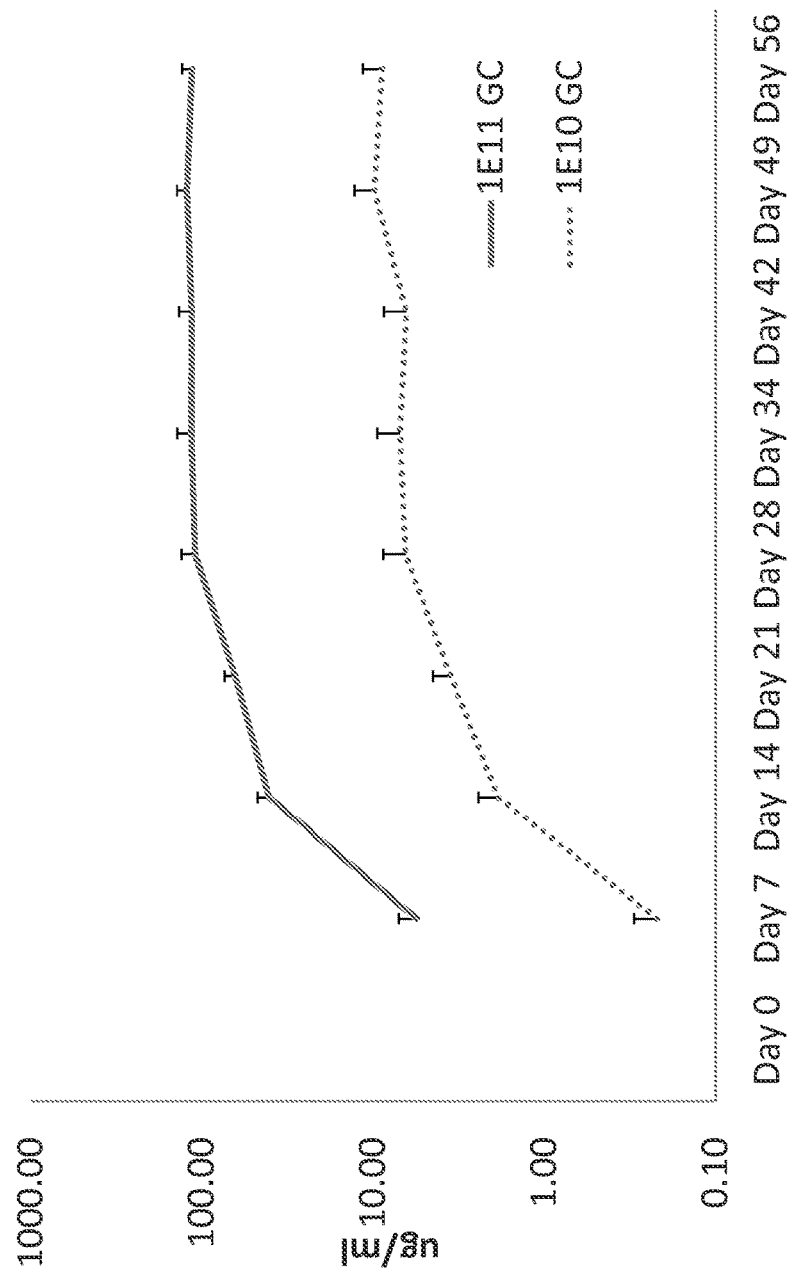
FIG. 5 illustrates systemic expression levels in mice administered FI6 co-expressed from an AAV vector with a second antibody at doses of $1 \times 10^{11}$ genome copies (GC) or $1 \times 10^{10}$ GC.

An exemplary antibody co-expression shuttle is illustrated in FIG. 2. This shuttle contains to the left of the enhancer a first expression cassette which contains, from right to left, a CMV minimal promoter, a heterologous IL2 leader sequence linked to an anti-TSG101 antibody (1A6) variable heavy (VH) domain, a CH'1 domain, and a CH'2-3 domain which has been optimized for expression in humans, and a synthetic polyA. To the right of the enhancer is located a CMV minimal promoter, a heterologous IL2 leader sequence, a FI6k2 (anti-influenza antibody) light chain variable domain and a light chain constant domain, furin cleavage site, the 2a linker from the foot-and-mouth disease virus, an IL2 leader sequence, the FI6v3 VH, CH1, CH2-3, and a thymidine kinase short polyA sequence. CH designations refer to the known antibody allotype G1m17,1.

SEQ ID NO: 1 provides sequences of the FI6 constant regions. The amino acid sequences of the FI6 amino acid light chain is provided in SEQ ID NO: 2.

The cis-plasmid of FIG. 2 was used in a triple transfection method as previously described in, e.g., in U.S. patent application Ser. No. 12/226,558, to generate AAV8 and AAV9 vectors which were used in subsequent studies described herein. The resulting plasmid, pN509_ACE Fib-1A6 MAB_p3160, is 7722 bp in length, the sequence of which is provided in SEQ ID NO: 3, which is incorporated herein by reference together with its features. The encoded sequences for the FI6 variable light (VL) chain [SEQ ID NO:4], FI6 variable heavy [SEQ ID NO: 5], CH1 (SEQ ID NO: 6), CH2-3 [SEQ ID NO: 7] are also provided.

Similar antibody co-expression cis-plasmids were generated by subcloning a seasonal flu antibody (CR8033) or a pandemic flu antibody (C05), or an anti-M2e antibody (TCN-032) in the place of 1A6 heavy variable domain in FIG. 2 using pre-positioned unique restriction sites that allow easy shuffling of the variable domains. These cis-plasmids were in turn used in triple transfection (e.g., performed as described in U.S. patent application Ser. No. 12/226,588) to generate AAV8 and AAV9 vectors used for subsequent studies. Sequences for the pN510_ACE Fi6-C05 MAB shuttle are provided in SEQ ID NO:8; the amino acids sequence of the variable light chain is provided in SEQ ID NO: 9, the constant light is provided in SEQ ID NO: 10, the FI6 variable heavy chain is provided in SEQ ID NO: 11, the CH1 is provided in SEQ ID NO:12 and the CH2-3 is provide in SEQ ID NO: 13. Sequences for the pN514_ACE Fi6-C05 MAB shuttle are provided in SEQ ID NO:19; the amino acids sequence of the constant light is provided in SEQ ID NO: 20, the FI6 variable heavy chain is provided in SEQ ID NO: 21, the CH1 is provided in SEQ ID NO:22 and the CH2-3 is provide in SEQ ID NO: 23. These shuttles were in turn used to generate AAV8 and AAV9 vectors which were used for subsequent studies.

Example 2: Characterization of Products Expressed from AAV8 Vectors Co-Expressing FI6 Monoclonal Antibody (MAB) and IA6 MAB A series of ELISA assays were performed to characterize expression levels and to assess binding of the FI6 MAB co-expressed with the IA6 MAB from the cis plasmid generated as described in Example 1 after transfection into HEK 293 cells. TSG101 peptide was synthesized using f-Moc chemistry by Mimotopes. All flu antigens were procured from a commercial supplier, ImmuneTechnologies, Inc. ProteinA was purchased from Sigma-Aldrich and was used to monitor expression of total human IgG1. Detection of human IgG1 in tissue culture supernatants was measured by either antigen-specific or proteinA capture ELISA. High binding ELISA plates were coated with 2 µg/ml of HA proteins or peptides, or with 5 µg/ml proteinA diluted in PBS and incubated overnight at 4° C. Wells were washed 5-8 times and blocked with 1 mM EDTA, 5% heat inactivated PBS, 0.07% Tween 20 in PBS for one hour at room temperature. Tissue culture supernatants were added to the plates at various dilutions in duplicates and incubated at 37° C. for one hour. Plates were washed, blocked, and Bio-SP-conjugated Affinipures Goat Anti-Human IgG antibody (Jackson ImmunoResearch Laboratories, Inc., West Grove, Pa., USA) was added at a 1:10,000 dilution. After one hour, plates were washed and streptavidin-conjugated horseradish peroxidase (HRP) was added at a 1:30,000 dilution. After one hour, plates were washed 3,3',5,5'-tetramethylbenzidine (TMB) was added. The reaction was stopped after 30 minutes at room temperature using 2N sulfuric acid and plates were read at 450 nm using a BioTek µQuant plate reader (Winooski, Vt., USA).

As expected, no binding is observed of FI6 to the TSG101 peptide, the HA (B/Malaysia/2506/2/004), or the HA (Head region only of influenza strain A/Brisbane/59/2007). FI6 binding is observed for this same strain of influenza when the full-length HA is present, as well as for influenza strain HA(dTM)(A/Beijing/01/2009, H1N1)). As expected, FI6 binding is also observed for Protein A.

According to published reports, FI6 produced according to prior art methods binds to full-length HA and to HA stem, but not to the head only region. These data demonstrate that the co-expressed FI6 monoclonal antibody retains its characteristic binding profile.

Example 3: Characterization of Products Expressed from AAV8 Vectors Co-Expressing FI6 Monoclonal Antibody (MAB) and Pandemic Flu MAB C05

The possibility of differential detection of two different monoclonal antibodies was assessed in a capture assay. Monoclonal antibodies FI6 and C05 co-expressed from a cis-plasmid prepared as described in Example 1 and transfected into HEK293 cells were assessed for binding. FI6 is expected to bind to full-length HA and to HA stem, but not to the head only region. The results of the binding study illustrated in FIG. 3 demonstrate that the co-expressed antibodies retain their characteristic binding. More particularly, binding to full-length HA and the HA stem characteristic of FI6 is observed and binding to HA and HA head only (no stem) characteristic of C05 is also observed. ELISA assays were performed as described in Example 2.

Example 4: Characterization of Products Expressed from AAV8 Vectors Co-Expressing FI6 Monoclonal Antibody (MAB) and a Second Full-Length MAB 6-8 weeks old male RAG KO mice (The Jackson Laboratory Bar Harbor, Me., USA) were housed under pathogen-free conditions at the University of Pennsylvania's Translational Research Laboratories. All animal procedures and protocols were approved by the Institutional Animal Care and Use Committee. Mice were sacrificed by carbon dioxide asphyxiation and death was confirmed by cervical dislocation. For vector administration, mice were anaesthetized with a mixture of 70 mg/kg of body weight ketamine and 7 mg/kg of body weight xylazine by intraperitoneal (IP) injection. Vectors were diluted in phosphate buffered saline (PBS) and IM injections were performed using a Hamilton syringe. Serum was collected weekly via retro-orbital bleeds. Detection of human IgG1 in tissue culture supernatants was measured by proteinA capture ELISA. High binding ELISA plates were coated with 5 μg/ml proteinA diluted in PBS and incubated overnight at 4° C. Wells were washed 5-8 times and blocked with 1 mM EDTA, 5% heat inactivated PBS, 0.07% Tween 20 in PBS. Mouse serum samples were heat inactivated and added to the plates at various dilutions in duplicates and incubated at 37° C. for one hour. Plates were washed, blocked, and Bio-SP-conjugated Affinipures Goat Anti-Human IgG antibody (Jackson ImmunoResearch Laboratories, Inc., West Grove, Pa., USA) was added at a 1:10,000 dilution. After one hour, plates were washed and incubated with streptavidin-conjugated horseradish peroxidase (HRP) at a 1:30,000 dilution. After one hour, plates were washed 3,3',5,5'-tetramethylbenzidine (TMB) was added. The reaction was stopped after 30 minutes at room temperature using 2N sulfuric acid and plates were read at 450 nm using a BioTek μQuant plate reader (Winooski, Vt., USA).

FIG. 5 illustrates systemic expression levels for total human IgG1 in mice administered an AAV vector co-expressing FI6 with IA6 antibody. Mice were injected intramuscularly at doses of $1\times10^{11}$ genome copies (GC) or $1\times10^{10}$ GC. Expression levels were assessed at day 7, 15, 21, 28, 34, 42, 49 and 56 and measured at a concentration of micrograms/mL. A dose dependent increase in expression was observed.

Example 5: Characterization of Products Expressed from AAV8 Vectors Co-Expressing F16 Monoclonal Antibody (MAB) and Three Different Full-Length Monoclonal Antibodies The tables below showing expression levels in mice administered an AAV vector co-expressing FI6 with full-length CR8033, C05, or 1A6 monoclonal antibody. RAG knock-out (KO) mice were injected intramuscularly at doses of $1\times10^{11}$ genome copies (GC) or $1\times10^{10}$ GC as described in the previous example. Expression levels were assessed weekly at days 7, 15, 21, 28, 34, 42, and 49 and measured at a concentration of micrograms/mL. A dose dependent increase in expression was observed for expressed antibodies. The capture antigen used for the assay is Protein A ELISA as described in the previous example.

| | Test Article Fi6v3k2 mAb + CR8033 mAb Dose | | | |
|---|---|---|---|---|
| | $1.00 \times 10^{11}$ | | $1.00 \times 10^{10}$ | |
| | average | stdev. | average | stdev. |
| Day 0 | 0.00 | 0.00 | 0.00 | 0.00 |
| Day 7 | 2.92 | 0.48 | 0.04 | 0.07 |
| Day 14 | 18.30 | 4.79 | 1.24 | 0.66 |
| Day 21 | 33.69 | 7.45 | 2.09 | 0.88 |
| Day 28 | 43.38 | 10.92 | 2.84 | 1.81 |
| Day 35 | 66.45 | 16.61 | 4.47 | 1.86 |
| Day 42 | 64.25 | 12.06 | 4.37 | 2.35 |
| Day 49 | 51.36 | 11.90 | 3.57 | 1.52 |

| | Test Article Fi6v3k2 mAb + C05 mAb Dose | | | |
|---|---|---|---|---|
| | $1.00 \times 10^{11}$ | | $1.00 \times 10^{10}$ | |
| | average | stdev. | average | stdev. |
| Day 0 | 0.00 | 0.00 | 0.00 | 0.00 |
| Day 7 | 1.73 | 0.42 | 0.00 | 0.00 |
| Day 14 | 9.95 | 3.39 | 0.24 | 0.22 |
| Day 21 | 24.74 | 11.66 | 0.81 | 0.24 |
| Day 28 | 22.32 | 4.77 | 1.11 | 0.17 |
| Day 35 | 31.67 | 7.93 | 1.53 | 0.28 |
| Day 42 | 34.69 | 14.46 | 1.83 | 0.29 |
| Day 49 | 26.14 | 5.85 | 1.46 | 0.49 |

| | Test Article Fi6v3k2 mAb + 1A6 mAb Dose | | | |
|---|---|---|---|---|
| | $1.00 \times 10^{11}$ | | $1.00 \times 10^{10}$ | |
| | average | stdev. | average | stdev. |
| Day 0 | 0 | 0 | 0 | 0 |
| Day 7 | 2.70 | 0.75 | 0 | 0 |
| Day 14 | 5.01 | 0.06 | 1.58 | .055 |
| Day 21 | 30.16 | 13.31 | 1.71 | 0.52 |

-continued

| | Test Article Fi6v3k2 mAb + 1A6 mAb Dose | | | |
|---|---|---|---|---|
| | $1.00 \times 10^{11}$ | | $1.00 \times 10^{10}$ | |
| | average | stdev. | average | stdev. |
| Day 28 | 38.18 | 15.99 | 2.16 | 0.59 |
| Day 35 | 55.18 | 18.52 | 4.09 | 1.53 |
| Day 42 | 50.49 | 16.61 | 3.69 | 0.94 |
| Day 49 | 46.66 | 15.59 | 3.73 | 1.09 |

Figure 6B:
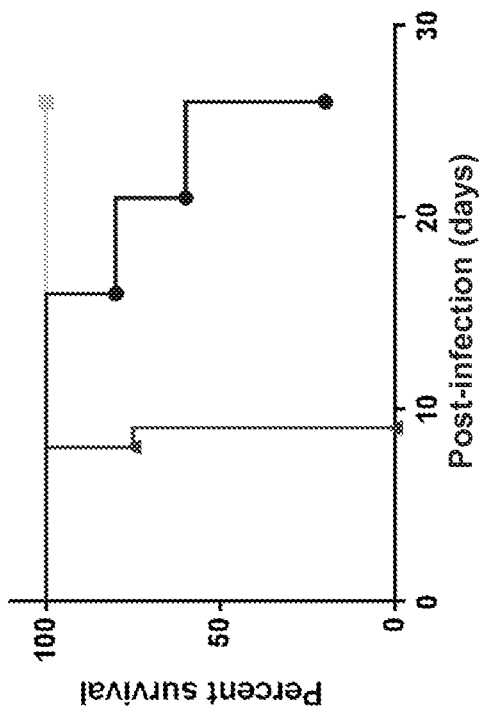
FIGS. 6A-6B illustrate the evaluation of the AAV9.BiD.FI6v3_CR8033mAb delivered intramuscularly (IM) at $1 \times 10^{11}$ GC for protection against challenge with influenza strain PR8.
Figure 6A:
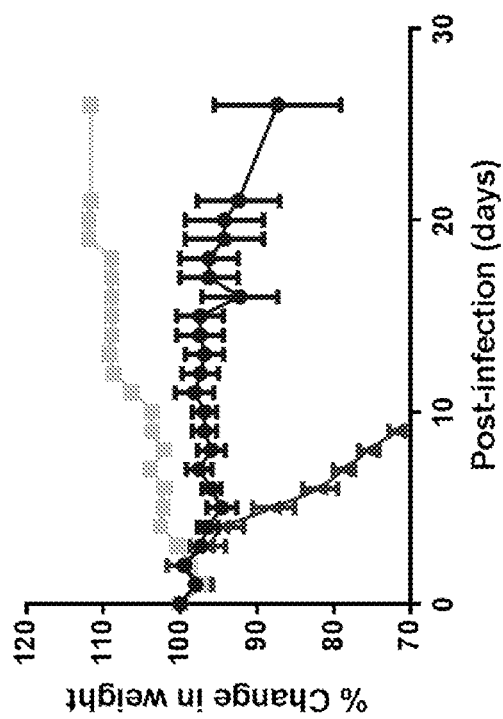

Example 6: Anti-Viral Effect is Conferred by Dual Full-Length Antibodies Expressed from a Single AAV9 and/or AAV8 Vector Intramuscularly A. AAV9.BiD.FI6_CR8033mAb and Influenza A Challenge BALB/c mice were injected with AAV9.BiD.FI6_CR8033mAb delivered intramuscularly (IM) at $1\times10^{11}$ GC. Two weeks later the mice were challenged intranasally with 5LD50 of mouse adapted PR8 (influenza A). The circle represents the AAV9 construct with a bidirectional promoter expressing synthetic FI6 and CR8033 monoclonal antibodies having the same heterologous light chain. The square represents a positive control, i.e., AAV9 expressing a single antibody type FI6 also delivered at $1\times10^{11}$ GC, and the triangle represents naïve animals. FIG. 6B shows survival post-challenge. Administration of the AAV9.BiD.FI6_CR8033mAb at 10 GC/mouse dose allowed partial protection with a significant delay in the weight loss.

B. AAV9.BiD.FI6_CR8033mAb and Influenza B Challenge

For AAV9 vector injection: BALB/c female mice were anesthetized by an intramuscular injection of a 100 mg/kg ketamine/10 mg/kg xylazine mixture in PBS, and AAV9.BiD.FI6_CR8033mAb vector was injected intramuscularly (IM) at $1\times10^{11}$ GC per mouse. BiD vector was compared to an AAV9 expressing a single antibody type CR8033 also delivered at $1\times10^{11}$ GC, and a negative control (naïve animals). FIG. 7B shows survival post-challenge. For influenza challenge, two weeks after vector treatment, AAV-treated and naïve BALB/c mice were weighed and tails color-coded, anesthetized as described above, suspended by their dorsal incisors with their hind limbs supported on a platform, and administered intranasally with 5LD50 of B/Lee/40 (influenza B) in a total volume of 50 µl of PBS as described above. Mice were then weighed daily and monitored for signs of disease or distress. Animals that exhibited behavioral signs of distress or lost 30% of their initial body weight were euthanized by CO2 asphyxiation.

Figure 7A:
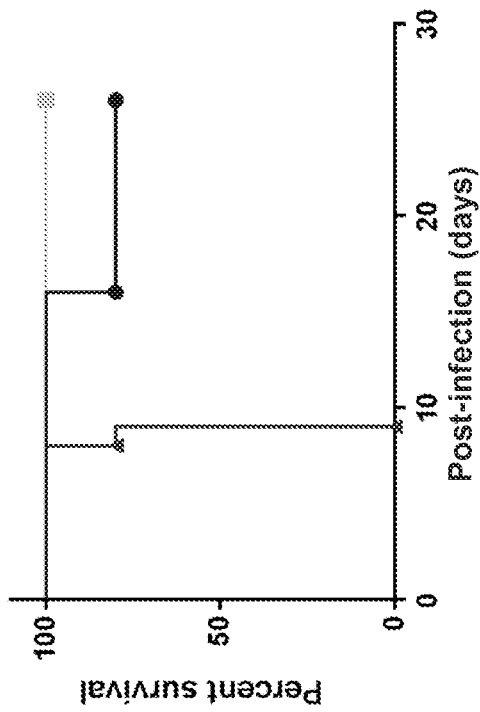
FIGS. 7A-7B illustrate the evaluation of the AAV9.BiD.FI6v3_CR8033mAb delivered intramuscularly (IM) at $1 \times 10^{11}$ GC for protection against challenge with influenza strain B/Lee/40.
Figure 7B:
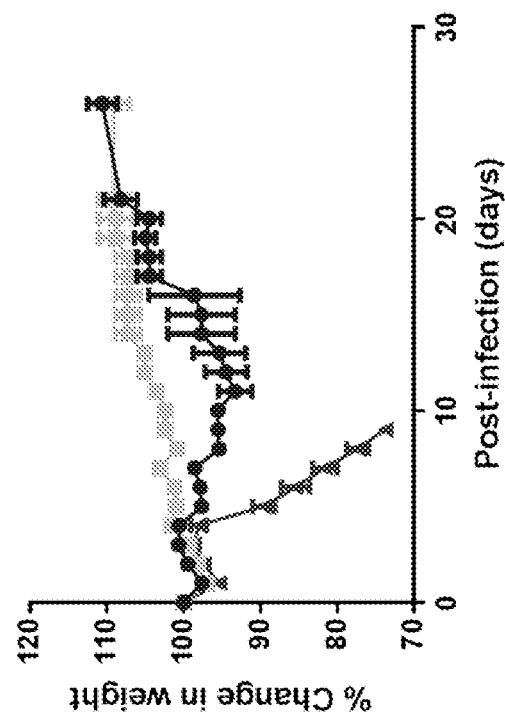

FIG. 7A is a line graph showing percent change in weight. These data show that full protective effect was conferred by the dual expressed antibodies at this dose. FIG. 7B shows survival post-challenge.

C. AAV8.F16-TCN032, AAV8.FI6-1A6, and AAV8.FI6-CR8033 vectors administered IM and mouse adapted PR8 Influenza A challenge.

These vectors were made as described in Example 1. 6-8 weeks old male RAG KO mice (The Jackson Laboratory Bar Harbor, Me., USA) were housed under pathogen-free conditions at the University of Pennsylvania's Translational Research Laboratories. All animal procedures and protocols were approved by the Institutional Animal Care and Use Committee. For vector administration, mice were anaesthetized with a mixture of 70 mg/kg of body weight ketamine and 7 mg/kg of body weight xylazine by intraperitoneal (IP) injection. Vectors were diluted in phosphate buffered saline (PBS) and IM injections were performed using a Hamilton syringe. Serum was collected weekly via retro-orbital bleeds.

Detection of human IgG1 in tissue culture supernatants was measured by proteinA capture ELISA. High binding ELISA plates were coated with 5 µg/ml proteinA diluted in PBS and incubated overnight at 4° C. Wells were washed 5-8 times and blocked with 1 mM EDTA, 5% heat inactivated PBS, 0.07% Tween 20 in PBS. Mouse serum samples were heat inactivated and added to the plates at various dilutions in duplicates and incubated at 37° C. for one hour. Plates were washed, blocked, and Bio-SP-conjugated Affinipures Goat Anti-Human IgG antibody (Jackson ImmunoResearch Laboratories, Inc., West Grove, Pa., USA) was added at a 1:10,000 dilution. After one hour, plates were washed and incubated with streptavidin-conjugated horseradish peroxidase (HRP) at a 1:30,000 dilution. After one hour, plates were washed 3,3',5,5'-tetramethylbenzidine (TMB) was added. The reaction was stopped after 30 minutes at room temperature using 2N sulfuric acid and plates were read at 450 nm using a BioTek µQuant plate reader (Winooski, Vt., USA).

With reference to FIG. 8C, on all panels, expression levels are indicated on Day 56 after vector administration. Couple days after the last orbital bleed on Day 56, mice were weighed and tails color-coded, anesthetized as described above, suspended by their dorsal incisors with their hind limbs supported on a platform, and administered intranasally with 5LD50 of mouse adapted PR8 (influenza A) in a total volume of 50µl of PBS as described above. Mice were then weighed daily and monitored for signs of disease or distress. Animals that exhibited behavioral signs of distress or lost 30% of their initial body weight were euthanized by CO2 asphyxiation and death was confirmed by cervical dislocation. FIG. 8A shows that systemic expression of as little as 25 µg/ml of anti-influenza antibody is sufficient to afford protection in PR8 challenge, but expression of 0.4 µg/ml is insufficient for protection.

D. AAV9. FI6_IA6 mAbs and Influenza A Challenge

An AAV9 vector expressing artificial FI6 and an anti-HIV immunoadhesin, IA6, were assessed for protection against challenge with influenzA A as described above. FIG. 8B shows that expressing 36.5 µg/ml of anti-influenza antibody is sufficient to provide complete protection against challenge with PR8. FIG. 8C shows expressing 6.9 ug/ml of anti-influenza antibodies is not sufficient to protect against PR8 challenge.

Example 7—Generation of Vectors Containing Two Immunoadhesin Co-Expression Cassettes Using a shuttle vector similar to that illustrated in FIG. 2, vectors containing two immunoadhesins have been generated.

In one embodiment, a vector containing FI6 and C05 immunoadhesins was created. The sequences from a plasmid carrying the FI6 and C05 immunoadhesin expression cassettes are provided in SEQ ID NO: 36; with the translated encoded sequences provided in SEQ ID NO: 37 (FI6 variable heavy chain), SEQ ID NO: 38 (FI6 variable light chain), and SEQ ID NO: 39 (CH2-3). These sequences and their features are incorporated by reference.

In another embodiment, a vector containing FI6 and CR8033 immunoadhesins was created. The sequences from a plasmid containing the FI6 and CR8033 immunoadhesins are provided in SEQ ID NO:40; with the translated encoded sequences provided in SEQ ID NO: 41 (FI6 VH) and SEQ ID NO: 42 (FI6 variable light). These sequences and their features are incorporated by reference.

AAV may be generated from the immunoadhesin shuttle plasmids described above using techniques known to those of skill in the art.

Additional illustrative shuttle plasmids are as follows.

The sequence of a plasmid pN512_ACE FI6v3kgl-1A6 MAB_p3184 containing a kappa germline light chain that is heterologous to the source of both heavy chains, 1A6 and FI6v3 is provided in SEQ ID NO: 14. The translated encode sequences are provide in SEQ ID NO: 15 (constant light), SEQ ID NO: 16 (FI6 variable heavy), SEQ ID NO: 17 (CH1), and SEQ ID NO: 18 (CH2-3).

The sequences of an intermediate vector which carries the TCN032 heavy and light chain immunoglobulins are provided in SEQ ID NO: 30. The translated amino acid sequences encoded by this plasmid include the TCN032 heavy chain in SEQ ID NO: 31; the CH1 sequence in SEQ ID NO: 32; the FI6 VH chain in SEQ ID NO: 33; the CH1 sequence in SEQ ID NO: 34 and the CH2-3 sequence in SEQ ID NO: 35.

The sequence of a plasmid carrying the TCN032 and FI6 heavy chains and co-expressing two antibodies having these specificities is provided in SEQ ID NO: 43. The translated amino acids of the TCN032 variable heavy chain are in SEQ ID NO: 44, the CH1 is in SEQ ID NO: 45, the hinge-CH2'-CH3' is in SEQ ID NO: 46, the Fi6 VH is in SEQ ID NO: 47, the CH1 is in SEQ ID NO: 48, the CH2-3 is in SEQ ID NO: 49, and the ampicillin resistance gene is in SEQ ID NO: 50. These sequences and their features are incorporated herein by reference.

Sequence Listing Free Text

The following information is provided for sequences containing free text under numeric identifier <223>.

| SEQ ID NO: (containing free text) | Free text under <223> |
|---|---|
| 1 | <223> Synthetic sequence encoding FI6 heavy chain<br><220><br><221> CDS<br><222> (1) ... (705)<br><223> FI6 constant |
| 3 | <223> plasmid carrying FI6 and 1A6 antibodies<br><220><br><221> polyA_signal<br><222> (191) ... (239)<br><223> synthetic\polyA<br><220><br><221> misc_feature<br><222> (246) ... (914)<br><223> complement - CH'2-3<br><220><br><221> misc_feature<br><222> (915) ... (1235)<br><223> complement - CH'1<br><220><br><221> misc_feature<br><222> (1236) ... (1598)<br><223> complement - 1A6\VH |
|  | <220><br><221> misc_feature<br><222> (1599) ... (1655)<br><223> complement - leader<br><220><br><221> misc_feature<br><222> (1734) ... (2202)<br><223> Enhancer<br><220><br><221> misc_feature<br><222> (2388) ... (2444)<br><223> leader<br><220><br><221> CDS<br><222> (2445) ... (2777)<br><223> FI6\VL<br><220><br><221> misc_feature<br><222> (3183) ... (3242)<br><223> leader<br><220><br><221> CDS<br><222> (3243) ... (3629)<br><223> FI6\VH<br><220><br><221> CDS<br><222> (3630) ... (3950)<br><223> CH1<br><220><br><221> CDS<br><222> (3951) ... (4619)<br><223> CH2-3<br><220><br><221> polyA_signal<br><222> (4626) ... (4703)<br><223> TKpAshort<br><220><br><221> misc_feature<br><222> (6995) ... (7283)<br><223> COL\E1\Origin |
| 8 | <223> Plasmid encoding FI6 and C05 monoclonal antibodies<br><220><br><221> polyA_signal<br><222> (204) ... (252)<br><223> synthetic\polyA<br><220><br><221> misc_feature<br><222> (259) ... (927)<br><223> complement - CH'2-3<br><220><br><221> misc_feature<br><222> (928) ... (1248)<br><223> complement - CH'1<br><220><br><221> misc_feature<br><222> (1251) ... (1668)<br><223> complement - C05\VH<br><220><br><221> misc_feature<br><222> (1669) ... (1719)<br><223> complement - leader<br><220><br><221> misc_feature<br><222> (1729) ... (1979)<br><223> complement - CMV\mp2<br><220><br><221> misc_feature<br><222> (1798) ... (2266)<br><223> Enhancer<br><220><br><221> misc_feature<br><222> (2267) ... (2392)<br><223> CMV\mp2 |

| SEQ ID NO: (containing free text) | Free text under <223> |
|---|---|
| 14 | <220><br><221> CDS<br><222> (2509) . . . (2841)<br><223> FI6\VL<br><220><br><221> CDS<br><222> (2842) . . . (3162)<br><223> CL<br><220><br><221> misc_feature<br><222> (3247) . . . (3306)<br><223> leader<br><220><br><221> CDS<br><222> (3307) . . . (3693)<br><223> FI6\VH<br><220><br><221> CDS<br><222> (3694) . . . (4014)<br><223> CH1<br><220><br><221> CDS<br><222> (4015) . . . (4683)<br><223> CH2-3<br><220><br><221> polyA_signal<br><222> (4690) . . . (4767)<br><223> TKpAshort<br><223> Plasmid encoding synthetic FI6 and 1A6 monoconals<br><220><br><221> polyA_signal<br><222> (191) . . . (239)<br><223> synthetic\polyA<br><220><br><221> misc_feature<br><222> (246) . . . (914)<br><223> complement - CH'2-3<br><220><br><221> misc_feature<br><222> (915) . . . (1235)<br><223> complement - CH'1<br><220><br><221> misc_feature<br><222> (1236) . . . (1598)<br><223> complement - 1A6\VH<br><220><br><221> misc_feature<br><222> (1599) . . . (1655)<br><223> complement - leader<br><220><br><221> misc_feature<br><222> (1665) . . . (1733)<br><223> complement - CMV\mp2<br><220><br><221> misc_feature<br><222> (1732) . . . (2202)<br><223> Enhancer<br><220><br><221> misc_feature<br><222> (2203) . . . (2328)<br><223> CMV\mp1<br><220><br><221> misc_feature<br><222> (2388) . . . (2444)<br><223> leader<br><220><br><221> misc_feature<br><222> (2445) . . . (2789)<br><223> KGL<br><220><br><221> CDS<br><222> (2784) . . . (3104)<br><223> CL |

| SEQ ID NO: (containing free text) | Free text under <223> |
|---|---|
| 19 | <220><br><221> misc_feature<br><222> (3189) . . . (3248)<br><223> leader<br><220><br><221> CDS<br><222> (3249) . . . (3635)<br><223> FI6\VH<br><220><br><221> CDS<br><222> (3636) . . . (3956)<br><223> CH1<br><220><br><221> CDS<br><222> (3957) . . . (4625)<br><223> CH2-3<br><220><br><221> polyA_signal<br><222> (4632) . . . (4709)<br><223> TKpAshort<br><223> Plasmid carrying FI6 and CR8033 monoclonals<br><220><br><221> polyA_signal<br><222> (173) . . . (221)<br><223> synthetic\polyA<br><220><br><221> misc_feature<br><222> (228) . . . (896)<br><223> complement - CH'2-3<br><220><br><221> misc_feature<br><222> (897) . . . (1217)<br><223> complement - CH'1<br><220><br><221> misc_feature<br><222> (1218) . . . (1604)<br><223> complement - CR8033\VH<br><220><br><221> misc_feature<br><222> (1605) . . . (1655)<br><223> complement - leader<br><220><br><221> misc_feature<br><222> (1665) . . . (1733)<br><223> complement - CMV\mp2<br><220><br><221> misc_feature<br><222> (1734) . . . (2202)<br><223> Enhancer<br><220><br><221> misc_feature<br><222> (2203) . . . (2328)<br><223> CMV\mp1<br><220><br><221> misc_feature<br><222> (2445) . . . (2789)<br><223> KGL<br><220><br><221> CDS<br><222> (2784) . . . (3104)<br><223> CL<br><220><br><221> misc_feature<br><222> (3189) . . . (3248)<br><223> leader<br><220><br><221> CDS<br><222> (3249) . . . (3635)<br><223> FI6\VH<br><220><br><221> CDS<br><222> (3636) . . . (3956)<br><223> CH1 |

| SEQ ID NO: (containing free text) | Free text under <223> |
|---|---|
| 24 | <220><br><221> CDS<br><222> (3957)...(4625)<br><223> CH2-3<br><220><br><221> misc_feature<br><222> (3968)...(3968)<br><223> A -> T<br><220><br><221> polyA_signal<br><222> (4632)...(4709)<br><223> TKpAshort<br><220><br><223> Plasmid carrying FI6 and CR8033 monoclonal antibodies<br><220><br><221> polyA_signal<br><222> (191)...(239)<br><223> synthetic polyA<br><220><br><221> misc_feature<br><222> (246)...(914)<br><223> complement - CH'2-3<br><220><br><221> misc_feature<br><222> (915)...(1235)<br><223> complement - CH'1<br><220><br><221> misc_feature<br><222> (1236)...(1622)<br><223> complement - CR8033\VH<br><220><br><221> misc_feature<br><222> (1623)...(1673)<br><223> complement - leader<br><220><br><221> misc_feature<br><222> (1683)...(1751)<br><223> CMV\mp2<br><220><br><221> misc_feature<br><222> (1752)...(2220)<br><223> Enhancer<br><220><br><221> misc_feature<br><222> (2221)...(2346)<br><223> CMV\mp1<br><220><br><221> misc_feature<br><222> (2406)...(2462)<br><223> leader<br><220><br><221> CDS<br><222> (2463)...(2795)<br><223> FI6\VL<br><220><br><221> CDS<br><222> (2796)...(3116)<br><223> CL<br><220><br><221> misc_feature<br><222> (3201)...(3260)<br><223> leader<br><220><br><221> CDS<br><222> (3261)...(3647)<br><223> FI6\VH<br><220><br><221> CDS<br><222> (3648)...(3968)<br><223> CH1<br><220><br><221> CDS<br><222> (3969)...(4637)<br><223> CH2-3 |
| 30 | <220><br><221> misc_feature<br><222> (3980)...(3980)<br><223> A -> T<br><220><br><221> polyA_signal<br><222> (4644)...(4721)<br><223> TKpAshort<br><223> EcoRV<br><220><br><221> polyA_signal<br><222> (201)...(252)<br><223> complement - synthetic\polyA<br><220><br><221> misc_feature<br><222> (268)...(588)<br><223> complement - CL<br><220><br><221> misc_feature<br><222> (589)...(909)<br><223> complement - TCN032\VL<br><220><br><221> polyA_signal<br><222> (910)...(966)<br><223> complement - leader<br><220><br><221> misc_feature<br><222> (1026)...(1094)<br><223> complement - CMV\mp2<br><220><br><221> misc_feature<br><222> (1095)...(1563)<br><223> Enhancer<br><220><br><221> misc_feature<br><222> (1564)...(1689)<br><223> CMV\mp1<br><220><br><221> misc_feature<br><222> (1749)...(1805)<br><223> leader<br><220><br><221> CDS<br><222> (1806)...(2165)<br><223> TCN032\VH<br><220><br><221> CDS<br><222> (2166)...(2459)<br><223> CH1<br><220><br><221> misc_feature<br><222> (2460)...(3152)<br><223> hinge-CH2'—CH3'<br><220><br><221> misc_feature<br><222> (3239)...(3296)<br><223> leader<br><220><br><221> CDS<br><222> (3297)...(3683)<br><223> FI6\VH<br><220><br><221> CDS<br><222> (3684)...(4004)<br><223> CH1<br><220><br><221> CDS<br><222> (4005)...(4673)<br><223> CH2-3<br><220><br><221> polyA_signal<br><222> (4693)...(4770)<br><223> TKpAshort |
| 36 | <223> FI6 and CO5 immunoadhesins |

| SEQ ID NO: (containing free text) | Free text under <223> |
|---|---|
| | <220> <221> polyA_signal <222> (201) . . . (432) <223> complement - SV40\polyA <220> <221> misc_feature <222> (453) . . . (1121) <223> complement - CH'2-3 <220> <221> misc_feature <222> (1125) . . . (1457) <223> complement - C05\VL <220> <221> misc_feature <222> (1458) . . . (1502) <223> SL\from\3bn201co <220> <221> misc_feature <222> (1503) . . . (1916) <223> complement - C05\VH <220> <221> misc_feature <222> (1965) . . . (1973) <223> leader <220> <221> misc_feature <222> (2371) . . . (2412) <223> complement - CMV\mp2 <220> <221> misc_feature <222> (2413) . . . (2881) <223> enhancer <220> <221> misc_feature <222> (2882) . . . (3007) <223> CMV\mp1 <220> <221> misc_feature <222> (3067) . . . (3055) <223> leader <220> <221> CDS <222> (3124) . . . (3510) <223> FI6\VH <220> <221> misc_feature <222> (3511) . . . (3555) <223> SL\from\3bn201co <220> <221> CDS <222> (3556) . . . (3888) <223> FI6\VL <220> <221> CDS <222> (3892) . . . (4560) <223> CH2-3 <220> <221> polyA_signal <222> (4581) . . . (4812) <223> SV40\polyA |
| 40 | <223> FI6 and CR8033 immunoadhesins <220> <221> polyA_signal <222> (201) . . . (432) <223> complement - SV40\polyA <220> <221> misc_feature <222> (453) . . . (1121) <223> complement - CH'2-3 <220> <221> misc_feature <222> (1125) . . . (1460) <223> complement - 033\VL |

| SEQ ID NO: (containing free text) | Free text under <223> |
|---|---|
| | <220> <221> misc_feature <222> (1461) . . . (1505) <223> SL\from\3bn201co <220> <221> misc_feature <222> (1506) . . . (1886) <223> complement - 033\VH <220> <221> misc_feature <222> (1935) . . . (1946) <223> complement - leader <220> <221> misc_feature <222> (2341) . . . (2382) <223> complement - CMV\mp2 <220> <221> misc_feature <222> (2383) . . . (2851) <223> enhancer <220> <221> misc_feature <222> (2852) . . . (2977) <223> CMV\mp1 <220> <221> misc_feature <222> (3073) . . . (3045) <223> leader <220> <221> CDS <222> (3094) . . . (3480) <223> FI6\VH <220> <221> misc_feature <222> (3481) . . . (3525) <223> SL\from\3bn201co <220> <221> CDS <222> (3526) . . . (3858) <223> FI6\VL <220> <221> misc_feature <222> (3862) . . . (4530) <223> CH2-3 <220> <221> polyA_signal <222> (4551) . . . (4782) <223> SV40\polyA |
| 43 | <223> Plasmid carrying TCN032 and Fi6 monoclonal antibodies <220> <221> repeat_region <222> (14) . . . (143) <220> <221> polyA_signal <222> (204) . . . (252) <223> synthetic polyA <220> <221> misc_feature <222> (261) . . . (267) <223> stop cassette (complement) <220> <221> misc_feature <222> (268) . . . (588) <223> constant light (on complementary strand) <220> <221> misc_feature <222> (967) . . . (971) <223> Kozak (located on complementary strand) <220> <221> misc_feature <222> (972) . . . (1019) <223> c-myc 5' UTR (located on complementary strand) |

| SEQ ID NO:<br>(containing free text) | Free text under <223> |
|---|---|
| | <220><br><221> misc_feature<br><222> (1026) ... (1094)<br><223> CMV\mp2<br><220><br><221> enhancer<br><222> (1026) ... (1094)<br><220><br><221> misc_feature<br><222> (1564) ... (1689)<br><220><br><221> misc_feature<br><222> (1696) ... (1743)<br><223> c-myc 5' UTR<br><220><br><221> misc_feature<br><222> (1744) ... (1748)<br><223> Kozak<br><220><br><221> misc_feature<br><222> (1749) ... (1805)<br><223> leader<br><220><br><221> CDS<br><222> (1806) ... (2165)<br><223> TCN032 variable heavy<br><220><br><221> repeat_region<br><222> (1845) ... (4974)<br><223> inverted terminal repeat<br><220><br><221> repeat_region<br><222> (1845) ... (4974)<br><223> inverted terminal repeat<br>(located on complement)<br><220><br><221> CDS<br><222> (2166) ... (2459)<br><223> CH1<br><220><br><221> misc<br><222> (2166) ... (2459)<br><223> CH1<br><220><br><221> CDS<br><222> (2460) ... (3152)<br><223> hinge-CH2'—CH3'<br><220><br><221> misc_feature<br><222> (3153) ... (3164)<br><223> furin cleavage site<br><220><br><221> misc_feature<br><222> (3165) ... (3236)<br><223> F2A linker<br><220><br><221> misc_feature<br><222> (3239) ... (3296) |

| SEQ ID NO:<br>(containing free text) | Free text under <223> |
|---|---|
| | <220><br><221> misc_feature<br><222> (3239) ... (3296)<br><220><br><221> CDS<br><222> (3297) ... (3683)<br><223> FI6 VH<br><220><br><221> CDS<br><222> (3684) ... (4004)<br><223> CH1<br><220><br><221> CDS<br><222> (4005) ... (4673)<br><223> CH2-3<br><220><br><221> misc_feature<br><222> (4674) ... (4680)<br><223> Stop cassette<br><220><br><221> misc_feature<br><222> (4674) ... (4680)<br><220><br><221> polyA_signal<br><222> (4693) ... (4770)<br><223> TKpAshort<br><220><br><221> rep_origin<br><222> (5151) ... (5606)<br><220><br><221> CDS<br><222> (5737) ... (6594)<br><223> Amp-R<br><220><br><221> misc_feature<br><222> (6768) ... (.7356)<br><223> col\E1\origin |

This application contains sequences and a sequence listing, which is hereby incorporated by reference. All publications, patents, and patent applications cited in this application, and U.S. Provisional Patent Application No. 61/992,649, filed May 13, 2014, the priority of which is claimed, are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

The invention claimed is:

1. A recombinant adeno-associated virus (AAV) having an AAV capsid and packaged therein a heterologous nucleic acid which expresses at least two functional monospecific antibodies in a cell, wherein the recombinant AAV comprises:
a 5' AAV inverted terminal repeat (ITR);
a first expression cassette which encodes at least a first open reading frame (ORF) for a first immunoglobulin under the control of regulatory control sequences which direct expression thereof;
a second expression cassette which comprises a second ORF, a linker, and a third ORF under the control of regulatory control sequences which direct expression thereof, wherein the second and third ORF are for a second and third immunoglobulin construct; and
a 3' AAV ITR.

2. The recombinant AAV according to claim 1, wherein the recombinant AAV further expresses a bispecific antibody.

3. The recombinant AAV according to claim 1, wherein the recombinant AAV comprises a bidirectional enhancer located between the first expression cassette and the second expression cassette.

4. The recombinant AAV according to claim 1, wherein the first ORF encodes an immunoglobulin light chain, the second ORF encodes a first immunoglobulin heavy chain and third ORF encodes a second heavy chain, whereby the expressed functional antibody constructs have two different heavy chains with different specificities which share a light chain.

5. The recombinant AAV according to claim 1, wherein at least one of the second and third ORF contain modified Fc coding sequences.

6. The recombinant AAV according to claim 1, wherein the linker in the second cassette comprises a linker selected from an IRES or an F2A.

7. The recombinant AAV according to claim 1, wherein the regulatory control sequences for the first expression cassette and/or the second cassette comprise a minimal promoter.

8. The recombinant AAV according to claim 1, wherein the regulatory control sequences for the first expression cassette and/or the second expression cassette comprise a minimal or synthetic polyA.

9. The recombinant AAV according to claim 1, wherein the first expression cassette is bicistronic and comprises a further ORF.

10. The recombinant AAV according to claim 9, wherein each of the ORF comprise an scFv.

11. The recombinant AAV according claim 1, wherein the vector comprises a bidirectional polyA between the first expression cassette and the second expression cassette.

12. The recombinant AAV according to claim 10, wherein the first expression cassette comprises an enhancer and a minimal promoter.

13. The recombinant AAV according to claim 12, wherein the second expression cassette comprises an enhancer and a minimal promoter.

14. The recombinant AAV according to claim 8, wherein the first and second expression cassettes together express two Fabs.

15. The recombinant AAV according to claim 1, wherein the at least two antibody constructs have different specificities.

16. The recombinant AAV according to claim 1, wherein the at least two antibody constructs are independently selected from a monoclonal antibody, an immunoadhesin, a Fab, a bifunctional antibody, and combinations thereof.

17. A recombinant adeno-associated virus (AAV) having an AAV capsid and packaged therein a heterologous nucleic acid which expresses at least two functional monospecific antibodies in a cell, wherein the recombinant AAV expresses a first monoclonal antibody having a first specificity, a second monoclonal antibody having a specificity different from the first monoclonal antibody, and a bifunctional antibody, and wherein the recombinant AAV comprises:
a 5' AAV inverted terminal repeat (ITR);
a first expression cassette which encodes at least a first open reading frame (ORF) for a first immunoglobulin under the control of regulatory control sequences which direct expression thereof;
a second expression cassette which comprises a second ORF, a linker, and a third ORF under the control of regulatory control sequences which direct expression thereof, wherein the second and third ORF are for a second and third immunoglobulin construct; and
a 3' AAV ITR.

18. A pharmaceutical composition comprising a recombinant AAV according to claim 1 and pharmaceutically acceptable carrier.

19. A method of delivering at least two functional antibodies to a subject, said method comprising administering a recombinant AAV according to claim 1 to the subject.

20. The recombinant AAV according to claim 17, wherein the recombinant AAV comprises a bidirectional enhancer located between the first expression cassette and the second expression cassette.

21. The recombinant AAV according to claim 17, wherein the first ORF encodes an immunoglobulin light chain, the second ORF encodes a first immunoglobulin heavy chain and third ORF encodes a second heavy chain, whereby the expressed functional antibody constructs have two different heavy chains with different specificities which share a light chain.

* * * * *

SEQUENCE LISTING

```
<160> NUMBER OF SEQ ID NOS: 50

<210> SEQ ID NO 1
<211> LENGTH: 705
<212> TYPE: DNA
<213> ORGANISM: Artificial sequence
<220> FEATURE:
<223> OTHER INFORMATION: Synthetic sequence encoding FI6 heavy chain
<220> FEATURE:
<221> NAME/KEY: CDS
<222> LOCATION: (1)..(705)
<223> OTHER INFORMATION: FI6 constant
```

<400> SEQUENCE: 1

```
gcg gcg cct aag agc tgc gac aag acc cac acc tgt ccc ccc tgc cct      48
Ala Ala Pro Lys Ser Cys Asp Lys Thr His Thr Cys Pro Pro Cys Pro
1               5                   10                  15 gcc cct gaa ctg ctg gga ggc ccc agc gtg ttc ctg ttc ccc cca aag      96
Ala Pro Glu Leu Leu Gly Gly Pro Ser Val Phe Leu Phe Pro Pro Lys
            20                  25                  30 ccc aag gac acc ctg atg atc agc cgg acc ccc gaa gtg acc tgc gtg     144
Pro Lys Asp Thr Leu Met Ile Ser Arg Thr Pro Glu Val Thr Cys Val
        35                  40                  45 gtg gtg gac gtg tcc cac gag gac cct gaa gtg aag ttc aat tgg tac     192
Val Val Asp Val Ser His Glu Asp Pro Glu Val Lys Phe Asn Trp Tyr
    50                  55                  60 gtg gac ggc gtg gaa gtg cac aac gcc aag acc aag ccc aga gag gaa     240
Val Asp Gly Val Glu Val His Asn Ala Lys Thr Lys Pro Arg Glu Glu
65                  70                  75                  80 cag tac aac agc acc tac cgg gtg gtg tcc gtg ctg acc gtg ctg cac     288
Gln Tyr Asn Ser Thr Tyr Arg Val Val Ser Val Leu Thr Val Leu His
                85                  90                  95 cag gac tgg ctg aac ggc aaa gag tac aag tgc aag gtg tcc aac aag     336
Gln Asp Trp Leu Asn Gly Lys Glu Tyr Lys Cys Lys Val Ser Asn Lys
            100                 105                 110 gcc ctg cct gcc ccc atc gag aaa acc atc agc aag gcc aag ggc cag     384
Ala Leu Pro Ala Pro Ile Glu Lys Thr Ile Ser Lys Ala Lys Gly Gln
        115                 120                 125 ccc cgc gag cct cag gtg tgc aca ctg ccc ccc agc cgg gaa gag atg     432
Pro Arg Glu Pro Gln Val Cys Thr Leu Pro Pro Ser Arg Glu Glu Met
    130                 135                 140 acc aag aac cag gtg tcc ctg acc tgc ctg gtc aag ggc ttc tac ccc     480
Thr Lys Asn Gln Val Ser Leu Thr Cys Leu Val Lys Gly Phe Tyr Pro
145                 150                 155                 160 agc gat atc gcc gtg gaa tgg gag agc aac ggc cag ccc gag aac aac     528
Ser Asp Ile Ala Val Glu Trp Glu Ser Asn Gly Gln Pro Glu Asn Asn
                165                 170                 175 tac aag acc acc ccc cct gtg ctg gac agc gac ggc tca ttc ttc ctg     576
Tyr Lys Thr Thr Pro Pro Val Leu Asp Ser Asp Gly Ser Phe Phe Leu
            180                 185                 190 tac agc aag ctg acc gtg gac aag agc cgg tgg cag cag ggc aac gtg     624
Tyr Ser Lys Leu Thr Val Asp Lys Ser Arg Trp Gln Gln Gly Asn Val
        195                 200                 205 ttc agc tgc agc gtg atg cac gag gcc ctg cac aac cac tac acc cag     672
Phe Ser Cys Ser Val Met His Glu Ala Leu His Asn His Tyr Thr Gln
    210                 215                 220 aag tcc ctg agc ctg agc ccc ggc aag tga tga                         705
Lys Ser Leu Ser Leu Ser Pro Gly Lys
225                 230
```

<210> SEQ ID NO 2
<211> LENGTH: 233
<212> TYPE: PRT
<213> ORGANISM: Artificial sequence
<220> FEATURE:
<223> OTHER INFORMATION: Synthetic Construct

<400> SEQUENCE: 2

```
Ala Ala Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30
```

```
Pro Lys Asp Thr Leu Met Ile Ser Arg Thr Pro Glu Val Thr Cys Val
         35                  40                  45
Val Val Asp Val Ser His Glu Asp Pro Glu Val Lys Phe Asn Trp Tyr
 50                  55                  60
Val Asp Gly Val Glu Val His Asn Ala Lys Thr Lys Pro Arg Glu Glu
 65                  70                  75                  80
Gln Tyr Asn Ser Thr Tyr Arg Val Val Ser Val Leu Thr Val Leu His
                 85                  90                  95
Gln Asp Trp Leu Asn Gly Lys Glu Tyr Lys Cys Lys Val Ser Asn Lys
            100                 105                 110
Ala Leu Pro Ala Pro Ile Glu Lys Thr Ile Ser Lys Ala Lys Gly Gln
        115                 120                 125
Pro Arg Glu Pro Gln Val Cys Thr Leu Pro Pro Ser Arg Glu Glu Met
130                 135                 140
Thr Lys Asn Gln Val Ser Leu Thr Cys Leu Val Lys Gly Phe Tyr Pro
145                 150                 155                 160
Ser Asp Ile Ala Val Glu Trp Glu Ser Asn Gly Gln Pro Glu Asn Asn
                165                 170                 175
Tyr Lys Thr Thr Pro Pro Val Leu Asp Ser Asp Gly Ser Phe Phe Leu
            180                 185                 190
Tyr Ser Lys Leu Thr Val Asp Lys Ser Arg Trp Gln Gln Gly Asn Val
        195                 200                 205
Phe Ser Cys Ser Val Met His Glu Ala Leu His Asn His Tyr Thr Gln
210                 215                 220
Lys Ser Leu Ser Leu Ser Pro Gly Lys
225                 230

<210> SEQ ID NO 3
<211> LENGTH: 7722
<212> TYPE: DNA
<213> ORGANISM: Artificial sequence
<220> FEATURE:
<223> OTHER INFORMATION: plasmid carrying FI6 and 1A6 antibodies
<220> FEATURE:
<221> NAME/KEY: polyA_signal
<222> LOCATION: (191)..(239)
<223> OTHER INFORMATION: synthetic\polyA
<220> FEATURE:
<221> NAME/KEY: misc_feature
<222> LOCATION: (246)..(914)
<223> OTHER INFORMATION: complement - CH'2-3
<220> FEATURE:
<221> NAME/KEY: misc_feature
<222> LOCATION: (915)..(1235)
<223> OTHER INFORMATION: complement - CH'1
<220> FEATURE:
<221> NAME/KEY: misc_feature
<222> LOCATION: (1236)..(1598)
<223> OTHER INFORMATION: complement - 1A6\VH
<220> FEATURE:
<221> NAME/KEY: misc_feature
<222> LOCATION: (1599)..(1655)
<223> OTHER INFORMATION: complement - leader
<220> FEATURE:
<221> NAME/KEY: misc_feature
<222> LOCATION: (1734)..(2202)
<223> OTHER INFORMATION: Enhancer
<220> FEATURE:
<221> NAME/KEY: misc_feature
<222> LOCATION: (2388)..(2444)
<223> OTHER INFORMATION: leader
<220> FEATURE:
<221> NAME/KEY: CDS
<222> LOCATION: (2445)..(2777)
<223> OTHER INFORMATION: FI6\VL
```

```
<220> FEATURE:
<221> NAME/KEY: misc_feature
<222> LOCATION: (3183)..(3242)
<223> OTHER INFORMATION: leader
<220> FEATURE:
<221> NAME/KEY: CDS
<222> LOCATION: (3243)..(3629)
<223> OTHER INFORMATION: FI6\VH
<220> FEATURE:
<221> NAME/KEY: CDS
<222> LOCATION: (3630)..(3950)
<223> OTHER INFORMATION: CH1
<220> FEATURE:
<221> NAME/KEY: CDS
<222> LOCATION: (3951)..(4619)
<223> OTHER INFORMATION: CH2-3
<220> FEATURE:
<221> NAME/KEY: polyA_signal
<222> LOCATION: (4626)..(4703)
<223> OTHER INFORMATION: TKpAshort
<220> FEATURE:
<221> NAME/KEY: misc_feature
<222> LOCATION: (6995)..(7283)
<223> OTHER INFORMATION: COL\E1\Origin

<400> SEQUENCE: 3
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gccatgctct     180
aggaagatct cacacaaaaa accaacacac agatgtaatg aaaataaaga tattttattt     240
tatcacttcc cggggctcag gctcaggggac ttctgggtgt agtggttgtg cagggcctcg     300
tgcatcacgc tgcagctgaa cacgttgccc tgctgccacc ggctcttgtc cacggtcagc     360
ttgctataca ggaagaatga gccgtcgctg tccagcacag gggggtggt cttgtagttg      420 ttctcgggct ggccgttgct ctcccattcc acggcgatct cgctggggta gaagcccttg     480
accaggcagg tcaggacac ctggttcttg gtcatctctt cccggctggg gggcagtgtg     540
tagacctgag gctcgcgggg ctggcccttg gccttgctga tggttttctc gatggggca      600 ggcagggcct tgttggacac cttgcacttg tactctttgc cgttcagcca gtcctggtgc     660
agcacggtca gcacggacac cacccggtag gtgctgttgt actgttcctc tctgggcttg     720
gtcttggcgt tgtgcacttc cacgccgtcc acgtaccaat tgaacttcac ttcagggtcc     780
tcgtgggaca cgtccaccac cacgcaggtc acttcggggg tccggctgat catcaggtg     840 tccttgggct ttggggggaa caggaacacg ctggggcctc ccagcagttc aggggcaggg     900
caggggggac acgtgtgggt cttgtcgcag ctcttaggtt ccacccgctt gtccaccttg     960
gtgttgctgg gcttgtggtt cacgttgcag atgtaggtct gggtgcccag gctgctgctg    1020
ggcacggtga ccacgctgct caggctatac aggccgctgc tctgcagcac ggctggaaag    1080
gtgtgcacgc cgctggtcag ggcgccagag ttccaggaca cggtcacggg ctcggggaag    1140
tagtccttga ccaggcagcc cagggcggct gttccgccag aggtgctctt gctgctaggg    1200
gccagaggga acacgcttgg tcccttggtg ctggcgctcg agacggtcac cagggttccc    1260
tgtccccagt aatccattcc tccgctggcg attccgctcc gatccttggc gcagtagtac    1320
acggcggtat cctcggcccg caggctgttc atctgcaggt acagggtgtt cttgctgttg    1380
gcccggctga tggtgaaccg tcccttcacg ctatcggcgt agtacttgtt gtttccatcg    1440
tagctgatca cggccacccca ctccagtccc tttcctgggg cctgccgcac ccagtgcatt    1500
ccgtaatcgc tgaaggtgaa tccgctggcg gcgcagctca gccgcaggct ccgtcctggc    1560
```

```
tgcaccactc ctcctccgct ctcctgcagc tgcacctgtg aattcgtcac cagggccagg      1620
ctcagggcga tcagcagcag cagctgcatg cgcatggtgg cggcgcgatc tgacggttca      1680
ctaaacgagc tctgcttata taggcctccc accgtacacg ccacctcgac atacctagtt     1740
attaatagta atcaattacg gggtcattag ttcatagccc atatatggag ttccgcgtta     1800
cataacttac ggtaaatggc ccgcctggct gaccgcccaa cgaccccgc ccattgacgt       1860 caataatgac gtatgttccc atagtaacgc caatagggac tttccattga cgtcaatggg     1920
tggagtattt acggtaaact gcccacttgg cagtacatca agtgtatcat atgccaagta     1980
cgccccctat tgacgtcaat gacggtaaat ggcccgcctg gcattatgcc cagtacatga     2040
ccttatggga ctttcctact tggcagtaca tctacgtatt agtcatcgct attaccatgg     2100
tgatgcggtt ttggcagtac atcaatgggc gtggatagcg gtttgactca cggggatttc     2160
caagtctcca ccccattgac gtcaatggga gtttgttttg gcaccaaaat caacgggact     2220
ttccaaaatg tcgtaacaac tccgccccat tgacgcaaat gggcggtagg cgtgtacggt     2280
gggaggtcta tataagcaga gctggtttag tgaaccgtca gatccgctgg gcactttgca     2340
ctggaactta caacacccga gcaaggacgc gactctgccg ccccaccatg cgcatgcagc     2400
tgctgctgct gatcgccctg agcctggccc tggtgaccaa cagc gat atc gtc atg       2456
                                                Asp Ile Val Met
                                                  1 acc cag agc cca gat agc ctg gcc gtg agc ctg gga gag cgg gcc acc       2504
Thr Gln Ser Pro Asp Ser Leu Ala Val Ser Leu Gly Glu Arg Ala Thr
 5              10                  15                  20 atc aac tgc aag agc agc cag agc gtg acc ttc aac tac aag aac tac       2552
Ile Asn Cys Lys Ser Ser Gln Ser Val Thr Phe Asn Tyr Lys Asn Tyr
             25                  30                  35 ctg gcc tgg tac cag cag aag cca gga cag cca cca aag ctg ctg atc       2600
Leu Ala Trp Tyr Gln Gln Lys Pro Gly Gln Pro Pro Lys Leu Leu Ile
         40                  45                  50 tac tgg gcc agc acc cgg gag agc gga gtg cca gat cgg ttc agc gga       2648
Tyr Trp Ala Ser Thr Arg Glu Ser Gly Val Pro Asp Arg Phe Ser Gly
     55                  60                  65 agc gga agc gga acc gat ttc acc ctg acc atc agc agc ctg cag gcc       2696
Ser Gly Ser Gly Thr Asp Phe Thr Leu Thr Ile Ser Ser Leu Gln Ala
 70                  75                  80 gag gat gtg gcc gtg tac tac tgc cag cag cac tac cgg acc cca cca       2744
Glu Asp Val Ala Val Tyr Tyr Cys Gln Gln His Tyr Arg Thr Pro Pro
85                  90                  95                 100 acc ttc gga cag gga acc aag gtg gag atc aag cgtacggtgg ccgccccaag    2797
Thr Phe Gly Gln Gly Thr Lys Val Glu Ile Lys
                105                 110 cgtgttcatc ttcccaccaa gcgatgagca gctgaagagc ggaaccgcca gcgtggtgtg     2857
cctgctgaac aacttctacc cacgggaggc caaggtgcag tggaaggtgg ataacgccct     2917
gcagagcgga aacagccagg agagcgtgac cgagcaggat agcaaggata gcacctacag     2977
cctgagcagc accctgaccc tgagcaaggc cgattacgag aagcacaagg tgtacgcctg     3037
cgaggtgacc caccagggac tgagcagccc agtgaccaag agcttcaacc gcggagagtg     3097
ccggaagcgg cgggccccag tgaagcagac cctgaacttc gatctgctga gctggccgga     3157
agatgtggag agcaacccag accaatgta cagaatgcag ctgctgagct gcatcgccct      3217
gagcctggcc ctggtgacca acagc cag gtg caa cta gtg gag agc gga gga       3269
                                Gln Val Gln Leu Val Glu Ser Gly Gly
                                              115                 120 gga gtg gtg cag cca gga cgg agc ctg cgg ctg agc tgc gcc gcc agc       3317
```

```
Gly Val Val Gln Pro Gly Arg Ser Leu Arg Leu Ser Cys Ala Ala Ser
            125                 130                 135 gga ttc acc ttc agc acc tac gcc atg cac tgg gtg cgg cag gcc cca      3365
Gly Phe Thr Phe Ser Thr Tyr Ala Met His Trp Val Arg Gln Ala Pro
        140                 145                 150 gga aag gga ctg gag tgg gtg gcc gtg atc agc tac gat gcc aac tac      3413
Gly Lys Gly Leu Glu Trp Val Ala Val Ile Ser Tyr Asp Ala Asn Tyr
            155                 160                 165 aag tac tac gcc gat agc gtg aag gga cgg ttc acc atc agc cgg gat      3461
Lys Tyr Tyr Ala Asp Ser Val Lys Gly Arg Phe Thr Ile Ser Arg Asp
        170                 175                 180 aac agc aag aac acc ctg tac ctg cag atg aac agc ctg cgg gcc gag      3509
Asn Ser Lys Asn Thr Leu Tyr Leu Gln Met Asn Ser Leu Arg Ala Glu
185                 190                 195                 200 gat acc gcc gtg tac tac tgc gcc aag gat agc cag ctg cgg agc ctg      3557
Asp Thr Ala Val Tyr Tyr Cys Ala Lys Asp Ser Gln Leu Arg Ser Leu
                205                 210                 215 ctg tac ttc gag tgg ctg agc cag gga tac ttc gat tac tgg gga cag      3605
Leu Tyr Phe Glu Trp Leu Ser Gln Gly Tyr Phe Asp Tyr Trp Gly Gln
            220                 225                 230 gga acc ctg gtg acc gtg agc agc gct agc acc aag gga cca agc gtg      3653
Gly Thr Leu Val Thr Val Ser Ser Ala Ser Thr Lys Gly Pro Ser Val
        235                 240                 245 ttc cca ctg gcc cca agc agc aag agc acc agc gga gga acc gcc gcc      3701
Phe Pro Leu Ala Pro Ser Ser Lys Ser Thr Ser Gly Gly Thr Ala Ala
250                 255                 260 ctg gga tgc ctg gtg aag gat tac ttc cca gag cca gtg acc gtg agc      3749
Leu Gly Cys Leu Val Lys Asp Tyr Phe Pro Glu Pro Val Thr Val Ser
265                 270                 275                 280 tgg aac agc gga gcc ctg acc agc gga gtg cac acc ttc cca gcc gtg      3797
Trp Asn Ser Gly Ala Leu Thr Ser Gly Val His Thr Phe Pro Ala Val
                285                 290                 295 ctg cag agc agc gga ctg tat agc ctg agc agc gtg gtg acc gtg cca      3845
Leu Gln Ser Ser Gly Leu Tyr Ser Leu Ser Ser Val Val Thr Val Pro
            300                 305                 310 agc agc agc ctg gga acc cag acc tac atc tgc aac gtg aac cac aag      3893
Ser Ser Ser Leu Gly Thr Gln Thr Tyr Ile Cys Asn Val Asn His Lys
        315                 320                 325 cca agc aac acc aag gtg gat aag aag gtg gag cca aag agc tgc gat      3941
Pro Ser Asn Thr Lys Val Asp Lys Lys Val Glu Pro Lys Ser Cys Asp
330                 335                 340 aag acc cac acg tgc cct cct tgt cca gcc ccc gaa ctg ctg ggc ggg      3989
Lys Thr His Thr Cys Pro Pro Cys Pro Ala Pro Glu Leu Leu Gly Gly
345                 350                 355                 360 cct agc gtg ttc ctg ttt ccc cct aag cct aaa gat aca ctg atg att      4037
Pro Ser Val Phe Leu Phe Pro Pro Lys Pro Lys Asp Thr Leu Met Ile
                365                 370                 375 agt aga acc cca gag gtc aca tgc gtg gtc gtg gac gtg tcc cac gaa      4085
Ser Arg Thr Pro Glu Val Thr Cys Val Val Val Asp Val Ser His Glu
            380                 385                 390 gag cct gac gtg aag ttc aac tgg tac gtg gat ggc gtg gag gtg cac      4133
Glu Pro Asp Val Lys Phe Asn Trp Tyr Val Asp Gly Val Glu Val His
        395                 400                 405 aat gct aag act aaa cca cgc gaa gag cag tat aat agt aca tac cga      4181
Asn Ala Lys Thr Lys Pro Arg Glu Glu Gln Tyr Asn Ser Thr Tyr Arg
410                 415                 420 gtc gtg tca gtc ctg aca gtg ctg cac cag gat tgg ctg aac ggc aag      4229
Val Val Ser Val Leu Thr Val Leu His Gln Asp Trp Leu Asn Gly Lys
425                 430                 435                 440
```

```
gag tat aag tgc aag gtg tct aac aag gcc ctg ccc gcc cct atc gag   4277
Glu Tyr Lys Cys Lys Val Ser Asn Lys Ala Leu Pro Ala Pro Ile Glu
            445                 450                 455 aaa aca att agc aag gcc aaa ggg cag cca cgg gaa ccc cag gtc tac   4325
Lys Thr Ile Ser Lys Ala Lys Gly Gln Pro Arg Glu Pro Gln Val Tyr
        460                 465                 470 act ctg cca ccc tca aga gat gaa ctg act aag aac cag gtc agc ctg   4373
Thr Leu Pro Pro Ser Arg Asp Glu Leu Thr Lys Asn Gln Val Ser Leu
    475                 480                 485 acc tgt ctg gtg aaa ggc ttc tac ccc agc gac atc gcc gtg gag tgg   4421
Thr Cys Leu Val Lys Gly Phe Tyr Pro Ser Asp Ile Ala Val Glu Trp
490                 495                 500 gaa agt aac ggc cag cct gag aat aac tac aag act acc cct cca gtg   4469
Glu Ser Asn Gly Gln Pro Glu Asn Asn Tyr Lys Thr Thr Pro Pro Val
505                 510                 515                 520 ctg gat agc gac ggg tcc ttc ttc ctg tat agc aag ctg aca gtg gac   4517
Leu Asp Ser Asp Gly Ser Phe Phe Leu Tyr Ser Lys Leu Thr Val Asp
                        525                 530                 535 aaa tcc cgc tgg cag cag gga aac gtc ttt tcc tgt tct gtg atg cat   4565
Lys Ser Arg Trp Gln Gln Gly Asn Val Phe Ser Cys Ser Val Met His
                540                 545                 550 gag gcc ctg cac aat cat tac acc cag aag agt ctg tca ctg agc ccc   4613
Glu Ala Leu His Asn His Tyr Thr Gln Lys Ser Leu Ser Leu Ser Pro
            555                 560                 565 ggc aaa tgataaaagg aacccgcgct atgacggcaa taaaaagaca gaataaaacc    4669
Gly Lys
    570 cacgggtgtt gggtcgtttg ttcataaacc cgggatcgat aaggatcttc ctagagcatg 4729 gctacgtaga taagtagcat ggcgggttaa tcattaacta caaggaaccc ctagtgatgg 4789 agttggccac tccctctctg cgcgctcgct cgctcactga ggccgggcga ccaaaggtcg 4849 cccgacgccc gggctttgcc cgggcggcct cagtgagcga gcgagcgcgc agccttaatt 4909 aacctaattc actggccgtc gttttacaac gtcgtgactg ggaaaaccct ggcgttaccc 4969 aacttaatcg ccttgcagca catccccctt tcgccagctg gcgtaatagc gaagaggccc 5029 gcaccgatcg cccttcccaa cagttgcgca gcctgaatgg cgaatgggac gcgccctgta 5089 gcggcgcatt aagcgcggcg ggtgtggtgg ttacgcgcag cgtgaccgct acacttgcca 5149 gcgccctagc gcccgctcct ttcgctttct tcccttcctt tctcgccacg ttcgccggct 5209 ttccccgtca gctctaaatc ggggggctcc ctttagggtt ccgatttagt gctttacggc 5269 acctcgaccc caaaaaactt gattagggtg atggttcacg tagtgggcca tcgccctgat 5329 agacggtttt tcgccctttg acgttggagt ccacgttctt taatagtgga ctcttgttcc 5389 aaactggaac aacactcaac cctatctcgg tctattcttt tgatttataa gggattttgc 5449 cgatttcggc ctattggtta aaaaatgagc tgatttaaca aaaatttaac gcgaatttta 5509 acaaaatatt aacgcttaca atttaggtgg cactttttcgg ggaaatgtgc gcggaacccc 5569 tatttgttta ttttttctaaa tacattcaaa tatgtatccg ctcatgagac aataaccctg 5629 ataaatgctt caataatatt gaaaaaggaa gagtatgagt attcaacatt tccgtgtcgc 5689 ccttattccc ttttttgcgg cattttgcct tcctgttttt gctcacccag aaacgctggt 5749 gaaagtaaaa gatgctgaag atcagttggg tgcacgagtg ggttacatcg aactggatct 5809 caacagcggt aagatccttg agagttttcg ccccgaagaa cgttttccaa tgatgagcac 5869 ttttaaagtt ctgctatgtg gcgcggtatt atcccgtatt gacgccgggc aagagcaact 5929 cggtcgccgc atacactatt ctcagaatga cttggttgag tactcaccag tcacagaaaa 5989
```

```
gcatcttacg gatggcatga cagtaagaga attatgcagt gctgccataa ccatgagtga      6049
taacactgcg gccaacttac ttctgacaac gatcggagga ccgaaggagc taaccgcttt      6109
tttgcacaac atgggggatc atgtaactcg ccttgatcgt tgggaaccgg agctgaatga      6169
agccatacca aacgacgagc gtgacaccac gatgcctgta gcaatggcaa caacgttgcg      6229
caaactatta actggcgaac tacttactct agcttcccgg caacaattaa tagactggat      6289
ggaggcggat aaagttgcag gaccacttct gcgctcggcc cttccggctg ctggtttat       6349 tgctgataaa tctggagccg gtgagcgtgg gtctcgcggt atcattgcag cactggggcc      6409
agatggtaag ccctcccgta tcgtagttat ctacacgacg gggagtcagg caactatgga      6469
tgaacgaaat agacagatcg ctgagatagg tgcctcactg attaagcatt ggtaactgtc      6529
agaccaagtt tactcatata ctttagat tgatttaaaa cttcattttt aatttaaaag       6589
gatctaggtg aagatccttt ttgataatct catgaccaaa atcccttaac gtgagttttc      6649
gttccactga gcgtcagacc ccgtagaaaa gatcaaagga tcttcttgag atcctttttt      6709
tctgcgcgta atctgctgct tgcaaacaaa aaaaccaccg ctaccagcgg tggtttgttt      6769
gccggatcaa gagctaccaa ctcttttttcc gaaggtaact ggcttcagca gagcgcagat     6829
accaaatact gttcttctag tgtagccgta gttaggccac cacttcaaga actctgtagc     6889
accgcctaca tacctcgctc tgctaatcct gttaccagtg ctgctgcca gtggcgataa      6949 gtcgtgtctt accgggttgg actcaagacg atagttaccg gataaggcgc agcggtcggg     7009
ctgaacgggg ggttcgtgca cacagcccag cttggagcga acgacctaca ccgaactgag     7069
atacctacag cgtgagctat gagaaagcgc cacgcttccc gaagggagaa aggcggacag     7129
gtatccggta gcggcagggt cggaacagga gagcgcacg agggagcttc caggggaaa       7189 cgcctggtat ctttatagtc ctgtcgggtt tcgccacctc tgacttgagc gtcgattttt     7249
gtgatgctcg tcagggggc ggagcctatg gaaaaacgcc agcaacgcgg ccttttacg       7309 gttcctggcc ttttgctggc cttttgctca catgttcttt cctgcgttat ccctgattc      7369 tgtggataac cgtattaccg cctttgagtg agctgatacc gctcgccgca gccgaacgac     7429
cgagcgcagc gagtcagtga gcgaggaagc ggaagagcgc ccaatacgca aaccgcctct     7489
ccccgcgcgt tggccgattc attaatgcag ctggcacgac aggtttcccg actggaaagc     7549
gggcagtgag cgcaacgcaa ttaatgtgag ttagctcact cattaggcac cccaggcttt     7609
acactttatg cttccggctc gtatgttgtg tggaattgtg agcggataac aatttcacac     7669
aggaaacagc tatgaccatg attacgccag atttaattaa ggccttaatt agg            7722
```

<210> SEQ ID NO 4
<211> LENGTH: 111
<212> TYPE: PRT
<213> ORGANISM: Artificial sequence
<220> FEATURE:
<223> OTHER INFORMATION: Synthetic Construct

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp

```
                    50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                     85                  90                  95

Arg Thr Pro Pro Thr Phe Gly Gln Gly Thr Lys Val Glu Ile Lys
                100                 105                 110

<210> SEQ ID NO 5
<211> LENGTH: 129
<212> TYPE: PRT
<213> ORGANISM: Artificial sequence
<220> FEATURE:
<223> OTHER INFORMATION: Synthetic Construct

<400> SEQUENCE: 5

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Thr Tyr
                 20                  25                  30

Ala Met His Trp Val Arg Gln Ala Pro Gly Lys Gly Leu Glu Trp Val
             35                  40                  45

Ala Val Ile Ser Tyr Asp Ala Asn Tyr Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Gln Leu Arg Ser Leu Leu Tyr Phe Glu Trp Leu Ser
                100                 105                 110

Gln Gly Tyr Phe Asp Tyr Trp Gly Gln Gly Thr Leu Val Thr Val Ser
            115                 120                 125

Ser

<210> SEQ ID NO 6
<211> LENGTH: 107
<212> TYPE: PRT
<213> ORGANISM: Artificial sequence
<220> FEATURE:
<223> OTHER INFORMATION: Synthetic Construct

<400> SEQUENCE: 6

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His
                100                 105
```

-continued

```
<210> SEQ ID NO 7
<211> LENGTH: 223
<212> TYPE: PRT
<213> ORGANISM: Artificial sequence
<220> FEATURE:
<223> OTHER INFORMATION: Synthetic Construct

<400> SEQUENCE: 7

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Glu Pro Asp
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 8
<211> LENGTH: 7773
<212> TYPE: DNA
<213> ORGANISM: Artificial sequence
<220> FEATURE:
<223> OTHER INFORMATION: Plasmid encoding FI6 and C05 monoclonal
      antibodies
<220> FEATURE:
<221> NAME/KEY: polyA_signal
<222> LOCATION: (204)..(252)
<223> OTHER INFORMATION: synthetic\polyA
<220> FEATURE:
<221> NAME/KEY: misc_feature
<222> LOCATION: (259)..(927)
<223> OTHER INFORMATION: complement - CH'2-3
<220> FEATURE:
<221> NAME/KEY: misc_feature
<222> LOCATION: (928)..(1248)
<223> OTHER INFORMATION: complement - CH'1
<220> FEATURE:
<221> NAME/KEY: misc_feature
<222> LOCATION: (1251)..(1668)
<223> OTHER INFORMATION: complement - C05\VH
<220> FEATURE:
<221> NAME/KEY: misc_feature
<222> LOCATION: (1669)..(1719)
<223> OTHER INFORMATION: complement - leader
```

```
<220> FEATURE:
<221> NAME/KEY: misc_feature
<222> LOCATION: (1729)..(1979)
<223> OTHER INFORMATION: complement - CMV\mp2
<220> FEATURE:
<221> NAME/KEY: misc_feature
<222> LOCATION: (1798)..(2266)
<223> OTHER INFORMATION: Enhancer
<220> FEATURE:
<221> NAME/KEY: misc_feature
<222> LOCATION: (2267)..(2392)
<223> OTHER INFORMATION: CMV\mp2
<220> FEATURE:
<221> NAME/KEY: CDS
<222> LOCATION: (2509)..(2841)
<223> OTHER INFORMATION: FI6\VL
<220> FEATURE:
<221> NAME/KEY: CDS
<222> LOCATION: (2842)..(3162)
<223> OTHER INFORMATION: CL
<220> FEATURE:
<221> NAME/KEY: misc_feature
<222> LOCATION: (3247)..(3306)
<223> OTHER INFORMATION: leader
<220> FEATURE:
<221> NAME/KEY: CDS
<222> LOCATION: (3307)..(3693)
<223> OTHER INFORMATION: FI6\VH
<220> FEATURE:
<221> NAME/KEY: CDS
<222> LOCATION: (3694)..(4014)
<223> OTHER INFORMATION: CH1
<220> FEATURE:
<221> NAME/KEY: CDS
<222> LOCATION: (4015)..(4683)
<223> OTHER INFORMATION: CH2-3
<220> FEATURE:
<221> NAME/KEY: polyA_signal
<222> LOCATION: (4690)..(4767)
<223> OTHER INFORMATION: TKpAshort

<400> SEQUENCE: 8
ggccttaatt aggctgcgcg ctcgctcgct cactgaggcc gcccgggcaa agcccgggcg    60
tcgggcgacc tttggtcgcc cggcctcagt gagcgagcga gcgcgcagag agggagtggc   120
caactccatc actaggggtt ccttgtagtt aatgattaac ccgccatgct acttatctac   180
gtagccatgc tctaggaaga tctcacacaa aaaaccaaca cacagatgta atgaaaataa   240 agatattta ttttatcact tcccggggct caggctcagg gacttctggg tgtagtggtt   300
gtgcagggcc tcgtgcatca cgctgcagct gaacacgttg ccctgctgcc accggctctt   360
gtccacggtc agcttgctat acaggaagaa tgagccgtcg ctgtccagca caggggggt   420 ggtcttgtag ttgttctcgg gctggccgtt gctctcccat tccacggcga tctcgctggg   480
gtagaagccc ttgaccaggc aggtcaggga cacctggttc ttggtcatct cttcccggct   540 gggggggcagt gtgtagacct gaggctcgcg ggctggccc ttggccttgc tgatggtttt   600
ctcgatgggg gcaggcaggg ccttgttgga caccttgcac ttgtactctt gccgttcag   660 ccagtcctgg tgcagcacgg tcagcacgga caccacccgg taggtgctgt tgtactgttc   720
ctctctgggc ttggtcttgg cgttgtgcac ttccacgccg tccacgtacc aattgaactt   780
cacttcaggg tcctcgtggg acacgtccac caccacgcag gtcacttcgg gggtccggct   840
gatcatcagg gtgtccttgg gctttggggg gaacaggaac acgctgggc ctcccagcag   900 ttcaggggca gggcagggg gacacgtgtg gtcttgtcg cagctcttag gttccacccg   960
cttgtccacc ttggtgttgc tgggcttgtg gttcacgttg cagatgtagg tctgggtgcc  1020
caggctgctg ctgggcacgg tgaccacgct gctcaggcta tacaggccgc tgctctgcag  1080
```

```
cacggctgga aaggtgtgca cgccgctggt cagggcgcca gagttccagg acacggtcac    1140
gggctcgggg aagtagtcct tgaccaggca gcccagggcg gctgttccgc cagaggtgct    1200
cttgctgcta ggggccagag gaacacgct tggtcccttg gtgctggcgc tcgagacggt    1260
caccagggtt ccctgtcccc acacatcgaa ggcatctccc accagatcgg cccgctccca    1320
tccggcgctc accacctgct gcatggacat gtgcttggcg cagtagtaca ctccggtatc    1380
ctccacccgc aggttggtca tctgcaggta cagggtctcc ttgctgttat cccggctgat    1440
ggtgaaccgt ccctccacgc tatcggcgta atcaatgtct cctcctccgg cgttgatgat    1500
gctcagccac tccagtccct ttcctggggc ctgccgcacc cagctcacgg cgtagtagct    1560
cagggtgctc tctccgaagc tgcttccgct tcccacgcag ctcagccgca ggctctctcc    1620
tggctgcacc agtcctcctc cgctctcctg cagctgcacc tgtgaattcg tcaccagggc    1680
caggctcagg gcgatcagca gcagcagctg catgcgcatg gtggcggcgc gatctgacgg    1740
ttcactaaac gagctctgct tatataggcc tcccaccgta cacgccacct cgacatacct    1800
agttattaat agtaatcaat tacggggtca ttagttcata gcccatatat ggagttccgc    1860
gttacataac ttacggtaaa tggcccgcct ggctgaccgc ccaacgaccc ccgcccattg    1920
acgtcaataa tgacgtatgt tcccatagta acgccaatag ggactttcca ttgacgtcaa    1980
tgggtggagt atttacggta aactgcccac ttggcagtac atcaagtgta tcatatgcca    2040
agtacgcccc ctattgacgt caatgacggt aaatggcccg cctggcatta tgcccagtac    2100
atgaccttat gggactttcc tacttggcag tacatctacg tattagtcat cgctattacc    2160
atggtgatgc ggttttggca gtacatcaat gggcgtggat agcggtttga ctcacgggga    2220
tttccaagtc tccaccccat tgacgtcaat gggagtttgt tttggcacca aaatcaacgg    2280
gactttccaa aatgtcgtaa caactccgcc ccattgacgc aaatgggcgg taggcgtgta    2340
cggtgggagg tctatataag cagagctggt ttagtgaacc gtcagatccg ctgggcactt    2400
tgcactggaa cttacaacac ccgagcaagg acgcgactct gccgcccac catgcgcatg    2460 cagctgctgc tgctgatcgc cctgagcctg gccctggtga ccaacagc gat atc gtc    2517
                                                        Asp Ile Val
                                                          1 atg acc cag agc cca gat agc ctg gcc gtg agc ctg gga gag cgg gcc    2565
Met Thr Gln Ser Pro Asp Ser Leu Ala Val Ser Leu Gly Glu Arg Ala
 5                  10                  15 acc atc aac tgc aag agc agc cag agc gtg acc ttc aac tac aag aac    2613
Thr Ile Asn Cys Lys Ser Ser Gln Ser Val Thr Phe Asn Tyr Lys Asn
 20                  25                  30                  35 tac ctg gcc tgg tac cag cag aag cca gga cag cca cca aag ctg ctg    2661
Tyr Leu Ala Trp Tyr Gln Gln Lys Pro Gly Gln Pro Pro Lys Leu Leu
             40                  45                  50 atc tac tgg gcc agc acc cgg gag agc gga gtg cca gat cgg ttc agc    2709
Ile Tyr Trp Ala Ser Thr Arg Glu Ser Gly Val Pro Asp Arg Phe Ser
         55                  60                  65 gga agc gga agc gga acc gat ttc acc ctg acc atc agc agc ctg cag    2757
Gly Ser Gly Ser Gly Thr Asp Phe Thr Leu Thr Ile Ser Ser Leu Gln
     70                  75                  80 gcc gag gat gtg gcc gtg tac tac tgc cag cag cac tac cgg acc cca    2805
Ala Glu Asp Val Ala Val Tyr Tyr Cys Gln Gln His Tyr Arg Thr Pro
 85                  90                  95 cca acc ttc gga cag gga acc aag gtg gag atc aag cgt acg gtg gcc    2853
Pro Thr Phe Gly Gln Gly Thr Lys Val Glu Ile Lys Arg Thr Val Ala
100                 105                 110                 115 gcc cca agc gtg ttc atc ttc cca cca agc gat gag cag ctg aag agc    2901
```

-continued

| | | | | | | | | | | | | |
|---|---|---|---|---|---|---|---|---|---|---|---|---|
| Ala | Pro | Ser | Val | Phe | Ile | Phe | Pro | Pro | Ser | Asp | Glu | Gln | Leu | Lys | Ser |
| | | | 120 | | | | | 125 | | | | | 130 | | |

```
gga acc gcc agc gtg gtg tgc ctg ctg aac aac ttc tac cca cgg gag      2949
Gly Thr Ala Ser Val Val Cys Leu Leu Asn Asn Phe Tyr Pro Arg Glu
            135                 140                 145 gcc aag gtg cag tgg aag gtg gat aac gcc ctg cag agc gga aac agc      2997
Ala Lys Val Gln Trp Lys Val Asp Asn Ala Leu Gln Ser Gly Asn Ser
        150                 155                 160 cag gag agc gtg acc gag cag gat agc aag gat agc acc tac agc ctg      3045
Gln Glu Ser Val Thr Glu Gln Asp Ser Lys Asp Ser Thr Tyr Ser Leu
    165                 170                 175 agc agc acc ctg acc ctg agc aag gcc gat tac gag aag cac aag gtg      3093
Ser Ser Thr Leu Thr Leu Ser Lys Ala Asp Tyr Glu Lys His Lys Val
180                 185                 190                 195 tac gcc tgc gag gtg acc cac cag gga ctg agc agc cca gtg acc aag      3141
Tyr Ala Cys Glu Val Thr His Gln Gly Leu Ser Ser Pro Val Thr Lys
                200                 205                 210 agc ttc aac cgc gga gag tgc cggaagcggc gggccccagt gaagcagacc         3192
Ser Phe Asn Arg Gly Glu Cys
                215 ctgaacttcg atctgctgaa gctggccgga gatgtggaga gcaacccagg accaatgtac    3252 agaatgcagc tgctgagctg catcgccctg agcctggccc tggtgaccaa cagc cag      3309
                                                          Gln gtg caa cta gtg gag agc gga gga gga gtg gtg cag cca gga cgg agc      3357
Val Gln Leu Val Glu Ser Gly Gly Gly Val Val Gln Pro Gly Arg Ser
220                 225                 230                 235 ctg cgg ctg agc tgc gcc gcc agc gga ttc acc ttc agc acc tac gcc      3405
Leu Arg Leu Ser Cys Ala Ala Ser Gly Phe Thr Phe Ser Thr Tyr Ala
                240                 245                 250 atg cac tgg gtg cgg cag gcc cca gga aag gga ctg gag tgg gtg gcc      3453
Met His Trp Val Arg Gln Ala Pro Gly Lys Gly Leu Glu Trp Val Ala
            255                 260                 265 gtg atc agc tac gat gcc aac tac aag tac tac gcc gat agc gtg aag      3501
Val Ile Ser Tyr Asp Ala Asn Tyr Lys Tyr Tyr Ala Asp Ser Val Lys
        270                 275                 280 gga cgg ttc acc atc agc cgg gat aac agc aag aac acc ctg tac ctg      3549
Gly Arg Phe Thr Ile Ser Arg Asp Asn Ser Lys Asn Thr Leu Tyr Leu
    285                 290                 295 cag atg aac agc ctg cgg gcc gag gat acc gcc gtg tac tac tgc gcc      3597
Gln Met Asn Ser Leu Arg Ala Glu Asp Thr Ala Val Tyr Tyr Cys Ala
300                 305                 310                 315 aag gat agc cag ctg cgg agc ctg ctg tac ttc gag tgg ctg agc cag      3645
Lys Asp Ser Gln Leu Arg Ser Leu Leu Tyr Phe Glu Trp Leu Ser Gln
                320                 325                 330 gga tac ttc gat tac tgg gga cag gga acc ctg gtg acc gtg agc agc      3693
Gly Tyr Phe Asp Tyr Trp Gly Gln Gly Thr Leu Val Thr Val Ser Ser
            335                 340                 345 gct agc acc aag gga cca agc gtg ttc cca ctg gcc cca agc agc aag      3741
Ala Ser Thr Lys Gly Pro Ser Val Phe Pro Leu Ala Pro Ser Ser Lys
        350                 355                 360 agc acc agc gga gga acc gcc gcc ctg gga tgc ctg gtg aag gat tac      3789
Ser Thr Ser Gly Gly Thr Ala Ala Leu Gly Cys Leu Val Lys Asp Tyr
    365                 370                 375 ttc cca gag cca gtg acc gtg agc tgg aac agc gga gcc ctg acc agc      3837
Phe Pro Glu Pro Val Thr Val Ser Trp Asn Ser Gly Ala Leu Thr Ser
380                 385                 390                 395 gga gtg cac acc ttc cca gcc gtg ctg cag agc agc gga ctg tat agc      3885
Gly Val His Thr Phe Pro Ala Val Leu Gln Ser Ser Gly Leu Tyr Ser
                400                 405                 410
```

-continued

```
ctg agc agc gtg gtg acc gtg cca agc agc agc ctg gga acc cag acc      3933
Leu Ser Ser Val Val Thr Val Pro Ser Ser Ser Leu Gly Thr Gln Thr
            415                 420                 425 tac atc tgc aac gtg aac cac aag cca agc aac acc aag gtg gat aag      3981
Tyr Ile Cys Asn Val Asn His Lys Pro Ser Asn Thr Lys Val Asp Lys
        430                 435                 440 aag gtg gag cca aag agc tgc gat aag acc cac acg tgc cct cca tgt      4029
Lys Val Glu Pro Lys Ser Cys Asp Lys Thr His Thr Cys Pro Pro Cys
    445                 450                 455 cca gcc ccc gaa ctg ctg ggc ggg cct agc gtg ttc ctg ttt ccc cct      4077
Pro Ala Pro Glu Leu Leu Gly Gly Pro Ser Val Phe Leu Phe Pro Pro
460                 465                 470                 475 aag cct aaa gat aca ctg atg att agt aga acc cca gag gtc aca tgc      4125
Lys Pro Lys Asp Thr Leu Met Ile Ser Arg Thr Pro Glu Val Thr Cys
                480                 485                 490 gtg gtc gtg gac gtg tcc cac gaa gag cct gac gtg aag ttc aac tgg      4173
Val Val Val Asp Val Ser His Glu Glu Pro Asp Val Lys Phe Asn Trp
            495                 500                 505 tac gtg gat ggc gtg gag gtg cac aat gct aag act aaa cca cgc gaa      4221
Tyr Val Asp Gly Val Glu Val His Asn Ala Lys Thr Lys Pro Arg Glu
        510                 515                 520 gag cag tat aat agt aca tac cga gtc gtg tca gtc ctg aca gtg ctg      4269
Glu Gln Tyr Asn Ser Thr Tyr Arg Val Val Ser Val Leu Thr Val Leu
    525                 530                 535 cac cag gat tgg ctg aac ggc aag gag tat aag tgc aag gtg tct aac      4317
His Gln Asp Trp Leu Asn Gly Lys Glu Tyr Lys Cys Lys Val Ser Asn
540                 545                 550                 555 aag gcc ctg ccc gcc cct atc gag aaa aca att agc aag gcc aaa ggg      4365
Lys Ala Leu Pro Ala Pro Ile Glu Lys Thr Ile Ser Lys Ala Lys Gly
                560                 565                 570 cag cca cgg gaa ccc cag gtc tac act ctg cca ccc tca aga gat gaa      4413
Gln Pro Arg Glu Pro Gln Val Tyr Thr Leu Pro Pro Ser Arg Asp Glu
            575                 580                 585 ctg act aag aac cag gtc agc ctg acc tgt ctg gtg aaa ggc ttc tac      4461
Leu Thr Lys Asn Gln Val Ser Leu Thr Cys Leu Val Lys Gly Phe Tyr
        590                 595                 600 ccc agc gac atc gcc gtg gag tgg gaa agt aac ggc cag cct gag aat      4509
Pro Ser Asp Ile Ala Val Glu Trp Glu Ser Asn Gly Gln Pro Glu Asn
605                 610                 615 aac tac aag act acc cct cca gtg ctg gat agc gac ggg tcc ttc ttc      4557
Asn Tyr Lys Thr Thr Pro Pro Val Leu Asp Ser Asp Gly Ser Phe Phe
620                 625                 630                 635 ctg tat agc aag ctg aca gtg gac aaa tcc cgc tgg cag cag gga aac      4605
Leu Tyr Ser Lys Leu Thr Val Asp Lys Ser Arg Trp Gln Gln Gly Asn
                640                 645                 650 gtc ttt tcc tgt tct gtg atg cat gag gcc ctg cac aat cat tac acc      4653
Val Phe Ser Cys Ser Val Met His Glu Ala Leu His Asn His Tyr Thr
            655                 660                 665 cag aag agt ctg tca ctg agc ccc ggc aaa tgataaaagg aacccgcgct        4703
Gln Lys Ser Leu Ser Leu Ser Pro Gly Lys
        670                 675 atgacggcaa taaaaagaca gaataaaacc cacgggtgtt gggtcgtttg ttcataaacc    4763
cgggatcgat aaggatcttc ctagagcatg gctacgtaga taagtagcat ggcgggttaa    4823
tcattaacta caaggaaccc ctagtgatgg agttggccac tccctctctg cgcgctcgct    4883
cgctcactga ggccgggcga ccaaaggtcg cccgacgccc gggctttgcc cgggcggcct    4943
cagtgagcga gcgagcgcgc agccttaatt aacctaattc actggccgtc gttttacaac    5003
```

```
gtcgtgactg ggaaaaccct ggcgttaccc aacttaatcg ccttgcagca catccccctt    5063
tcgccagctg gcgtaatagc gaagaggccc gcaccgatcg cccttcccaa cagttgcgca    5123
gcctgaatgg cgaatgggac gcgccctgta gcggcgcatt aagcgcggcg ggtgtggtgg    5183
ttacgcgcag cgtgaccgct acacttgcca gcgccctagc gcccgctcct ttcgctttct    5243
tcccttcctt tctcgccacg ttcgccggct ttccccgtca agctctaaat cgggggctcc    5303
ctttagggtt ccgatttagt gctttacggc acctcgaccc caaaaaactt gattagggtg    5363
atggttcacg tagtgggcca tcgccctgat agacggtttt tcgccctttg acgttggagt    5423
ccacgttctt taatagtgga ctcttgttcc aaactggaac aacactcaac cctatctcgg    5483
tctattcttt tgatttataa gggattttgc cgatttcggc ctattggtta aaaatgagc     5543 tgatttaaca aaaatttaac gcgaatttta acaaaatatt aacgcttaca atttaggtgg    5603 cactttcgg ggaaatgtgc gcggaacccc tatttgttta ttttctaaa tacattcaaa      5663 tatgtatccg ctcatgagac aataaccctg ataaatgctt caataatatt gaaaaggaa     5723 gagtatgagt attcaacatt tccgtgtcgc ccttattccc ttttttgcgg cattttgcct    5783
tcctgttttt gctcacccag aaacgctggt gaaagtaaaa gatgctgaag atcagttggg    5843
tgcacgagtg gttacatcg aactggatct caacagcggt aagatccttg agagttttcg     5903
ccccgaagaa cgttttccaa tgatgagcac ttttaaagtt ctgctatgtg gcgcggtatt    5963
atcccgtatt gacgccgggc aagagcaact cggtcgccgc atacactatt ctcagaatga    6023
cttggttgag tactcaccag tcacagaaaa gcatcttacg gatggcatga cagtaagaga    6083
attatgcagt gctgccataa ccatgagtga taacactgcg ccaacttac ttctgacaac     6143 gatcggagga ccgaaggagc taaccgcttt tttgcacaac atgggggatc atgtaactcg    6203
ccttgatcgt tgggaaccgg agctgaatga agccatacca aacgacgagc gtgacaccac    6263
gatgcctgta gcaatggcaa caacgttgcg caaactatta actggcgaac tacttactct    6323
agcttcccgg caacaattaa tagactggat ggaggcggat aaagttgcag gaccacttct    6383
gcgctcggcc cttccggctg gctggtttat tgctgataaa tctggagccg gtgagcgtgg    6443
gtctcgcggt atcattgcag cactggggcc agatggtaag ccctcccgta tcgtagttat    6503
ctacacgacg gggagtcagg caactatgga tgaacgaaat agacagatcg ctgagatagg    6563
tgcctcactg attaagcatt ggtaactgtc agaccaagtt tactcatata ctttagat     6623 tgatttaaaa cttcattttt aatttaaaag gatctaggtg aagatccttt ttgataatct    6683
catgaccaaa atcccttaac gtgagttttc gttccactga gcgtcagacc ccgtagaaaa    6743
gatcaaagga tcttcttgag atcctttttt tctgcgcgta atctgctgct tgcaaacaaa    6803
aaaaccaccg ctaccagcgg tggtttgttt gccggatcaa gagctaccaa ctctttttcc    6863
gaaggtaact ggcttcagca gagcgcagat accaaatact gttcttctag tgtagccgta    6923
gttaggccac cacttcaaga actctgtagc accgcctaca tacctcgctc tgctaatcct    6983
gttaccagtg gctgctgcca gtggcgataa gtcgtgtctt accgggttgg actcaagacg    7043
atagttaccg gataaggcgc agcggtcggg ctgaacgggg ggttcgtgca cacagcccag    7103
cttggagcga acgacctaca ccgaactgag atacctacag cgtgagctat gagaaagcgc    7163
cacgcttccc gaagggagaa aggcggacag gtatccggta agcggcaggg tcggaacagg    7223
agagcgcacg agggagcttc caggggggaaa cgcctggtat ctttatagtc ctgtcgggtt    7283
tcgccacctc tgacttgagc gtcgattttt gtgatgctcg tcaggggggc ggagcctatg    7343
gaaaaacgcc agcaacgcgg cctttttacg gttcctggcc ttttgctggc cttttgctca    7403
```

```
catgttcttt cctgcgttat cccctgattc tgtggataac cgtattaccg cctttgagtg    7463
agctgatacc gctcgccgca gccgaacgac cgagcgcagc gagtcagtga gcgaggaagc    7523
ggaagagcgc ccaatacgca aaccgcctct ccccgcgcgt tggccgattc attaatgcag    7583
ctggcacgac aggtttcccg actggaaagc gggcagtgag cgcaacgcaa ttaatgtgag    7643
ttagctcact cattaggcac cccaggcttt acactttatg cttccggctc gtatgttgtg    7703
tggaattgtg agcggataac aatttcacac aggaaacagc tatgaccatg attacgccag    7763
atttaattaa                                                           7773
```

<210> SEQ ID NO 9
<211> LENGTH: 111
<212> TYPE: PRT
<213> ORGANISM: Artificial sequence
<220> FEATURE:
<223> OTHER INFORMATION: Synthetic Construct

<400> SEQUENCE: 9

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Thr Phe Asn
            20                  25                  30
Tyr Lys Asn Tyr Leu Ala Trp Tyr Gln Gln Lys Pro Gly Gln Pro Pro
        35                  40                  45
Lys Leu Leu Ile Tyr Trp Ala Ser Thr Arg Glu Ser Gly Val Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln Gln His Tyr
                85                  90                  95
Arg Thr Pro Pro Thr Phe Gly Gln Gly Thr Lys Val Glu Ile Lys
            100                 105                 110
```

<210> SEQ ID NO 10
<211> LENGTH: 107
<212> TYPE: PRT
<213> ORGANISM: Artificial sequence
<220> FEATURE:
<223> OTHER INFORMATION: Synthetic Construct

<400> SEQUENCE: 10

```
Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

<210> SEQ ID NO 11

```
<211> LENGTH: 129
<212> TYPE: PRT
<213> ORGANISM: Artificial sequence
<220> FEATURE:
<223> OTHER INFORMATION: Synthetic Construct

<400> SEQUENCE: 11
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser

```
<210> SEQ ID NO 12
<211> LENGTH: 107
<212> TYPE: PRT
<213> ORGANISM: Artificial sequence
<220> FEATURE:
<223> OTHER INFORMATION: Synthetic Construct

<400> SEQUENCE: 12
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

```
<210> SEQ ID NO 13
<211> LENGTH: 223
<212> TYPE: PRT
<213> ORGANISM: Artificial sequence
<220> FEATURE:
<223> OTHER INFORMATION: Synthetic Construct

<400> SEQUENCE: 13
```

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr

```
                     20                  25                  30
     Pro Glu Val Thr Cys Val Val Asp Val Ser His Glu Pro Asp
                 35                  40                  45

Val Lys Phe Asn Trp Tyr Val Asp Gly Val Glu Val His Asn Ala Lys
      50                  55                  60

Thr Lys Pro Arg Glu Glu Gln Tyr Asn Ser Thr Tyr Arg Val Val Ser
      65                  70                  75                  80

Val Leu Thr Val Leu His Gln Asp Trp Leu Asn Gly Lys Glu Tyr Lys
                         85                  90                  95

Cys Lys Val Ser Asn Lys Ala Leu Pro Ala Pro Ile Glu Lys Thr Ile
                    100                 105                 110

Ser Lys Ala Lys Gly Gln Pro Arg Glu Pro Gln Val Tyr Thr Leu Pro
                115                 120                 125

Pro Ser Arg Asp Glu Leu Thr Lys Asn Gln Val Ser Leu Thr Cys Leu
        130                 135                 140

Val Lys Gly Phe Tyr Pro Ser Asp Ile Ala Val Glu Trp Glu Ser Asn
     145                 150                 155                 160

Gly Gln Pro Glu Asn Asn Tyr Lys Thr Thr Pro Pro Val Leu Asp Ser
                     165                 170                 175

Asp Gly Ser Phe Phe Leu Tyr Ser Lys Leu Thr Val Asp Lys Ser Arg
                 180                 185                 190

Trp Gln Gln Gly Asn Val Phe Ser Cys Ser Val Met His Glu Ala Leu
             195                 200                 205

His Asn His Tyr Thr Gln Lys Ser Leu Ser Leu Ser Pro Gly Lys
         210                 215                 220

<210> SEQ ID NO 14
<211> LENGTH: 7728
<212> TYPE: DNA
<213> ORGANISM: Artificial sequence
<220> FEATURE:
<223> OTHER INFORMATION: Plasmid encoding synthetic FI6 and 1A6
      monoconals
<220> FEATURE:
<221> NAME/KEY: polyA_signal
<222> LOCATION: (191)..(239)
<223> OTHER INFORMATION: synthetic\polyA
<220> FEATURE:
<221> NAME/KEY: misc_feature
<222> LOCATION: (246)..(914)
<223> OTHER INFORMATION: complement - CH'2-3
<220> FEATURE:
<221> NAME/KEY: misc_feature
<222> LOCATION: (915)..(1235)
<223> OTHER INFORMATION: complement - CH'1
<220> FEATURE:
<221> NAME/KEY: misc_feature
<222> LOCATION: (1236)..(1598)
<223> OTHER INFORMATION: complement - 1A6\VH
<220> FEATURE:
<221> NAME/KEY: misc_feature
<222> LOCATION: (1599)..(1655)
<223> OTHER INFORMATION: complement - leader
<220> FEATURE:
<221> NAME/KEY: misc_feature
<222> LOCATION: (1665)..(1733)
<223> OTHER INFORMATION: complement - CMV\mp2
<220> FEATURE:
<221> NAME/KEY: misc_feature
<222> LOCATION: (1732)..(2202)
<223> OTHER INFORMATION: Enhancer
<220> FEATURE:
<221> NAME/KEY: misc_feature
<222> LOCATION: (2203)..(2328)
<223> OTHER INFORMATION: CMV\mp1
<220> FEATURE:
```

```
<221> NAME/KEY: misc_feature
<222> LOCATION: (2388)..(2444)
<223> OTHER INFORMATION: leader
<220> FEATURE:
<221> NAME/KEY: misc_feature
<222> LOCATION: (2445)..(2789)
<223> OTHER INFORMATION: KGL
<220> FEATURE:
<221> NAME/KEY: CDS
<222> LOCATION: (2784)..(3104)
<223> OTHER INFORMATION: CL
<220> FEATURE:
<221> NAME/KEY: misc_feature
<222> LOCATION: (3189)..(3248)
<223> OTHER INFORMATION: leader
<220> FEATURE:
<221> NAME/KEY: CDS
<222> LOCATION: (3249)..(3635)
<223> OTHER INFORMATION: FI6\VH
<220> FEATURE:
<221> NAME/KEY: CDS
<222> LOCATION: (3636)..(3956)
<223> OTHER INFORMATION: CH1
<220> FEATURE:
<221> NAME/KEY: CDS
<222> LOCATION: (3957)..(4625)
<223> OTHER INFORMATION: CH2-3
<220> FEATURE:
<221> NAME/KEY: polyA_signal
<222> LOCATION: (4632)..(4709)
<223> OTHER INFORMATION: TKpAshort

<400> SEQUENCE: 14
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctacgta gccatgctct   180
aggaagatct cacacaaaaa accaacacac agatgtaatg aaaataaaga tattttattt   240
tatcacttcc cggggctcag gctcagggac ttctgggtgt agtggttgtg cagggcctcg   300
tgcatcacgc tgcagctgaa cacgttgccc tgctgccacc ggctcttgtc cacggtcagc   360
ttgctataca ggaagaatga gccgtcgctg tccagcacag ggggggtggt cttgtagttg   420
ttctcgggct ggccgttgct ctcccattcc acggcgatct cgctgggta gaagcccttg    480 accaggcagg tcagggacac ctggttcttg gtcatctctt cccggctggg gggcagtgtg   540
tagacctgag gctcgcgggg ctggcccttg gccttgctga tggttttctc gatgggggca   600
ggcagggcct tgttggacac cttgcacttg tactctttgc cgttcagcca gtcctggtgc   660
agcacggtca gcacggacac caccgggtag gtgctgttgt actgttcctc tctgggcttg   720
gtcttggcgt tgtgcacttc cacgccgtcc acgtaccaat tgaacttcac ttcagggtcc   780
tcgtgggaca cgtccaccac cacgcaggtc acttcggggg tccggctgat catcagggtg   840
tccttgggct ttgggggggaa caggaacacg ctggggcctc ccagcagttc aggggcaggg   900
caggggggac acgtgtgggt cttgtcgcag ctcttaggtt ccacccgctt gtccaccttg   960
gtgttgctgg gcttgtggtt cacgttgcag atgtaggtct gggtgcccag gctgctgctg  1020
ggcacggtga ccacgctgct caggctatac aggccgctgc tctgcagcac ggctggaaag  1080
gtgtgcacgc cgctggtcag ggcgccgag ttccaggaca cggtcacggg ctcggggaag  1140
tagtccttga ccaggcagcc cagggcggct gttccgccag aggtgctctt gctgctaggg  1200
gccagaggga acacgcttgg tcccttggtg ctggcgctcg agacggtcac cagggttccc  1260
tgtccccagt aatccattcc tccgctgcg attccgctcc gatccttggc gcagtagtac  1320
acggcggtat cctcggcccg caggctgttc atctgcaggt acagggtgtt cttgctgttg  1380
```

-continued

```
gcccggctga tggtgaaccg tcccttcacg ctatcggcgt agtacttgtt gtttccatcg    1440
tagctgatca cggccaccca ctccagtccc tttcctgggg cctgccgcac ccagtgcatt    1500
ccgtaatcgc tgaaggtgaa tccgctggcg gcgcagctca gccgcaggct ccgtcctggc    1560
tgcaccactc ctcctccgct ctcctgcagc tgcacctgtg aattcgtcac cagggccagg    1620
ctcagggcga tcagcagcag cagctgcatg cgcatggtgg cggcgcgatc tgacggttca    1680
ctaaacgagc tctgcttata taggcctccc accgtacacg ccacctcgac atacctagtt    1740
attaatagta atcaattacg gggtcattag ttcatagccc atatatggag ttccgcgtta    1800
cataacttac ggtaaatggc ccgcctggct gaccgcccaa cgaccccgc ccattgacgt    1860 caataatgac gtatgttccc atagtaacgc caatagggac tttccattga cgtcaatggg    1920
tggagtattt acggtaaact gcccacttgg cagtacatca agtgtatcat atgccaagta    1980
cgccccctat tgacgtcaat gacggtaaat ggcccgcctg gcattatgcc cagtacatga    2040
ccttatggga ctttcctact tggcagtaca tctacgtatt agtcatcgct attaccatgg    2100
tgatgcggtt ttggcagtac atcaatgggc gtggatagcg gtttgactca cggggatttc    2160
caagtctcca ccccattgac gtcaatggga gtttgttttg gcaccaaaat caacgggact    2220
ttccaaaatg tcgtaacaac tccgcccat tgacgcaaat gggcggtagg cgtgtacggt    2280
gggaggtcta tataagcaga gctggtttag tgaaccgtca gatccgctgg cactttgca    2340 ctggaactta caacacccga gcaaggacgc gactctgccg ccccaccatg cgcatgcagc    2400
tgctgctgct gatcgccctg agcctggccc tggtgaccaa cagcgatatc gtcatgaccc    2460
agagcccaga tagcctggcc gtgagcctgg agagcgggc caccatcaac tgcaagagca    2520
gccagagcgt gctgtacagc agcaacaaca gaaactacct ggcctggtac agcagaagc    2580 caggacagcc accaaagctg ctgatctact gggccagcac ccgggagagc ggagtgccag    2640
atcggttcag cggaagcgga agcggaaccg atttcaccct gaccatcagc agcctgcagg    2700
ccgaggatgt ggccgtgtac tactgccagc agtactacag cacccactg accttcggac    2760 agggaaccaa ggtggagatc aag cgt acg gtg gcc gcc cca agc gtg ttc atc    2813
                          Arg Thr Val Ala Ala Pro Ser Val Phe Ile
                          1               5                  10 ttc cca cca agc gat gag cag ctg aag agc gga acc gcc agc gtg gtg    2861
Phe Pro Pro Ser Asp Glu Gln Leu Lys Ser Gly Thr Ala Ser Val Val
            15                  20                  25 tgc ctg ctg aac aac ttc tac cca cgg gag gcc aag gtg cag tgg aag    2909
Cys Leu Leu Asn Asn Phe Tyr Pro Arg Glu Ala Lys Val Gln Trp Lys
        30                  35                  40 gtg gat aac gcc ctg cag agc gga aac agc cag gag agc gtg acc gag    2957
Val Asp Asn Ala Leu Gln Ser Gly Asn Ser Gln Glu Ser Val Thr Glu
    45                  50                  55 cag gat agc aag gat agc acc tac agc ctg agc agc acc ctg acc ctg    3005
Gln Asp Ser Lys Asp Ser Thr Tyr Ser Leu Ser Ser Thr Leu Thr Leu
60                  65                  70 agc aag gcc gat tac gag aag cac aag gtg tac gcc tgc gag gtg acc    3053
Ser Lys Ala Asp Tyr Glu Lys His Lys Val Tyr Ala Cys Glu Val Thr
75                  80                  85                  90 cac cag gga ctg agc agc cca gtg acc aag agc ttc aac cgc gga gag    3101
His Gln Gly Leu Ser Ser Pro Val Thr Lys Ser Phe Asn Arg Gly Glu
                95                  100                 105 tgc cggaagcggc gggcccagt gaagcagacc ctgaacttcg atctgctgaa            3154
Cys gctggccgga gatgtggaga gcaacccagg accaatgtac agaatgcagc tgctgagctg    3214
```

-continued

```
catcgccctg agcctggccc tggtgaccaa cagc cag gtg caa cta gtg gag agc   3269
                                    Gln Val Gln Leu Val Glu Ser
                                                110 gga gga gga gtg gtg cag cca gga cgg agc ctg cgg ctg agc tgc gcc   3317
Gly Gly Gly Val Val Gln Pro Gly Arg Ser Leu Arg Leu Ser Cys Ala
115                 120                 125                 130 gcc agc gga ttc acc ttc agc acc tac gcc atg cac tgg gtg cgg cag   3365
Ala Ser Gly Phe Thr Phe Ser Thr Tyr Ala Met His Trp Val Arg Gln
                135                 140                 145 gcc cca gga aag gga ctg gag tgg gtg gcc gtg atc agc tac gat gcc   3413
Ala Pro Gly Lys Gly Leu Glu Trp Val Ala Val Ile Ser Tyr Asp Ala
            150                 155                 160 aac tac aag tac tac gcc gat agc gtg aag gga cgg ttc acc atc agc   3461
Asn Tyr Lys Tyr Tyr Ala Asp Ser Val Lys Gly Arg Phe Thr Ile Ser
        165                 170                 175 cgg gat aac agc aag aac acc ctg tac ctg cag atg aac agc ctg cgg   3509
Arg Asp Asn Ser Lys Asn Thr Leu Tyr Leu Gln Met Asn Ser Leu Arg
    180                 185                 190 gcc gag gat acc gcc gtg tac tac tgc gcc aag gat agc cag ctg cgg   3557
Ala Glu Asp Thr Ala Val Tyr Tyr Cys Ala Lys Asp Ser Gln Leu Arg
195                 200                 205                 210 agc ctg ctg tac ttc gag tgg ctg agc cag gga tac ttc gat tac tgg   3605
Ser Leu Leu Tyr Phe Glu Trp Leu Ser Gln Gly Tyr Phe Asp Tyr Trp
                215                 220                 225 gga cag gga acc ctg gtg acc gtg agc agc gct agc acc aag gga cca   3653
Gly Gln Gly Thr Leu Val Thr Val Ser Ser Ala Ser Thr Lys Gly Pro
            230                 235                 240 agc gtg ttc cca ctg gcc cca agc agc aag agc acc agc gga gga acc   3701
Ser Val Phe Pro Leu Ala Pro Ser Ser Lys Ser Thr Ser Gly Gly Thr
        245                 250                 255 gcc gcc ctg gga tgc ctg gtg aag gat tac ttc cca gag cca gtg acc   3749
Ala Ala Leu Gly Cys Leu Val Lys Asp Tyr Phe Pro Glu Pro Val Thr
    260                 265                 270 gtg agc tgg aac agc gga gcc ctg acc agc gga gtg cac acc ttc cca   3797
Val Ser Trp Asn Ser Gly Ala Leu Thr Ser Gly Val His Thr Phe Pro
275                 280                 285                 290 gcc gtg ctg cag agc agc gga ctg tat agc ctg agc agc gtg gtg acc   3845
Ala Val Leu Gln Ser Ser Gly Leu Tyr Ser Leu Ser Ser Val Val Thr
                295                 300                 305 gtg cca agc agc agc ctg gga acc cag acc tac atc tgc aac gtg aac   3893
Val Pro Ser Ser Ser Leu Gly Thr Gln Thr Tyr Ile Cys Asn Val Asn
            310                 315                 320 cac aag cca agc aac acc aag gtg gat aag aag gtg gag cca aag agc   3941
His Lys Pro Ser Asn Thr Lys Val Asp Lys Lys Val Glu Pro Lys Ser
        325                 330                 335 tgc gat aag acc cac acg tgc cct cct tgt cca gcc ccc gaa ctg ctg   3989
Cys Asp Lys Thr His Thr Cys Pro Pro Cys Pro Ala Pro Glu Leu Leu
    340                 345                 350 ggc ggg cct agc gtg ttc ctg ttt ccc cct aag cct aaa gat aca ctg   4037
Gly Gly Pro Ser Val Phe Leu Phe Pro Pro Lys Pro Lys Asp Thr Leu
355                 360                 365                 370 atg att agt aga acc cca gag gtc aca tgc gtg gtc gtg gac gtg tcc   4085
Met Ile Ser Arg Thr Pro Glu Val Thr Cys Val Val Val Asp Val Ser
                375                 380                 385 cac gaa gag cct gac gtg aag ttc aac tgg tac gtg gat ggc gtg gag   4133
His Glu Glu Pro Asp Val Lys Phe Asn Trp Tyr Val Asp Gly Val Glu
            390                 395                 400 gtg cac aat gct aag act aaa cca cgc gaa gag cag tat aat agt aca   4181
Val His Asn Ala Lys Thr Lys Pro Arg Glu Glu Gln Tyr Asn Ser Thr
```

```
                  405                 410                 415
tac cga gtc gtg tca gtc ctg aca gtg ctg cac cag gat tgg ctg aac       4229
Tyr Arg Val Val Ser Val Leu Thr Val Leu His Gln Asp Trp Leu Asn
    420                 425                 430 ggc aag gag tat aag tgc aag gtg tct aac aag gcc ctg ccc gcc cct       4277
Gly Lys Glu Tyr Lys Cys Lys Val Ser Asn Lys Ala Leu Pro Ala Pro
435                 440                 445                 450 atc gag aaa aca att agc aag gcc aaa ggg cag cca cgg gaa ccc cag       4325
Ile Glu Lys Thr Ile Ser Lys Ala Lys Gly Gln Pro Arg Glu Pro Gln
                    455                 460                 465 gtc tac act ctg cca ccc tca aga gat gaa ctg act aag aac cag gtc       4373
Val Tyr Thr Leu Pro Pro Ser Arg Asp Glu Leu Thr Lys Asn Gln Val
            470                 475                 480 agc ctg acc tgt ctg gtg aaa ggc ttc tac ccc agc gac atc gcc gtg       4421
Ser Leu Thr Cys Leu Val Lys Gly Phe Tyr Pro Ser Asp Ile Ala Val
485                 490                 495 gag tgg gaa agt aac ggc cag cct gag aat aac tac aag act acc cct       4469
Glu Trp Glu Ser Asn Gly Gln Pro Glu Asn Asn Tyr Lys Thr Thr Pro
    500                 505                 510 cca gtg ctg gat agc gac ggg tcc ttc ttc ctg tat agc aag ctg aca       4517
Pro Val Leu Asp Ser Asp Gly Ser Phe Phe Leu Tyr Ser Lys Leu Thr
515                 520                 525                 530 gtg gac aaa tcc cgc tgg cag cag gga aac gtc ttt tcc tgt tct gtg       4565
Val Asp Lys Ser Arg Trp Gln Gln Gly Asn Val Phe Ser Cys Ser Val
                    535                 540                 545 atg cat gag gcc ctg cac aat cat tac acc cag aag agt ctg tca ctg       4613
Met His Glu Ala Leu His Asn His Tyr Thr Gln Lys Ser Leu Ser Leu
            550                 555                 560 agc ccc ggc aaa tgataaaagg aacccgcgct atgacggcaa taaaaagaca           4665
Ser Pro Gly Lys
            565 gaataaaaacc cacgggtgtt gggtcgtttg ttcataaacc cgggatcgat aaggatcttc    4725
ctagagcatg gctacgtaga taagtagcat ggcgggttaa tcattaacta caaggaaccc    4785
ctagtgatgg agttggccac tccctctctg cgcgctcgct cgctcactga ggccgggcga    4845
ccaaaggtcg cccgacgccc gggctttgcc cgggcggcct cagtgagcga gcgagcgcgc    4905
agccttaatt aacctaattc actggccgtc gttttacaac gtcgtgactg ggaaaaccct    4965
ggcgttaccc aacttaatcg ccttgcagca catccccctt cgccagctg gcgtaatagc     5025 gaagaggccc gcaccgatcg cccttcccaa cagttgcgca gcctgaatgg cgaatgggac    5085
gcgccctgta gcggcgcatt aagcgcggcg ggtgtggtgg ttacgcgcag cgtgaccgct    5145
acacttgcca gcgccctagc gcccgctcct ttcgctttct tcccttcctt tctcgccacg    5205
ttcgccggct ttccccgtca gctctaaat cggggctcc ctttagggtt ccgatttagt      5265
gctttacggc acctcgaccc caaaaaactt gattagggtg atggttcacg tagtgggcca    5325
tcgccctgat agacggtttt tcgccctttg acgttggagt ccacgttctt taatagtgga    5385
ctcttgttcc aaactggaac aacactcaac cctatctcgg tctattcttt tgatttataa    5445
gggattttgc cgatttcggc ctattggtta aaaaatgagc tgatttaaca aaaatttaac    5505 gcgaattta acaaaatatt aacgcttaca atttaggtgg cacttttcgg ggaaatgtgc     5565
gcggaacccc tatttgttta tttttctaaa tacattcaaa tatgtatccg ctcatgagac    5625
aataaccctg ataatgcttc aataatatt gaaaaggaa gagtatgagt attcaacatt      5685
tccgtgtcgc ccttattccc ttttttgcgg cattttgcct tcctgttttt gctcacccag    5745
aaacgctggt gaaagtaaaa gatgctgaag atcagttggg tgcacgagtg ggttacatcg    5805
```

```
aactggatct caacagcggt aagatccttg agagttttcg ccccgaagaa cgttttccaa    5865
tgatgagcac ttttaaagtt ctgctatgtg gcgcggtatt atcccgtatt gacgccgggc    5925
aagagcaact cggtcgccgc atacactatt ctcagaatga cttggttgag tactcaccag    5985
tcacagaaaa gcatcttacg gatggcatga cagtaagaga attatgcagt gctgccataa    6045
ccatgagtga taacactgcg gccaacttac ttctgacaac gatcggagga ccgaaggagc    6105
taaccgcttt tttgcacaac atggggggatc atgtaactcg ccttgatcgt tgggaaccgg    6165
agctgaatga agccatacca aacgacgagc gtgacaccac gatgcctgta gcaatggcaa    6225
caacgttgcg caaactatta actggcgaac tacttactct agcttcccgg caacaattaa    6285
tagactggat ggaggcggat aaagttgcag gaccacttct gcgctcggcc cttccggctg    6345
gctggtttat tgctgataaa tctggagccg gtgagcgtgg gtctcgcggt atcattgcag    6405
cactggggcc agatggtaag ccctcccgta tcgtagttat ctacacgacg gggagtcagg    6465
caactatgga tgaacgaaat agacagatcg ctgagatagg tgcctcactg attaagcatt    6525
ggtaactgtc agaccaagtt tactcatata ctttagat tgatttaaaa cttcattttt     6585
aatttaaaag gatctaggtg aagatccttt ttgataatct catgaccaaa atcccttaac    6645
gtgagttttc gttccactga gcgtcagacc ccgtagaaaa gatcaaagga tcttcttgag    6705 atccttttt tctgcgcgta atctgctgct tgcaaacaaa aaaaccaccg ctaccagcgg    6765
tggtttgttt gccggatcaa gagctaccaa ctcttttcc gaaggtaact ggcttcagca    6825
gagcgcagat accaaatact gttcttctag tgtagccgta gttaggccac cacttcaaga    6885
actctgtagc accgcctaca tacctcgctc tgctaatcct gttaccagtg gctgctgcca    6945
gtggcgataa gtcgtgtctt accgggttgg actcaagacg atagttaccg gataaggcgc    7005
agcggtcggg ctgaacgggg ggttcgtgca cacagcccag cttggagcga acgacctaca    7065
ccgaactgag atacctacag cgtgagctat gagaaagcgc cacgcttccc gaagggagaa    7125
aggcggacag gtatccggta agcggcaggg tcggaacagg agagcgcacg agggagcttc    7185
cagggggaaa cgcctggtat ctttatagtc ctgtcgggtt tcgccacctc tgacttgagc    7245 gtcgatttt gtgatgctcg tcagggggc ggagcctatg gaaaaacgcc agcaacgcgg    7305
cctttttacg gttcctggcc ttttgctggc cttttgctca catgttcttt cctgcgttat    7365
cccctgattc tgtggataac cgtattaccg cctttgagtg agctgatacc gctcgccgca    7425
gccgaacgac cgagcgcagc gagtcagtga gcgaggaagc ggaagagcgc ccaatacgca    7485
aaccgcctct ccccgcgcgt tggccgattc attaatgcag ctggcacgac aggtttcccg    7545
actggaaagc gggcagtgag cgcaacgcaa ttaatgtgag ttagctcact cattaggcac    7605
cccaggcttt acactttatg cttccggctc gtatgttgtg tggaattgtg agcggataac    7665
aatttcacac aggaaacagc tatgaccatg attacgccag atttaattaa ggccttaatt    7725
agg                                                                 7728
```

<210> SEQ ID NO 15  
<211> LENGTH: 107  
<212> TYPE: PRT  
<213> ORGANISM: Artificial sequence  
<220> FEATURE:  
<223> OTHER INFORMATION: Synthetic Construct

<400> SEQUENCE: 15

Arg Thr Val Ala Ala Pro Ser Val Phe Ile Phe Pro Pro Ser Asp Glu  
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 16
<211> LENGTH: 129
<212> TYPE: PRT
<213> ORGANISM: Artificial sequence
<220> FEATURE:
<223> OTHER INFORMATION: Synthetic Construct

<400> SEQUENCE: 16

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 17
<211> LENGTH: 107
<212> TYPE: PRT
<213> ORGANISM: Artificial sequence
<220> FEATURE:
<223> OTHER INFORMATION: Synthetic Construct

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

<210> SEQ ID NO 18
<211> LENGTH: 223
<212> TYPE: PRT
<213> ORGANISM: Artificial sequence
<220> FEATURE:
<223> OTHER INFORMATION: Synthetic Construct

<400> SEQUENCE: 18

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Glu Pro Asp
            35                  40                  45

Val Lys Phe Asn Trp Tyr Val Asp Gly Val Glu Val His Asn Ala Lys
        50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 19
<211> LENGTH: 7746
<212> TYPE: DNA
<213> ORGANISM: Artificial sequence
<220> FEATURE:
<223> OTHER INFORMATION: Plasmid carrying FI6 and CR8033 monoclonals
<220> FEATURE:
<221> NAME/KEY: polyA_signal
<222> LOCATION: (173)..(221)
<223> OTHER INFORMATION: synthetic\polyA
<220> FEATURE:
<221> NAME/KEY: misc_feature
<222> LOCATION: (228)..(896)
<223> OTHER INFORMATION: complement - CH'2-3
<220> FEATURE:
<221> NAME/KEY: misc_feature
<222> LOCATION: (897)..(1217)
<223> OTHER INFORMATION: complement - CH'1
<220> FEATURE:

```
<221> NAME/KEY: misc_feature
<222> LOCATION: (1218)..(1604)
<223> OTHER INFORMATION: complement - CR8033\VH
<220> FEATURE:
<221> NAME/KEY: misc_feature
<222> LOCATION: (1605)..(1655)
<223> OTHER INFORMATION: complement - leader
<220> FEATURE:
<221> NAME/KEY: misc_feature
<222> LOCATION: (1665)..(1733)
<223> OTHER INFORMATION: complement - CMV\mp2
<220> FEATURE:
<221> NAME/KEY: misc_feature
<222> LOCATION: (1734)..(2202)
<223> OTHER INFORMATION: Enhancer
<220> FEATURE:
<221> NAME/KEY: misc_feature
<222> LOCATION: (2203)..(2328)
<223> OTHER INFORMATION: CMV\mp1
<220> FEATURE:
<221> NAME/KEY: misc_feature
<222> LOCATION: (2445)..(2789)
<223> OTHER INFORMATION: KGL
<220> FEATURE:
<221> NAME/KEY: CDS
<222> LOCATION: (2784)..(3104)
<223> OTHER INFORMATION: CL
<220> FEATURE:
<221> NAME/KEY: misc_feature
<222> LOCATION: (3189)..(3248)
<223> OTHER INFORMATION: leader
<220> FEATURE:
<221> NAME/KEY: CDS
<222> LOCATION: (3249)..(3635)
<223> OTHER INFORMATION: FI6\VH
<220> FEATURE:
<221> NAME/KEY: CDS
<222> LOCATION: (3636)..(3956)
<223> OTHER INFORMATION: CH1
<220> FEATURE:
<221> NAME/KEY: CDS
<222> LOCATION: (3957)..(4625)
<223> OTHER INFORMATION: CH2-3
<220> FEATURE:
<221> NAME/KEY: misc_feature
<222> LOCATION: (3968)..(3968)
<223> OTHER INFORMATION: A -> T
<220> FEATURE:
<221> NAME/KEY: polyA_signal
<222> LOCATION: (4632)..(4709)
<223> OTHER INFORMATION: TKpAshort

<400> SEQUENCE: 19
actgaggccg cccgggcaaa gcccgggcgt cgggcgacct ttggtcgccc ggcctcagtg      60
agcgagcgag cgcgcagaga gggagtggcc aactccatca ctaggggttc cttgtagtta     120
atgattaacc cgccatgcta cttatctacg tagccatgct ctaggaagat ctcacacaaa     180
aaaccaacac acagatgtaa tgaaaataaa gatattttat tttatcactt cccgggggctc    240 aggctcaggg acttctgggt gtagtggttg tgcagggcct cgtgcatcac gctgcagctg     300
aacacgttgc cctgctgcca ccggctcttg tccacggtca gcttgctata caggaagaat     360
gagccgtcgc tgtccagcac agggggggtg gtcttgtagt tgttctcggg ctggccgttg     420
ctctcccatt ccacggcgat ctcgctgggg tagaagccct tgaccaggca ggtcagggac     480
acctggttct tggtcatctc ttcccggctg ggggcagtg tgtagacctg aggctcgcgg      540
ggctggccct tggccttgct gatggttttc tcgatggggg caggcagggc cttgttggac     600
accttgcact tgtactcttt gccgttcagc cagtcctggt gcagcacggt cagcacggac     660
accacccggt aggtgctgtt gtactgttcc tctctggggt tggtcttggc gttgtgcact     720
tccacgccgt ccacgtacca attgaacttc acttcagggt cctcgtggga cacgtccacc     780
```

```
accacgcagg tcacttcggg ggtccggctg atcatcaggg tgtccttggg ctttggggg        840
aacaggaaca cgctgggcc tcccagcagt tcaggggcag ggcagggggg acacgtgtgg         900
gtcttgtcgc agctcttagg ttccacccgc ttgtccacct tggtgttgct gggcttgtgg        960
ttcacgttgc agatgtaggt ctgggtgccc aggctgctgc tgggcacggt gaccacgctg       1020
ctcaggctat acaggccgct gctctgcagc acggctggaa aggtgtgcac gccgctggtc       1080
agggcgccag agttccagga cacggtcacg ggctcgggga gtagtccctt gaccaggcag       1140
cccagggcgg ctgttccgcc agaggtgctc ttgctgctag ggccagagg gaacacgctt        1200
ggtcccttgg tgctggcgct cgagacggtc accatggttc cctgtcccca gatatcgaag       1260
gttcctccct ccaggatatc catggcgctg ctctccagcc gatccttggc gcagtagtac       1320
agggcggtat cctcggcccg caggctgttc atctgcaggt acaggctgtt ctttccgtta       1380
tcccggctga tggtgaaccg tccctgcacg ctatcggcgt atcccatgaa gtttcccttc       1440
cagttgattc cggccaccca ctccagtccc tttcctgggg cctgccgcac ccagtgcatg       1500
gtgtactcat cgaagctgaa tccgctggcg gcgcagctca gccgcaggct ccgtcctggc       1560
tgcaccagtc ctcctccggt ctccaccagc tgcacctctg aattcgtcac cagggccagg       1620
ctcagggcga tcagcagcag cagctgcatg cgcatggtgg cggcgcgatc tgacggttca       1680
ctaaacgagc tctgcttata taggcctccc accgtacacg ccacctcgac atacctagtt       1740
attaatagta atcaattacg gggtcattag ttcatagccc atatatggag ttccgcgtta       1800
cataacttac ggtaaatggc ccgcctggct gaccgcccaa cgaccccgc ccattgacgt        1860
caataatgac gtatgttccc atagtaacgc caatagggac tttccattga cgtcaatggg       1920
tggagtattt acggtaaact gcccacttgg cagtacatca agtgtatcat atgccaagta       1980
cgccccctat tgacgtcaat gacggtaaat ggcccgcctg gcattatgcc cagtacatga       2040
ccttatggga ctttcctact tggcagtaca tctacgtatt agtcatcgct attaccatgg       2100
tgatgcggtt ttggcagtac atcaatgggc gtggatagcg gtttgactca cggggatttc       2160
caagtctcca ccccattgac gtcaatggga gtttgttttg gcaccaaaat caacgggact       2220
ttccaaaatg tcgtaacaac tccgccccat tgacgcaaat gggcggtagg cgtgtacggt       2280
gggaggtcta tataagcaga gctggtttag tgaaccgtca gatccgctgg cactttgca        2340
ctggaactta caacacccga gcaaggacgc gactctgccg ccccaccatg cgcatgcagc       2400
tgctgctgct gatcgccctg agcctggccc tggtgaccaa cagcgatatc gtcatgaccc       2460
agagcccaga tagcctggcc gtgagcctgg agagcgggc caccatcaac tgcaagagca       2520
gccagagcgt gctgtacagc agcaacaaca gaactacct ggcctggtac cagcagaagc        2580
caggacagcc accaaagctg ctgatctact gggccagcac ccgggagagc ggagtgccag       2640
atcggttcag cggaagcgga agcggaaccg atttcaccct gaccatcagc agcctgcagg       2700
ccgaggatgt ggccgtgtac tactgccagc agtactacag cacccccctg accttcggac       2760
agggaaccaa ggtggagatc aag cgt acg gtg gcc gcc cca agc gtg ttc atc      2813
                            Arg Thr Val Ala Ala Pro Ser Val Phe Ile
                             1               5                  10 ttc cca cca agc gat gag cag ctg aag agc gga acc gcc agc gtg gtg         2861
Phe Pro Pro Ser Asp Glu Gln Leu Lys Ser Gly Thr Ala Ser Val Val
             15                  20                  25 tgc ctg ctg aac aac ttc tac cca cgg gag gcc aag gtg cag tgg aag         2909
Cys Leu Leu Asn Asn Phe Tyr Pro Arg Glu Ala Lys Val Gln Trp Lys
         30                  35                  40
```

| | |
|---|---|
| gtg gat aac gcc ctg cag agc gga aac agc cag gag agc gtg acc gag<br>Val Asp Asn Ala Leu Gln Ser Gly Asn Ser Gln Glu Ser Val Thr Glu<br>            45                        50                        55 | 2957 |
| cag gat agc aag gat agc acc tac agc ctg agc agc acc ctg acc ctg<br>Gln Asp Ser Lys Asp Ser Thr Tyr Ser Leu Ser Ser Thr Leu Thr Leu<br>60                        65                        70 | 3005 |
| agc aag gcc gat tac gag aag cac aag gtg tac gcc tgc gag gtg acc<br>Ser Lys Ala Asp Tyr Glu Lys His Lys Val Tyr Ala Cys Glu Val Thr<br>75                        80                        85                        90 | 3053 |
| cac cag gga ctg agc agc cca gtg acc aag agc ttc aac cgc gga gag<br>His Gln Gly Leu Ser Ser Pro Val Thr Lys Ser Phe Asn Arg Gly Glu<br>                        95                                100                    105 | 3101 |
| tgc cggaagcggc gggccccagt gaagcagacc ctgaacttcg atctgctgaa<br>Cys | 3154 |
| gctggccgga gatgtggaga gcaacccagg accaatgtac agaatgcagc tgctgagctg | 3214 |
| catcgccctg agcctggccc tggtgaccaa cagc cag gtg caa cta gtg gag agc<br>                                                                               Gln Val Gln Leu Val Glu Ser<br>                                                                                            110 | 3269 |
| gga gga gga gtg gtg cag cca gga cgg agc ctg cgg ctg agc tgc gcc<br>Gly Gly Gly Val Val Gln Pro Gly Arg Ser Leu Arg Leu Ser Cys Ala<br>115                        120                        125                        130 | 3317 |
| gcc agc gga ttc acc ttc agc acc tac gcc atg cac tgg gtg cgg cag<br>Ala Ser Gly Phe Thr Phe Ser Thr Tyr Ala Met His Trp Val Arg Gln<br>                        135                                140                        145 | 3365 |
| gcc cca gga aag gga ctg gag tgg gtg gcc gtg atc agc tac gat gcc<br>Ala Pro Gly Lys Gly Leu Glu Trp Val Ala Val Ile Ser Tyr Asp Ala<br>                        150                                155                        160 | 3413 |
| aac tac aag tac tac gcc gat agc gtg aag gga cgg ttc acc atc agc<br>Asn Tyr Lys Tyr Tyr Ala Asp Ser Val Lys Gly Arg Phe Thr Ile Ser<br>                165                                170                                175 | 3461 |
| cgg gat aac agc aag aac acc ctg tac ctg cag atg aac agc ctg cgg<br>Arg Asp Asn Ser Lys Asn Thr Leu Tyr Leu Gln Met Asn Ser Leu Arg<br>        180                                185                                190 | 3509 |
| gcc gag gat acc gcc gtg tac tac tgc gcc aag gat agc cag ctg cgg<br>Ala Glu Asp Thr Ala Val Tyr Tyr Cys Ala Lys Asp Ser Gln Leu Arg<br>195                        200                        205                        210 | 3557 |
| agc ctg ctg tac ttc gag tgg ctg agc cag gga tac ttc gat tac tgg<br>Ser Leu Leu Tyr Phe Glu Trp Leu Ser Gln Gly Tyr Phe Asp Tyr Trp<br>                        215                                220                        225 | 3605 |
| gga cag gga acc ctg gtg acc gtg agc agc gct agc acc aag gga cca<br>Gly Gln Gly Thr Leu Val Thr Val Ser Ser Ala Ser Thr Lys Gly Pro<br>                      230                                235                        240 | 3653 |
| agc gtg ttc cca ctg gcc cca agc agc aag agc acc agc gga gga acc<br>Ser Val Phe Pro Leu Ala Pro Ser Ser Lys Ser Thr Ser Gly Gly Thr<br>        245                                250                                255 | 3701 |
| gcc gcc ctg gga tgc ctg gtg aag gat tac ttc cca gag cca gtg acc<br>Ala Ala Leu Gly Cys Leu Val Lys Asp Tyr Phe Pro Glu Pro Val Thr<br>260                        265                        270 | 3749 |
| gtg agc tgg aac agc gga gcc ctg acc agc gga gtg cac acc ttc cca<br>Val Ser Trp Asn Ser Gly Ala Leu Thr Ser Gly Val His Thr Phe Pro<br>275                        280                        285                        290 | 3797 |
| gcc gtg ctg cag agc agc gga ctg tat agc ctg agc agc gtg gtg acc<br>Ala Val Leu Gln Ser Ser Gly Leu Tyr Ser Leu Ser Ser Val Val Thr<br>                        295                                300                        305 | 3845 |
| gtg cca agc agc agc ctg gga acc cag acc tac atc tgc aac gtg aac<br>Val Pro Ser Ser Ser Leu Gly Thr Gln Thr Tyr Ile Cys Asn Val Asn<br>        310                                315                                320 | 3893 |
| cac aag cca agc aac acc aag gtg gat aag aag gtg gag cca aag agc<br>His Lys Pro Ser Asn Thr Lys Val Asp Lys Lys Val Glu Pro Lys Ser | 3941 |

```
                325                 330                 335
tgc gat aag acc cac acg tgc cct cct tgt cca gcc ccc gaa ctg ctg    3989
Cys Asp Lys Thr His Thr Cys Pro Pro Cys Pro Ala Pro Glu Leu Leu
    340                 345                 350 ggc ggg cct agc gtg ttc ctg ttt ccc cct aag cct aaa gat aca ctg    4037
Gly Gly Pro Ser Val Phe Leu Phe Pro Pro Lys Pro Lys Asp Thr Leu
355                 360                 365                 370 atg att agt aga acc cca gag gtc aca tgc gtg gtc gtg gac gtg tcc    4085
Met Ile Ser Arg Thr Pro Glu Val Thr Cys Val Val Val Asp Val Ser
                375                 380                 385 cac gaa gag cct gac gtg aag ttc aac tgg tac gtg gat ggc gtg gag    4133
His Glu Glu Pro Asp Val Lys Phe Asn Trp Tyr Val Asp Gly Val Glu
            390                 395                 400 gtg cac aat gct aag act aaa cca cgc gaa gag cag tat aat agt aca    4181
Val His Asn Ala Lys Thr Lys Pro Arg Glu Glu Gln Tyr Asn Ser Thr
        405                 410                 415 tac cga gtc gtg tca gtc ctg aca gtg ctg cac cag gat tgg ctg aac    4229
Tyr Arg Val Val Ser Val Leu Thr Val Leu His Gln Asp Trp Leu Asn
420                 425                 430 ggc aag gag tat aag tgc aag gtg tct aac aag gcc ctg ccc gcc cct    4277
Gly Lys Glu Tyr Lys Cys Lys Val Ser Asn Lys Ala Leu Pro Ala Pro
435                 440                 445                 450 atc gag aaa aca att agc aag gcc aaa ggg cag cca cgg gaa ccc cag    4325
Ile Glu Lys Thr Ile Ser Lys Ala Lys Gly Gln Pro Arg Glu Pro Gln
                455                 460                 465 gtc tac act ctg cca ccc tca aga gat gaa ctg act aag aac cag gtc    4373
Val Tyr Thr Leu Pro Pro Ser Arg Asp Glu Leu Thr Lys Asn Gln Val
            470                 475                 480 agc ctg acc tgt ctg gtg aaa ggc ttc tac ccc agc gac atc gcc gtg    4421
Ser Leu Thr Cys Leu Val Lys Gly Phe Tyr Pro Ser Asp Ile Ala Val
        485                 490                 495 gag tgg gaa agt aac ggc cag cct gag aat aac tac aag act acc cct    4469
Glu Trp Glu Ser Asn Gly Gln Pro Glu Asn Asn Tyr Lys Thr Thr Pro
500                 505                 510 cca gtg ctg gat agc gac ggg tcc ttc ttc ctg tat agc aag ctg aca    4517
Pro Val Leu Asp Ser Asp Gly Ser Phe Phe Leu Tyr Ser Lys Leu Thr
515                 520                 525                 530 gtg gac aaa tcc cgc tgg cag cag gga aac gtc ttt tcc tgt tct gtg    4565
Val Asp Lys Ser Arg Trp Gln Gln Gly Asn Val Phe Ser Cys Ser Val
                535                 540                 545 atg cat gag gcc ctg cac aat cat tac acc cag aag agt ctg tca ctg    4613
Met His Glu Ala Leu His Asn His Tyr Thr Gln Lys Ser Leu Ser Leu
            550                 555                 560 agc ccc ggc aaa tgataaaagg aacccgcgct atgacggcaa taaaaagaca        4665
Ser Pro Gly Lys
565 gaataaaacc cacgggtgtt gggtcgtttg ttcataaacc cgggatcgat aaggatcttc  4725 ctagagcatg gctacgtaga taagtagcat ggcgggttaa tcattaacta caaggaaccc  4785 ctagtgatgg agttggccac tccctctctg cgcgctcgct cgctcactga ggccgggcga  4845 ccaaaggtcg cccgacgccc gggctttgcc cggcggcct cagtgagcga gcgagcgcgc   4905 agccttaatt aacctaattc actggccgtc gttttacaac gtcgtgactg ggaaaaccct  4965 ggcgttaccc aacttaatcg ccttgcagca catccccctt tcgccagctg gcgtaatagc  5025 gaagaggccc gcaccgatcg cccttcccaa cagttgcgca gcctgaatgg cgaatgggac  5085 gcgccctgta gcggcgcatt aagcgcggcg ggtgtggtgg ttacgcgcag cgtgaccgct  5145 acacttgcca gcgccctagc gcccgctcct ttcgctttct tcccttcctt tctcgccacg  5205
```

```
ttcgccggct ttccccgtca agctctaaat cgggggctcc ctttagggtt ccgatttagt   5265
gctttacggc acctcgaccc caaaaaactt gattaggtg atggttcacg tagtgggcca    5325
tcgccctgat agacggtttt tcgccctttg acgttggagt ccacgttctt taatagtgga   5385
ctcttgttcc aaactggaac aacactcaac cctatctcgg tctattcttt tgatttataa   5445
gggattttgc cgatttcggc ctattggtta aaaatgagc tgatttaaca aaaatttaac    5505
gcgaatttta acaaaatatt aacgcttaca atttaggtgg cacttttcgg ggaaatgtgc   5565
gcggaacccc tatttgttta tttttctaaa tacattcaaa tatgtatccg ctcatgagac   5625
aataaccctg ataaatgctt caataatatt gaaaaggaa gagtatgagt attcaacatt    5685
tccgtgtcgc ccttattccc ttttttgcgg cattttgcct tcctgttttt gctcacccag   5745
aaacgctggt gaaagtaaaa gatgctgaag atcagttggg tgcacgagtg ggttacatcg   5805
aactggatct caacagcggt aagatccttg agagttttcg ccccgaagaa cgttttccaa   5865
tgatgagcac ttaaagtt ctgctatgtg gcgcggtatt atcccgtatt gacgccgggc     5925
aagagcaact cggtcgccgc atacactatt ctcagaatga cttggttgag tactcaccag   5985
tcacagaaaa gcatcttacg gatggcatga cagtaagaga attatgcagt gctgccataa   6045
ccatgagtga taacactgcg gccaacttac ttctgacaac gatcggagga ccgaaggagc   6105
taaccgcttt tttgcacaac atgggggatc atgtaactcg ccttgatcgt tgggaaccgg   6165
agctgaatga agccatacca aacgacgagc gtgacaccac gatgcctgta gcaatggcaa   6225
caacgttgcg caaactatta actggcgaac tacttactct agcttcccgg caacaattaa   6285
tagactggat ggaggcggat aaagttgcag gaccacttct gcgctcggcc cttccggctg   6345
gctggtttat tgctgataaa tctggagccg gtgagcgtgg gtctcgcggt atcattgcag   6405
cactggggcc agatggtaag ccctcccgta tcgtagttat ctacacgacg gggagtcagg   6465
caactatgga tgaacgaaat agacagatcg ctgagatagg tgcctcactg attaagcatt   6525
ggtaactgtc agaccaagtt tactcatata ctttagat tgatttaaaa cttcattttt     6585
aatttaaaag gatctaggtg aagatccttt ttgataatct catgaccaaa atcccttaac   6645
gtgagttttc gttccactga gcgtcagacc ccgtagaaaa gatcaaagga tcttcttgag   6705
atcctttttt tctgcgcgta atctgctgct tgcaaacaaa aaaaccaccg ctaccagcgg   6765
tggtttgttt gccggatcaa gagctaccaa ctctttttcc gaaggtaact ggcttcagca   6825
gagcgcagat accaaatact gttcttctag tgtagccgta gttaggccac cacttcaaga   6885
actctgtagc accgcctaca tacctcgctc tgctaatcct gttaccagtg gctgctgcca   6945
gtggcgataa gtcgtgtctt accgggttgg actcaagacg atagttaccg gataaggcgc   7005
agcggtcggg ctgaacgggg ggttcgtgca cacagcccag cttggagcga acgacctaca   7065
ccgaactgag atacctacag cgtgagctat gagaaagcgc cacgcttccc gaagggagaa   7125
aggcggacag gtatccggta agcggcaggg tcggaacagg agagcgcacg agggagcttc   7185 caggggaaa cgcctggtat ctttatagtc ctgtcgggtt tcgccacctc tgacttgagc    7245 gtcgatttt tgtgatgctcg tcagggggc ggagcctatg gaaaaacgcc agcaacgcgg    7305 ccttttacg gttcctggcc ttttgctggc cttttgctca catgttcttt cctgcgttat    7365
cccctgattc tgtggataac cgtattaccg cctttgagtg agctgatacc gctcgccgca   7425
gccgaacgac cgagcgcagc gagtcagtga gcgaggaagc ggaagagcgc ccaatacgca   7485
aaccgcctct ccccgcgcgt tggccgattc attaatgcag ctggcacgac aggtttcccg   7545
```

```
actggaaagc gggcagtgag cgcaacgcaa ttaatgtgag ttagctcact cattaggcac     7605
cccaggcttt acactttatg cttccggctc gtatgttgtg tggaattgtg agcggataac     7665
aatttcacac aggaaacagc tatgaccatg attacgccag atttaattaa ggccttaatt     7725
aggctgcgcg ctcgctcgct c                                               7746
```

<210> SEQ ID NO 20
<211> LENGTH: 107
<212> TYPE: PRT
<213> ORGANISM: Artificial sequence
<220> FEATURE:
<223> OTHER INFORMATION: Synthetic Construct

<400> SEQUENCE: 20

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 21
<211> LENGTH: 129
<212> TYPE: PRT
<213> ORGANISM: Artificial sequence
<220> FEATURE:
<223> OTHER INFORMATION: Synthetic Construct

<400> SEQUENCE: 21

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser
```

<210> SEQ ID NO 22
<211> LENGTH: 107
<212> TYPE: PRT

<213> ORGANISM: Artificial sequence
<220> FEATURE:
<223> OTHER INFORMATION: Synthetic Construct

<400> SEQUENCE: 22

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105
```

<210> SEQ ID NO 23
<211> LENGTH: 223
<212> TYPE: PRT
<213> ORGANISM: Artificial sequence
<220> FEATURE:
<223> OTHER INFORMATION: Synthetic Construct

<400> SEQUENCE: 23

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Glu Pro Asp
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

```
<210> SEQ ID NO 24
<211> LENGTH: 7740
<212> TYPE: DNA
<213> ORGANISM: Artificial sequence
<220> FEATURE:
<223> OTHER INFORMATION: Plasmid carrying FI6 and CR8033 monoclonal
      antibodies
<220> FEATURE:
<221> NAME/KEY: polyA_signal
<222> LOCATION: (191)..(239)
<223> OTHER INFORMATION: synthetic polyA
<220> FEATURE:
<221> NAME/KEY: misc_feature
<222> LOCATION: (246)..(914)
<223> OTHER INFORMATION: complement - CH'2-3
<220> FEATURE:
<221> NAME/KEY: misc_feature
<222> LOCATION: (915)..(1235)
<223> OTHER INFORMATION: complement - CH'1
<220> FEATURE:
<221> NAME/KEY: misc_feature
<222> LOCATION: (1236)..(1622)
<223> OTHER INFORMATION: complement - CR8033\VH
<220> FEATURE:
<221> NAME/KEY: misc_feature
<222> LOCATION: (1623)..(1673)
<223> OTHER INFORMATION: complement - leader
<220> FEATURE:
<221> NAME/KEY: misc_feature
<222> LOCATION: (1683)..(1751)
<223> OTHER INFORMATION: CMV\mp2
<220> FEATURE:
<221> NAME/KEY: misc_feature
<222> LOCATION: (1752)..(2220)
<223> OTHER INFORMATION: Enhancer
<220> FEATURE:
<221> NAME/KEY: misc_feature
<222> LOCATION: (2221)..(2346)
<223> OTHER INFORMATION: CMV\mp1
<220> FEATURE:
<221> NAME/KEY: misc_feature
<222> LOCATION: (2406)..(2462)
<223> OTHER INFORMATION: leader
<220> FEATURE:
<221> NAME/KEY: CDS
<222> LOCATION: (2463)..(2795)
<223> OTHER INFORMATION: FI6\VL
<220> FEATURE:
<221> NAME/KEY: CDS
<222> LOCATION: (2796)..(3116)
<223> OTHER INFORMATION: CL
<220> FEATURE:
<221> NAME/KEY: misc_feature
<222> LOCATION: (3201)..(3260)
<223> OTHER INFORMATION: leader
<220> FEATURE:
<221> NAME/KEY: CDS
<222> LOCATION: (3261)..(3647)
<223> OTHER INFORMATION: FI6\VH
<220> FEATURE:
<221> NAME/KEY: CDS
<222> LOCATION: (3648)..(3968)
<223> OTHER INFORMATION: CH1
<220> FEATURE:
<221> NAME/KEY: CDS
<222> LOCATION: (3969)..(4637)
<223> OTHER INFORMATION: CH2-3
<220> FEATURE:
<221> NAME/KEY: misc_feature
<222> LOCATION: (3980)..(3980)
<223> OTHER INFORMATION: A -> T
<220> FEATURE:
<221> NAME/KEY: polyA_signal
<222> LOCATION: (4644)..(4721)
<223> OTHER INFORMATION: TKpAshort

<400> SEQUENCE: 24
```

-continued

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gccatgctct     180
aggaagatct cacacaaaaa accaacacac agatgtaatg aaaataaaga tattttattt     240
tatcacttcc cggggctcag gctcagggac ttctgggtgt agtggttgtg cagggcctcg     300
tgcatcacgc tgcagctgaa cacgttgccc tgctgccacc ggctcttgtc cacggtcagc     360
ttgctataca ggaagaatga gccgtcgctg tccagcacag ggggggtggt cttgtagttg     420
ttctcgggct ggccgttgct ctcccattcc acggcgatct cgctggggta gaagcccttg     480
accaggcagg tcagggacac ctggttcttg gtcatctctt cccggctggg gggcagtgtg     540
tagacctgag gctcgcgggg ctggcccttg gccttgctga tggttttctc gatgggggca     600
ggcagggcct tgttggacac cttgcacttg tactctttgc cgttcagcca gtcctggtgc     660
agcacggtca gcacggacac caccgggtag gtgctgttgt actgttcctc tctgggcttg     720
gtcttggcgt tgtgcacttc cacgccgtcc acgtaccaat tgaacttcac ttcagggtcc     780
tcgtgggaca cgtccaccac cacgcaggtc acttcggggg tccggctgat catcagggtg     840
tccttgggct ttgggggaa caggaacacg ctggggcctc ccagcagttc aggggcaggg     900
caggggggac acgtgtgggt cttgtcgcag ctcttaggtt ccacccgctt gtccaccttg     960
gtgttgctgg gcttgtggtt cacgttgcag atgtaggtct gggtgcccag gctgctgctg    1020
ggcacggtga ccacgctgct caggctatac aggccgctgc tctgcagcac ggctggaaag    1080
gtgtgcacgc cgctggtcag ggcgccagag ttccaggaca cggtcacggg ctcggggaag    1140
tagtccttga ccaggcagcc cagggcggct gttccgccag aggtgctctt gctgctaggg    1200
gccagaggga cacgcttggg tcccttggtg ctggcgctcg agacggtcac catggttccc    1260
tgtccccaga tatcgaaggt tcctccctcc aggatatcca tggcgctgct ctccagccga    1320
tccttggcgc agtagtacag ggcggtatcc tcggcccgca ggctgttcat ctgcaggtac    1380
aggctgttct ttccgttatc ccggctgatg gtgaaccgtc cctgcacgct atcggcgtat    1440
cccatgaagt ttcccttcca gttgattccg gccacccact ccagtccctt tcctggggcc    1500
tgccgcaccc agtgcatggt gtactcatcg aagctgaatc cgctggcggc gcagctcagc    1560
cgcaggctcc gtcctggctg caccagtcct cctccggtct ccaccagctg cacctctgaa    1620
ttcgtcacca gggccaggct cagggcgatc agcagcagca gctgcatgcg catggtggcg    1680
gcgcgatctg acggttcact aaacgagctc tgcttatata ggcctcccac cgtacacgcc    1740
acctcgacat acctagttat taatagtaat caattacggg gtcattagtt catagcccat    1800
atatggagtt ccgcgttaca taacttacgg taaatgcccg cctggctga ccgcccaacg     1860
acccccgccc attgacgtca ataatgacgt atgttcccat agtaacgcca atagggactt    1920
tccattgacg tcaatgggtg gagtatttac ggtaaactgc ccacttggca gtacatcaag    1980
tgtatcatat gccaagtacg ccccctattg acgtcaatga cggtaaatgg cccgcctggc    2040
attatgccca gtacatgacc ttatgggact ttcctacttg gcagtacatc tacgtattag    2100
tcatcgctat taccatggtg atgcggtttt ggcagtacat caatgggcgt ggatagcggt    2160
ttgactcacg gggatttcca agtctccacc ccattgacgt caatgggagt ttgttttggc    2220
accaaaatca acgggacttt ccaaaatgtc gtaacaactc cgccccattg acgcaaatgg    2280
gcggtaggcg tgtacggtgg gaggtctata taagcagagc tggtttagtg aaccgtcaga    2340
tccgctgggc actttgcact ggaacttaca acacccgagc aaggacgcga ctctgccgcc    2400
```

-continued

```
ccaccatgcg catgcagctg ctgctgctga tcgccctgag cctggccctg gtgaccaaca      2460
```

| | | | | | | | | | | | | | | | | |
|---|---|---|---|---|---|---|---|---|---|---|---|---|---|---|---|---|
| gc | gat | atc | gtc | atg | acc | cag | agc | cca | gat | agc | ctg | gcc | gtg | agc | ctg | 2507 |
| | Asp | Ile | Val | Met | Thr | Gln | Ser | Pro | Asp | Ser | Leu | Ala | Val | Ser | Leu | |
| | 1 | | | | 5 | | | | | 10 | | | | | 15 | |

| | | | | | | | | | | | | | | | |
|---|---|---|---|---|---|---|---|---|---|---|---|---|---|---|---|
| gga | gag | cgg | gcc | acc | atc | aac | tgc | aag | agc | agc | cag | agc | gtg | acc | ttc | 2555 |
| Gly | Glu | Arg | Ala | Thr | Ile | Asn | Cys | Lys | Ser | Ser | Gln | Ser | Val | Thr | Phe | |
| | | | 20 | | | | | 25 | | | | | 30 | | | |

| | | | | | | | | | | | | | | | |
|---|---|---|---|---|---|---|---|---|---|---|---|---|---|---|---|
| aac | tac | aag | aac | tac | ctg | gcc | tgg | tac | cag | cag | aag | cca | gga | cag | cca | 2603 |
| Asn | Tyr | Lys | Asn | Tyr | Leu | Ala | Trp | Tyr | Gln | Gln | Lys | Pro | Gly | Gln | Pro | |
| | | | 35 | | | | | 40 | | | | | 45 | | | |

| | | | | | | | | | | | | | | | |
|---|---|---|---|---|---|---|---|---|---|---|---|---|---|---|---|
| cca | aag | ctg | ctg | atc | tac | tgg | gcc | agc | acc | cgg | gag | agc | gga | gtg | cca | 2651 |
| Pro | Lys | Leu | Leu | Ile | Tyr | Trp | Ala | Ser | Thr | Arg | Glu | Ser | Gly | Val | Pro | |
| | | 50 | | | | | 55 | | | | | 60 | | | | |

| | | | | | | | | | | | | | | | |
|---|---|---|---|---|---|---|---|---|---|---|---|---|---|---|---|
| gat | cgg | ttc | agc | gga | agc | gga | agc | gga | acc | gat | ttc | acc | ctg | acc | atc | 2699 |
| Asp | Arg | Phe | Ser | Gly | Ser | Gly | Ser | Gly | Thr | Asp | Phe | Thr | Leu | Thr | Ile | |
| | 65 | | | | | 70 | | | | | 75 | | | | | |

| | | | | | | | | | | | | | | | |
|---|---|---|---|---|---|---|---|---|---|---|---|---|---|---|---|
| agc | agc | ctg | cag | gcc | gag | gat | gtg | gcc | gtg | tac | tac | tgc | cag | cag | cac | 2747 |
| Ser | Ser | Leu | Gln | Ala | Glu | Asp | Val | Ala | Val | Tyr | Tyr | Cys | Gln | Gln | His | |
| 80 | | | | | 85 | | | | | 90 | | | | | 95 | |

| | | | | | | | | | | | | | | | |
|---|---|---|---|---|---|---|---|---|---|---|---|---|---|---|---|
| tac | cgg | acc | cca | cca | acc | ttc | gga | cag | gga | acc | aag | gtg | gag | atc | aag | 2795 |
| Tyr | Arg | Thr | Pro | Pro | Thr | Phe | Gly | Gln | Gly | Thr | Lys | Val | Glu | Ile | Lys | |
| | | | 100 | | | | | 105 | | | | | 110 | | | |

| | | | | | | | | | | | | | | | |
|---|---|---|---|---|---|---|---|---|---|---|---|---|---|---|---|
| cgt | acg | gtg | gcc | gcc | cca | agc | gtg | ttc | atc | ttc | cca | cca | agc | gat | gag | 2843 |
| Arg | Thr | Val | Ala | Ala | Pro | Ser | Val | Phe | Ile | Phe | Pro | Pro | Ser | Asp | Glu | |
| | | | 115 | | | | | 120 | | | | | 125 | | | |

| | | | | | | | | | | | | | | | |
|---|---|---|---|---|---|---|---|---|---|---|---|---|---|---|---|
| cag | ctg | aag | agc | gga | acc | gcc | agc | gtg | gtg | tgc | ctg | ctg | aac | aac | ttc | 2891 |
| Gln | Leu | Lys | Ser | Gly | Thr | Ala | Ser | Val | Val | Cys | Leu | Leu | Asn | Asn | Phe | |
| | | | 130 | | | | | 135 | | | | | 140 | | | |

| | | | | | | | | | | | | | | | |
|---|---|---|---|---|---|---|---|---|---|---|---|---|---|---|---|
| tac | cca | cgg | gag | gcc | aag | gtg | cag | tgg | aag | gtg | gat | aac | gcc | ctg | cag | 2939 |
| Tyr | Pro | Arg | Glu | Ala | Lys | Val | Gln | Trp | Lys | Val | Asp | Asn | Ala | Leu | Gln | |
| | 145 | | | | | 150 | | | | | 155 | | | | | |

| | | | | | | | | | | | | | | | |
|---|---|---|---|---|---|---|---|---|---|---|---|---|---|---|---|
| agc | gga | aac | agc | cag | gag | agc | gtg | acc | gag | cag | gat | agc | aag | gat | agc | 2987 |
| Ser | Gly | Asn | Ser | Gln | Glu | Ser | Val | Thr | Glu | Gln | Asp | Ser | Lys | Asp | Ser | |
| 160 | | | | | 165 | | | | | 170 | | | | | 175 | |

| | | | | | | | | | | | | | | | |
|---|---|---|---|---|---|---|---|---|---|---|---|---|---|---|---|
| acc | tac | agc | ctg | agc | agc | acc | ctg | acc | ctg | agc | aag | gcc | gat | tac | gag | 3035 |
| Thr | Tyr | Ser | Leu | Ser | Ser | Thr | Leu | Thr | Leu | Ser | Lys | Ala | Asp | Tyr | Glu | |
| | | | 180 | | | | | 185 | | | | | 190 | | | |

| | | | | | | | | | | | | | | | |
|---|---|---|---|---|---|---|---|---|---|---|---|---|---|---|---|
| aag | cac | aag | gtg | tac | gcc | tgc | gag | gtg | acc | cac | cag | gga | ctg | agc | agc | 3083 |
| Lys | His | Lys | Val | Tyr | Ala | Cys | Glu | Val | Thr | His | Gln | Gly | Leu | Ser | Ser | |
| | | | 195 | | | | | 200 | | | | | 205 | | | |

| | | | | | | | | | | |
|---|---|---|---|---|---|---|---|---|---|---|
| cca | gtg | acc | aag | agc | ttc | aac | cgc | gga | gag | tgc | cggaagcggc gggcccagt | 3136 |
| Pro | Val | Thr | Lys | Ser | Phe | Asn | Arg | Gly | Glu | Cys | | |
| | | 210 | | | | | 215 | | | | | |

```
gaagcagacc ctgaacttcg atctgctgaa gctggccgga gatgtggaga gcaacccagg      3196
accaatgtac agaatgcagc tgctgagctg catcgccctg agcctggccc tggtgaccaa      3256
```

| | | | | | | | | | | | | | | | |
|---|---|---|---|---|---|---|---|---|---|---|---|---|---|---|---|
| cagc | cag | gtg | caa | cta | gtg | gag | agc | gga | gga | gga | gtg | gtg | cag | cca | gga | 3305 |
| Gln | Val | Gln | Leu | Val | Glu | Ser | Gly | Gly | Gly | Val | Val | Gln | Pro | Gly | | |
| | 220 | | | | | 225 | | | | | 230 | | | | | |

| | | | | | | | | | | | | | | | |
|---|---|---|---|---|---|---|---|---|---|---|---|---|---|---|---|
| cgg | agc | ctg | cgg | ctg | agc | tgc | gcc | gcc | agc | gga | ttc | acc | ttc | agc | acc | 3353 |
| Arg | Ser | Leu | Arg | Leu | Ser | Cys | Ala | Ala | Ser | Gly | Phe | Thr | Phe | Ser | Thr | |
| | 235 | | | | | 240 | | | | | 245 | | | | | |

| | | | | | | | | | | | | | | | |
|---|---|---|---|---|---|---|---|---|---|---|---|---|---|---|---|
| tac | gcc | atg | cac | tgg | gtg | cgg | cag | gcc | cca | gga | aag | gga | ctg | gag | tgg | 3401 |
| Tyr | Ala | Met | His | Trp | Val | Arg | Gln | Ala | Pro | Gly | Lys | Gly | Leu | Glu | Trp | |
| 250 | | | | | 255 | | | | | 260 | | | | | 265 | |

| | | | | | | | | | | | | | | | |
|---|---|---|---|---|---|---|---|---|---|---|---|---|---|---|---|
| gtg | gcc | gtg | atc | agc | tac | gat | gcc | aac | tac | aag | tac | tac | gcc | gat | agc | 3449 |
| Val | Ala | Val | Ile | Ser | Tyr | Asp | Ala | Asn | Tyr | Lys | Tyr | Tyr | Ala | Asp | Ser | |
| | | | 270 | | | | | 275 | | | | | 280 | | | |

```
gtg aag gga cgg ttc acc atc agc cgg gat aac agc aag aac acc ctg       3497
Val Lys Gly Arg Phe Thr Ile Ser Arg Asp Asn Ser Lys Asn Thr Leu
            285                 290                 295 tac ctg cag atg aac agc ctg cgg gcc gag gat acc gcc gtg tac tac       3545
Tyr Leu Gln Met Asn Ser Leu Arg Ala Glu Asp Thr Ala Val Tyr Tyr
            300                 305                 310 tgc gcc aag gat agc cag ctg cgg agc ctg ctg tac ttc gag tgg ctg       3593
Cys Ala Lys Asp Ser Gln Leu Arg Ser Leu Leu Tyr Phe Glu Trp Leu
            315                 320                 325 agc cag gga tac ttc gat tac tgg gga cag gga acc ctg gtg acc gtg       3641
Ser Gln Gly Tyr Phe Asp Tyr Trp Gly Gln Gly Thr Leu Val Thr Val
330                 335                 340                 345 agc agc gct agc acc aag gga cca agc gtg ttc cca ctg gcc cca agc       3689
Ser Ser Ala Ser Thr Lys Gly Pro Ser Val Phe Pro Leu Ala Pro Ser
                350                 355                 360 agc aag agc acc agc gga gga acc gcc gcc ctg gga tgc ctg gtg aag       3737
Ser Lys Ser Thr Ser Gly Gly Thr Ala Ala Leu Gly Cys Leu Val Lys
            365                 370                 375 gat tac ttc cca gag cca gtg acc gtg agc tgg aac agc gga gcc ctg       3785
Asp Tyr Phe Pro Glu Pro Val Thr Val Ser Trp Asn Ser Gly Ala Leu
            380                 385                 390 acc agc gga gtg cac acc ttc cca gcc gtg ctg cag agc agc gga ctg       3833
Thr Ser Gly Val His Thr Phe Pro Ala Val Leu Gln Ser Ser Gly Leu
395                 400                 405 tat agc ctg agc agc gtg gtg acc gtg cca agc agc agc ctg gga acc       3881
Tyr Ser Leu Ser Ser Val Val Thr Val Pro Ser Ser Ser Leu Gly Thr
410                 415                 420                 425 cag acc tac atc tgc aac gtg aac cac aag cca agc aac acc aag gtg       3929
Gln Thr Tyr Ile Cys Asn Val Asn His Lys Pro Ser Asn Thr Lys Val
                430                 435                 440 gat aag aag gtg gag cca aag agc tgc gat aag acc cac acg tgc cct       3977
Asp Lys Lys Val Glu Pro Lys Ser Cys Asp Lys Thr His Thr Cys Pro
            445                 450                 455 cct tgt cca gcc ccc gaa ctg ctg ggc ggg cct agc gtg ttc ctg ttt       4025
Pro Cys Pro Ala Pro Glu Leu Leu Gly Gly Pro Ser Val Phe Leu Phe
            460                 465                 470 ccc cct aag cct aaa gat aca ctg atg att agt aga acc cca gag gtc       4073
Pro Pro Lys Pro Lys Asp Thr Leu Met Ile Ser Arg Thr Pro Glu Val
475                 480                 485 aca tgc gtg gtc gtg gac gtg tcc cac gaa gag cct gac gtg aag ttc       4121
Thr Cys Val Val Val Asp Val Ser His Glu Glu Pro Asp Val Lys Phe
490                 495                 500                 505 aac tgg tac gtg gat ggc gtg gag gtg cac aat gct aag act aaa cca       4169
Asn Trp Tyr Val Asp Gly Val Glu Val His Asn Ala Lys Thr Lys Pro
                510                 515                 520 cgc gaa gag cag tat aat agt aca tac cga gtc gtg tca gtc ctg aca       4217
Arg Glu Glu Gln Tyr Asn Ser Thr Tyr Arg Val Val Ser Val Leu Thr
            525                 530                 535 gtg ctg cac cag gat tgg ctg aac ggc aag gag tat aag tgc aag gtg       4265
Val Leu His Gln Asp Trp Leu Asn Gly Lys Glu Tyr Lys Cys Lys Val
            540                 545                 550 tct aac aag gcc ctg ccc gcc cct atc gag aaa aca att agc aag gcc       4313
Ser Asn Lys Ala Leu Pro Ala Pro Ile Glu Lys Thr Ile Ser Lys Ala
555                 560                 565 aaa ggg cag cca cgg gaa ccc cag gtc tac act ctg cca ccc tca aga       4361
Lys Gly Gln Pro Arg Glu Pro Gln Val Tyr Thr Leu Pro Pro Ser Arg
570                 575                 580                 585 gat gaa ctg act aag aac cag gtc agc ctg acc tgt ctg gtg aaa ggc       4409
Asp Glu Leu Thr Lys Asn Gln Val Ser Leu Thr Cys Leu Val Lys Gly
                590                 595                 600
```

| | | |
|---|---|---|
| ttc tac ccc agc gac atc gcc gtg gag tgg gaa agt aac ggc cag cct<br>Phe Tyr Pro Ser Asp Ile Ala Val Glu Trp Glu Ser Asn Gly Gln Pro<br>605 610 615 | | 4457 |
| gag aat aac tac aag act acc cct cca gtg ctg gat agc gac ggg tcc<br>Glu Asn Asn Tyr Lys Thr Thr Pro Pro Val Leu Asp Ser Asp Gly Ser<br>620 625 630 | | 4505 |
| ttc ttc ctg tat agc aag ctg aca gtg gac aaa tcc cgc tgg cag cag<br>Phe Phe Leu Tyr Ser Lys Leu Thr Val Asp Lys Ser Arg Trp Gln Gln<br>635 640 645 | | 4553 |
| gga aac gtc ttt tcc tgt tct gtg atg cat gag gcc ctg cac aat cat<br>Gly Asn Val Phe Ser Cys Ser Val Met His Glu Ala Leu His Asn His<br>650 655 660 665 | | 4601 |
| tac acc cag aag agt ctg tca ctg agc ccc ggc aaa tgataaaagg<br>Tyr Thr Gln Lys Ser Leu Ser Leu Ser Pro Gly Lys<br>670 675 | | 4647 |
| aacccgcgct atgacggcaa taaaaagaca gaataaaacc cacgggtgtt gggtcgtttg | | 4707 |
| ttcataaacc cgggatcgat aaggatcttc ctagagcatg gctacgtaga taagtagcat | | 4767 |
| ggcgggttaa tcattaacta caaggaaccc ctagtgatgg agttggccac tccctctctg | | 4827 |
| cgcgctcgct cgctcactga ggccgggcga ccaaaggtcg cccgacgccc gggctttgcc | | 4887 |
| cgggcggcct cagtgagcga gcgagcgcgc agccttaatt aacctaattc actggccgtc | | 4947 |
| gttttacaac gtcgtgactg ggaaaaccct ggcgttaccc aacttaatcg ccttgcagca | | 5007 |
| catccccctt tcgccagctg gcgtaatagc gaagaggccc gcaccgatcg cccttcccaa | | 5067 |
| cagttgcgca gcctgaatgg cgaatgggac gcgccctgta gcggcgcatt aagcgcggcg | | 5127 |
| ggtgtggtgg ttacgcgcag cgtgaccgct acacttgcca gcgccctagc gcccgctcct | | 5187 |
| ttcgctttct tcccttcctt tctcgccacg ttcgccggct ttccccgtca gctctaaat | | 5247 |
| cggggggctcc ctttagggtt ccgatttagt gctttacggc acctcgaccc caaaaaactt | | 5307 |
| gattagggtg atggttcacg tagtgggcca tcgccctgat agacggtttt tcgccctttg | | 5367 |
| acgttggagt ccacgttctt taatagtgga ctcttgttcc aaactggaac aacactcaac | | 5427 |
| cctatctcgg tctattcttt tgatttataa gggattttgc cgatttcggc ctattggtta | | 5487 |
| aaaaatgagc tgatttaaca aaaatttaac gcgaattta acaaaatatt aacgcttaca | | 5547 |
| atttaggtgg cacttttcgg ggaaatgtgc gcggaacccc tatttgttta ttttttctaaa | | 5607 |
| tacattcaaa tatgtatccg ctcatgagac aataaccctg ataaatgctt caataatatt | | 5667 |
| gaaaaaggaa gagtatgagt attcaacatt tccgtgtcgc ccttattccc ttttttgcgg | | 5727 |
| cattttgcct tcctgttttt gctcacccag aaacgctggt gaaagtaaaa gatgctgaag | | 5787 |
| atcagttggg tgcacgagtg ggttacatcg aactggatct caacagcggt aagatccttg | | 5847 |
| agagttttcg ccccgaagaa cgttttccaa tgatgagcac ttttaaagtt ctgctatgtg | | 5907 |
| gcgcggtatt atcccgtatt gacgccgggc aagagcaact cggtcgccgc atacactatt | | 5967 |
| ctcagaatga cttggttgag tactcaccag tcacagaaaa gcatcttacg gatggcatga | | 6027 |
| cagtaagaga attatgcagt gctgccataa ccatgagtga taacactgcg gccaacttac | | 6087 |
| ttctgacaac gatcggagga ccgaaggagc taaccgcttt tttgcacaac atgggggatc | | 6147 |
| atgtaactcg ccttgatcgt tgggaaccgg agctgaatga agccatacca aacgacgagc | | 6207 |
| gtgacaccac gatgcctgta gcaatggcaa caacgttgcg caaactatta actggcgaac | | 6267 |
| tacttactct agcttcccgg caacaattaa tagactggat ggaggcggat aaagttgcag | | 6327 |
| gaccacttct gcgctcggcc cttccggctg gctggtttat tgctgataaa tctggagccg | | 6387 |

```
gtgagcgtgg gtctcgcggt atcattgcag cactggggcc agatggtaag ccctcccgta    6447
tcgtagttat ctacacgacg gggagtcagg caactatgga tgaacgaaat agacagatcg    6507
ctgagatagg tgcctcactg attaagcatt ggtaactgtc agaccaagtt tactcatata    6567
tactttagat tgatttaaaa cttcattttt aatttaaaag gatctaggtg aagatccttt    6627
ttgataatct catgaccaaa atcccttaac gtgagttttc gttccactga gcgtcagacc    6687
ccgtagaaaa gatcaaagga tcttcttgag atcctttttt tctgcgcgta atctgctgct    6747
tgcaaacaaa aaaaccaccg ctaccagcgg tggtttgttt gccggatcaa gagctaccaa    6807
ctctttttcc gaaggtaact ggcttcagca gagcgcagat accaaatact gttcttctag    6867
tgtagccgta gttaggccac cacttcaaga actctgtagc accgcctaca tacctcgctc    6927
tgctaatcct gttaccagtg gctgctgcca gtggcgataa gtcgtgtctt accgggttgg    6987
actcaagacg atagttaccg gataaggcgc agcggtcggg ctgaacgggg ggttcgtgca    7047
cacagcccag cttggagcga acgacctaca ccgaactgag atacctacag cgtgagctat    7107
gagaaagcgc cacgcttccc gaagggagaa aggcggacag gtatccggta agcggcaggg    7167
tcggaacagg agagcgcacg agggagcttc caggggggaaa cgcctggtat ctttatagtc    7227
ctgtcgggtt tcgccacctc tgacttgagc gtcgattttt gtgatgctcg tcaggggggc    7287
ggagcctatg gaaaaacgcc agcaacgcgg cctttttacg gttcctggcc ttttgctggc    7347
cttttgctca catgttcttt cctgcgttat cccctgattc tgtggataac cgtattaccg    7407
cctttgagtg agctgatacc gctcgccgca gccgaacgac cgagcgcagc gagtcagtga    7467
gcgaggaagc ggaagagcgc ccaatacgca aaccgcctct ccccgcgcgt tggccgattc    7527
attaatgcag ctggcacgac aggtttcccg actggaaagc gggcagtgag cgcaacgcaa    7587
ttaatgtgag ttagctcact cattaggcac cccaggcttt acactttatg cttccggctc    7647
gtatgttgtg tggaattgtg agcggataac aatttcacac aggaaacagc tatgaccatg    7707
attacgccag atttaattaa ggccttaatt agg                                 7740
```

<210> SEQ ID NO 25
<211> LENGTH: 111
<212> TYPE: PRT
<213> ORGANISM: Artificial sequence
<220> FEATURE:
<223> OTHER INFORMATION: Synthetic Construct

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys
            100                 105                 110

<210> SEQ ID NO 26

```
<211> LENGTH: 107
<212> TYPE: PRT
<213> ORGANISM: Artificial sequence
<220> FEATURE:
<223> OTHER INFORMATION: Synthetic Construct

<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 27
<211> LENGTH: 129
<212> TYPE: PRT
<213> ORGANISM: Artificial sequence
<220> FEATURE:
<223> OTHER INFORMATION: Synthetic Construct

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 28
<211> LENGTH: 107
<212> TYPE: PRT
<213> ORGANISM: Artificial sequence
<220> FEATURE:
<223> OTHER INFORMATION: Synthetic Construct

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His
            100                 105
```

<210> SEQ ID NO 29
<211> LENGTH: 223
<212> TYPE: PRT
<213> ORGANISM: Artificial sequence
<220> FEATURE:
<223> OTHER INFORMATION: Synthetic Construct

<400> SEQUENCE: 29

```
Thr Cys Pro Pro Cys Pro Ala Pro Glu Leu Leu Gly Gly Pro Ser Val
 1               5                  10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Asp
            35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
        210                 215                 220
```

<210> SEQ ID NO 30
<211> LENGTH: 7782
<212> TYPE: DNA
<213> ORGANISM: Artificial
<220> FEATURE:
<223> OTHER INFORMATION: EcoRV
<220> FEATURE:
<221> NAME/KEY: polyA_signal
<222> LOCATION: (201)..(252)

<223> OTHER INFORMATION: complement - synthetic\polyA
<220> FEATURE:
<221> NAME/KEY: misc_feature
<222> LOCATION: (268)..(588)
<223> OTHER INFORMATION: complement - CL
<220> FEATURE:
<221> NAME/KEY: misc_feature
<222> LOCATION: (589)..(909)
<223> OTHER INFORMATION: complement - TCN032\VL
<220> FEATURE:
<221> NAME/KEY: polyA_signal
<222> LOCATION: (910)..(966)
<223> OTHER INFORMATION: complement - leader
<220> FEATURE:
<221> NAME/KEY: misc_feature
<222> LOCATION: (1026)..(1094)
<223> OTHER INFORMATION: complement - CMV\mp2
<220> FEATURE:
<221> NAME/KEY: misc_feature
<222> LOCATION: (1095)..(1563)
<223> OTHER INFORMATION: Enhancer
<220> FEATURE:
<221> NAME/KEY: misc_feature
<222> LOCATION: (1564)..(1689)
<223> OTHER INFORMATION: CMV\mp1
<220> FEATURE:
<221> NAME/KEY: misc_feature
<222> LOCATION: (1749)..(1805)
<223> OTHER INFORMATION: leader
<220> FEATURE:
<221> NAME/KEY: CDS
<222> LOCATION: (1806)..(2165)
<223> OTHER INFORMATION: TCN032\VH
<220> FEATURE:
<221> NAME/KEY: CDS
<222> LOCATION: (2166)..(2459)
<223> OTHER INFORMATION: CH1
<220> FEATURE:
<221> NAME/KEY: misc_feature
<222> LOCATION: (2460)..(3152)
<223> OTHER INFORMATION: hinge-CH2'-CH3'
<220> FEATURE:
<221> NAME/KEY: misc_feature
<222> LOCATION: (3239)..(3296)
<223> OTHER INFORMATION: leader
<220> FEATURE:
<221> NAME/KEY: CDS
<222> LOCATION: (3297)..(3683)
<223> OTHER INFORMATION: FI6\VH
<220> FEATURE:
<221> NAME/KEY: CDS
<222> LOCATION: (3684)..(4004)
<223> OTHER INFORMATION: CH1
<220> FEATURE:
<221> NAME/KEY: CDS
<222> LOCATION: (4005)..(4673)
<223> OTHER INFORMATION: CH2-3
<220> FEATURE:
<221> NAME/KEY: polyA_signal
<222> LOCATION: (4693)..(4770)
<223> OTHER INFORMATION: TKpAshort

<400> SEQUENCE: 30

```
ggccttaatt aggctgcgcg ctcgctcgct cactgaggcc gcccgggcaa agcccgggcg    60
tcgggcgacc tttggtcgcc cggcctcagt gagcgagcga gcgcgcagag agggagtggc   120
caactccatc actaggggtt ccttgtagtt aatgattaac ccgccatgct acttatctac   180
gtagccatgc tctaggaaga tctcacacaa aaaaccaaca cacagatgta atgaaaataa   240
agatatttta ttgcggccgc tttatcagca ctctccgcgg ttgaagctct tggtcactgg   300
gctgctcagt ccctggtggg tcacctcgca ggcgtacacc ttgtgcttct cgtaatcggc   360
cttgctcagg gtcagggtgc tgctcaggct gtaggtgcta tccttgctat cctgctcggt   420
cacgctctcc tggctgtttc cgctctgcag ggcgttatcc accttccact gcaccttggc   480
```

```
ctcccgtggg tagaagttgt tcagcaggca caccacgctg gcggttccgc tcttcagctg    540
ctcatcgctt ggtgggaaga tgaacacgct tggggcggcc accgtacgct tgatctccac    600
ccgggttcct cctccgaagg tcagtggtgg gctgtagctc tgctggcagt agtaggtggc    660
gaaatcctct ggctgcaggc tggtgatggt cagggtgaaa tcggttccgc ttccgcttcc    720
gctgaaccgg cttggcactc cgctctgcag tccgctggcg cgctgatca gtccctttgg    780
ggcctttcct ggccgctgct ggtaccagtt caggtacttg tagatgttct ggctggcccg    840
gcaggtgatg gtcacccgat ctcccacgct ggcgctcagg ctgcttgggc tctgggtcat    900
ctggatatcg ctgttggtca ccagggccag gctcagggcg atcagcagca gcagctgcat    960
tctcatggtg gagagtcgcg tccttgctcg ggtgttgtaa gttccagtgc aaagtgcccc   1020
aattggcgat ctgacggttc actaaacgag ctctgcttat ataggcctcc caccgtacac   1080
gccacctcga catacctagt tattaatagt aatcaattac ggggtcatta gttcatagcc   1140
catatatgga gttccgcgtt acataactta cggtaaatgg cccgcctggc tgaccgccca   1200
acgaccccg cccattgacg tcaataatga cgtatgttcc catagtaacg ccaataggga   1260
ctttccattg acgtcaatgg gtggagtatt tacggtaaac tgcccacttg gcagtacatc   1320
aagtgtatca tatgccaagt acgcccccta ttgacgtcaa tgacggtaaa tggcccgcct   1380
ggcattatgc ccagtacatg acctatggga ctttcctac ttggcagtac atctacgtat   1440
tagtcatcgc tattaccatg gtgatgcggt tttggcagta catcaatggg cgtggatagc   1500
ggtttgactc acggggattt ccaagtctcc accccattga cgtcaatggg agtttgtttt   1560
ggcaccaaaa tcaacgggac tttccaaaat gtcgtaacaa ctccgcccca ttgacgcaaa   1620
tgggcggtag gcgtgtacgg tgggaggtct atataagcag agctggttta gtgaaccgtc   1680
agatccgctg ctagcgggca cttttgcactg aacttacaa caccccgagca aggacgcgac   1740
tctccaccat gcgcatgcag ctgctgctgc tgatcgccct gagcctggcc ctggtgacca   1800
```

| | | | | | | | | | | | | | | | | |
|---|---|---|---|---|---|---|---|---|---|---|---|---|---|---|---|---|
| acagc | cag | gtg | cag | ctg | cag | gag | agc | gga | cca | gga | ctg | gtg | aag | cca | agc | 1850 |
| | Gln | Val | Gln | Leu | Gln | Glu | Ser | Gly | Pro | Gly | Leu | Val | Lys | Pro | Ser | |
| | 1 | | | | 5 | | | | | 10 | | | | | 15 | |

```
gag acc ctg agc ctg acc tgc acc gtg agc gga agc agc atc agc aac    1898
Glu Thr Leu Ser Leu Thr Cys Thr Val Ser Gly Ser Ser Ile Ser Asn
         20                  25                  30 tac tac tgg agc tgg atc cgg cag agc cca gga aag gga ctg gag tgg    1946
Tyr Tyr Trp Ser Trp Ile Arg Gln Ser Pro Gly Lys Gly Leu Glu Trp
     35                  40                  45 atc gga ttc atc tac tac gga gga aac acc aag tac aac cca agc ctg    1994
Ile Gly Phe Ile Tyr Tyr Gly Gly Asn Thr Lys Tyr Asn Pro Ser Leu
 50                  55                  60 aag agc cgg gtg acc atc agc cag gat acc agc aag agc cag gtg agc    2042
Lys Ser Arg Val Thr Ile Ser Gln Asp Thr Ser Lys Ser Gln Val Ser
 65                  70                  75 ctg acc atg agc agc gtg acc gcc gcc gag agc gcc gtg tac ttc tgc    2090
Leu Thr Met Ser Ser Val Thr Ala Ala Glu Ser Ala Val Tyr Phe Cys
 80                  85                  90                  95 gcc cgg gcc agc tgc agc gga gga tac tgc atc ctg gat tac tgg gga    2138
Ala Arg Ala Ser Cys Ser Gly Gly Tyr Cys Ile Leu Asp Tyr Trp Gly
             100                 105                 110 cag gga acc ctg gtg acc gtg agc agc gcg tcg acc aag gga cct tcg    2186
Gln Gly Thr Leu Val Thr Val Ser Ser Ala Ser Thr Lys Gly Pro Ser
         115                 120                 125 gtc ttc ccc ctg gca ccc tcc tcc aag agc acc tct ggg ggc aca gcg    2234
Val Phe Pro Leu Ala Pro Ser Ser Lys Ser Thr Ser Gly Gly Thr Ala
```

```
                130               135                140
gcc ctg ggc tgc ctg gtc aag gac tac ttc ccc gaa ccg gtg acg gtg    2282
Ala Leu Gly Cys Leu Val Lys Asp Tyr Phe Pro Glu Pro Val Thr Val
        145                150                155 tcg tgg aac tca ggc gcc ctg acc agc ggc gtg cac acc ttc ccg gct    2330
Ser Trp Asn Ser Gly Ala Leu Thr Ser Gly Val His Thr Phe Pro Ala
160                165                170                175 gtc cta cag tcc tca gga ctc tac tcc ctc agc agc gtg gtg acc gtg    2378
Val Leu Gln Ser Ser Gly Leu Tyr Ser Leu Ser Ser Val Val Thr Val
                180                185                190 ccc tcc agc agc ttg ggc acc cag acc tac atc tgc aac gtg aat cac    2426
Pro Ser Ser Ser Leu Gly Thr Gln Thr Tyr Ile Cys Asn Val Asn His
            195                200                205 aag ccc agc aac acc aag gtg gac aag aaa gtt gaaccaaaga gctgcgacaa  2479
Lys Pro Ser Asn Thr Lys Val Asp Lys Lys Val
        210                215 gacccacacg tgtcccccct gccctgcccc tgaactgctg ggaggcccca gcgtgttcct  2539
gttcccccca aagcccaagg acaccctgat gatcagccgg accccgaag tgacctgcgt   2599 ggtggtggac gtgtcccacg aggaccctga agtgaagttt aattggtacg tggacggcgt  2659
ggaagtgcac aacgccaaga ccaagcccag agaggaacag tacaacagca cctaccgggt  2719
ggtgtccgtg ctgaccgtgc tgcaccagga ctggctgaac ggcaaagagt acaagtgcaa  2779
ggtgtccaac aaggccctgc ctgccccat cgagaaaacc atcagcaagg ccaagggcca   2839
gccccgcgag cctcaggtct acacactgcc cccagccgg aagagatga ccaagaacca    2899 ggtgtccctg acctgcctgg tcaagggctt ctaccccagc gacatcgccg tggaatggga  2959
gagcaacggc cagcccgaga caactacaa gaccacccc cctgtgctgg acagcgacgg    3019
ctcattcttc ctgtatagca agctgaccgt ggacaagagc cggtggcagc agggcaacgt  3079
gttcagctgc agcgtgatgc acgaggccct gcacaaccac tacacccaga gtccctgag   3139 cctgagcccc ggcagaaagc ggagagcccc cgtgaagcag accctgaact tcgacctgct  3199
gaagctggcc ggcgacgtgg aaagcaaccc tggcccctatg tacagaatgc agctgctgag  3259
ctgcatcgcc ctgagcctgg ccctggtgac caacagc cag gtg caa cta gtg gag  3314
                                         Gln Val Gln Leu Val Glu
                                                         220 agc gga gga gga gtg gtg cag cca gga cgg agc ctg cgg ctg agc tgc    3362
Ser Gly Gly Gly Val Val Gln Pro Gly Arg Ser Leu Arg Leu Ser Cys
225                230                235                240 gcc gcc agc gga ttc acc ttc agc acc tac gcc atg cac tgg gtg cgg    3410
Ala Ala Ser Gly Phe Thr Phe Ser Thr Tyr Ala Met His Trp Val Arg
                245                250                255 cag gcc cca gga aag gga ctg gag tgg gtg gcc gtg atc agc tac gat    3458
Gln Ala Pro Gly Lys Gly Leu Glu Trp Val Ala Val Ile Ser Tyr Asp
            260                265                270 gcc aac tac aag tac tac gcc gat agc gtg aag gga cgg ttc acc atc    3506
Ala Asn Tyr Lys Tyr Tyr Ala Asp Ser Val Lys Gly Arg Phe Thr Ile
        275                280                285 agc cgg gat aac agc aag aac acc ctg tac ctg cag atg aac agc ctg    3554
Ser Arg Asp Asn Ser Lys Asn Thr Leu Tyr Leu Gln Met Asn Ser Leu
    290                295                300 cgg gcc gag gat acc gcc gtg tac tac tgc gcc aag gat agc cag ctg    3602
Arg Ala Glu Asp Thr Ala Val Tyr Tyr Cys Ala Lys Asp Ser Gln Leu
305                310                315                320 cgg agc ctg ctg tac ttc gag tgg ctg agc cag gga tac ttc gat tac    3650
Arg Ser Leu Leu Tyr Phe Glu Trp Leu Ser Gln Gly Tyr Phe Asp Tyr
                325                330                335
```

| | |
|---|---|
| tgg gga cag gga acc ctg gtg acc gtg agc agc gcc agc acc aag ggg<br>Trp Gly Gln Gly Thr Leu Val Thr Val Ser Ser Ala Ser Thr Lys Gly<br>340 345 350 | 3698 |
| ccc agc gtg ttc cca ctg gcc cca agc agc aag agc acc agc gga gga<br>Pro Ser Val Phe Pro Leu Ala Pro Ser Ser Lys Ser Thr Ser Gly Gly<br>355 360 365 | 3746 |
| acc gcc gcc ctg gga tgc ctg gtg aag gat tac ttc cca gag cca gtg<br>Thr Ala Ala Leu Gly Cys Leu Val Lys Asp Tyr Phe Pro Glu Pro Val<br>370 375 380 | 3794 |
| acc gtg agc tgg aac agc gga gcc ctg acc agc gga gtg cac acc ttc<br>Thr Val Ser Trp Asn Ser Gly Ala Leu Thr Ser Gly Val His Thr Phe<br>385 390 395 400 | 3842 |
| cca gcc gtg ctg cag agc agc gga ctg tat agc ctg agc agc gtg gtg<br>Pro Ala Val Leu Gln Ser Ser Gly Leu Tyr Ser Leu Ser Ser Val Val<br>405 410 415 | 3890 |
| acc gtg cca agc agc agc ctg gga acc cag acc tac atc tgc aac gtg<br>Thr Val Pro Ser Ser Ser Leu Gly Thr Gln Thr Tyr Ile Cys Asn Val<br>420 425 430 | 3938 |
| aac cac aag cca agc aac acc aag gtg gat aag aag gtg gag cca aag<br>Asn His Lys Pro Ser Asn Thr Lys Val Asp Lys Lys Val Glu Pro Lys<br>435 440 445 | 3986 |
| agc tgc gat aag acc cac acg tgc cct cca tgt cca gcc ccc gaa ctg<br>Ser Cys Asp Lys Thr His Thr Cys Pro Pro Cys Pro Ala Pro Glu Leu<br>450 455 460 | 4034 |
| ctg ggc ggg cct agc gtg ttc ctg ttt ccc cct aag cct aaa gat aca<br>Leu Gly Gly Pro Ser Val Phe Leu Phe Pro Pro Lys Pro Lys Asp Thr<br>465 470 475 480 | 4082 |
| ctg atg att agt aga acc cca gag gtc aca tgc gtg gtc gtg gac gtg<br>Leu Met Ile Ser Arg Thr Pro Glu Val Thr Cys Val Val Val Asp Val<br>485 490 495 | 4130 |
| tcc cac gaa gag cct gac gtg aag ttc aac tgg tac gtg gat ggc gtg<br>Ser His Glu Glu Pro Asp Val Lys Phe Asn Trp Tyr Val Asp Gly Val<br>500 505 510 | 4178 |
| gag gtg cac aat gct aag act aaa cca cgc gaa gag cag tat aat agt<br>Glu Val His Asn Ala Lys Thr Lys Pro Arg Glu Glu Gln Tyr Asn Ser<br>515 520 525 | 4226 |
| aca tac cga gtc gtg tca gtc ctg aca gtg ctg cac cag gat tgg ctg<br>Thr Tyr Arg Val Val Ser Val Leu Thr Val Leu His Gln Asp Trp Leu<br>530 535 540 | 4274 |
| aac ggc aag gag tat aag tgc aag gtg tct aac aag gcc ctg ccc gcc<br>Asn Gly Lys Glu Tyr Lys Cys Lys Val Ser Asn Lys Ala Leu Pro Ala<br>545 550 555 560 | 4322 |
| cct atc gag aaa aca att agc aag gcc aaa ggg cag cca cgg gaa ccc<br>Pro Ile Glu Lys Thr Ile Ser Lys Ala Lys Gly Gln Pro Arg Glu Pro<br>565 570 575 | 4370 |
| cag gtc tac act ctg cca ccc tca aga gat gaa ctg act aag aac cag<br>Gln Val Tyr Thr Leu Pro Pro Ser Arg Asp Glu Leu Thr Lys Asn Gln<br>580 585 590 | 4418 |
| gtc agc ctg acc tgt ctg gtg aaa ggc ttc tac ccc agc gac atc gcc<br>Val Ser Leu Thr Cys Leu Val Lys Gly Phe Tyr Pro Ser Asp Ile Ala<br>595 600 605 | 4466 |
| gtg gag tgg gaa agt aac ggc cag cct gag aat aac tac aag act acc<br>Val Glu Trp Glu Ser Asn Gly Gln Pro Glu Asn Asn Tyr Lys Thr Thr<br>610 615 620 | 4514 |
| cct cca gtg ctg gat agc gac ggg tcc ttc ttc ctg tat agc aag ctg<br>Pro Pro Val Leu Asp Ser Asp Gly Ser Phe Phe Leu Tyr Ser Lys Leu<br>625 630 635 640 | 4562 |
| aca gtg gac aaa tcc cgc tgg cag cag gga aac gtc ttt tcc tgt tct<br>Thr Val Asp Lys Ser Arg Trp Gln Gln Gly Asn Val Phe Ser Cys Ser | 4610 |

|     |     |     |     |     | 645 |     |     |     | 650 |     |     |     |     | 655 |     |      |
|-----|-----|-----|-----|-----|-----|-----|-----|-----|-----|-----|-----|-----|-----|-----|-----|------|
| gtg | atg | cat | gag | gcc | ctg | cac | aat | cat | tac | acc | cag | aag | agt | ctg | tca | 4658 |
| Val | Met | His | Glu | Ala | Leu | His | Asn | His | Tyr | Thr | Gln | Lys | Ser | Leu | Ser |      |
|     |     |     |     | 660 |     |     |     |     | 665 |     |     |     |     | 670 |     |      |

| ctg | agc | ccc | ggc | aaa | tgataaaaag | cttctcgaga | aggaacccgc | gctatgacgg | 4713 |
|-----|-----|-----|-----|-----|-----|-----|-----|-----|------|
| Leu | Ser | Pro | Gly | Lys |     |     |     |     |      |
|     |     | 675 |     |     |     |     |     |     |      |

```
caataaaaag acagaataaa acccacgggt gttgggtcgt tgttcataa acccgggaag    4773 cttatcgata aggatcttcc tagagcatgg ctacgtagat aagtagcatg gcgggttaat    4833
cattaactac aaggaacccc tagtgatgga gttggccact ccctctctgc gcgctcgctc    4893
gctcactgag gccgggcgac caaaggtcgc ccgacgcccg ggctttgccc gggcggcctc    4953
agtgagcgag cgagcgcgca gccttaatta acctaattca ctggccgtcg ttttacaacg    5013
tcgtgactgg gaaaaccctg gcgttaccca acttaatcgc cttgcagcac atcccccttt    5073
cgccagctgg cgtaatagcg aagaggcccg caccgatcgc ccttcccaac agttgcgcag    5133
cctgaatggc gaatgggacg cgccctgtag cggcgcatta agcgcggcgg gtgtggtggt    5193
tacgcgcagc gtgaccgcta cacttgccag cgccctagcg cccgctcctt tcgctttctt    5253
cccttccttt ctcgccacgt tcgccggctt tccccgtcaa gctctaaatc gggggctccc    5313
tttagggttc cgatttagtg ctttacggca cctcgacccc aaaaaacttg attagggtga    5373
tggttcacgt agtgggccat cgccctgata acggttttt cgcccttga cgttggagtc    5433 cacgttcttt aatagtggac tcttgttcca aactggaaca acactcaacc ctatctcggt    5493
ctattctttt gatttataag ggattttgcc gatttcggcc tattggttaa aaatgagct    5553 gatttaacaa aaatttaacg cgaattttaa caaaatatta acgcttacaa tttaggtggc    5613
acttttcggg gaaatgtgcg cggaacccct atttgtttat ttttctaaat acattcaaat    5673
atgtatccgc tcatgagaca ataaccctga taaatgcttc aataatattg aaaaaggaag    5733
agtatgagta ttcaacattt ccgtgtcgcc cttattccct tttttgcggc attttgcctt    5793 cctgttttg ctcacccaga aacgctggtg aaagtaaaag atgctgaaga tcagttgggt    5853
gcacgagtgg gttacatcga actggatctc aacagcggta agatccttga gagttttcgc    5913
cccgaagaac gttttccaat gatgagcact tttaaagttc tgctatgtgg cgcggtatta    5973
tcccgtattg acgccgggca agagcaactc ggtcgccgca tacactattc tcagaatgac    6033
ttggttgagt actcaccagt cacagaaaag catcttacgg atggcatgac agtaagagaa    6093
ttatgcagtg ctgccataac catgagtgat aacactgcgg ccaacttact tctgacaacg    6153
atcggaggac cgaaggagct aaccgctttt ttgcacaaca tgggggatca tgtaactcgc    6213
cttgatcgtt gggaaccgga gctgaatgaa gccataccaa acgacgagcg tgacaccacg    6273
atgcctgtag caatggcaac aacgttgcgc aaactattaa ctggcgaact acttactcta    6333
gcttcccggc aacaattaat agactggatg gaggcggata agttgcagg accacttctg    6393 cgctcggccc ttccggctgg ctggtttatt gctgataaat ctggagccgg tgagcgtggg    6453
tctcgcggta tcattgcagc actggggcca gatggtaagc cctcccgtat cgtagttatc    6513
tacacgacgg ggagtcaggc aactatggat gaacgaaata gacagatcgc tgagataggt    6573
gcctcactga ttaagcattg gtaactgtca gaccaagttt actcatatat actttagatt    6633
gatttaaaac ttcatttta atttaaaagg atctaggtga agatcctttt tgataatctc    6693
atgaccaaaa tcccttaacg tgagttttcg ttccactgag cgtcagaccc cgtagaaaag    6753
atcaaaggat cttcttgaga tcctttttt ctgcgcgtaa tctgctgctt gcaaacaaaa    6813
```

```
aaaccaccgc taccagcggt ggtttgtttg ccggatcaag agctaccaac tcttttccg      6873 aaggtaactg gcttcagcag agcgcagata ccaaatactg ttcttctagt gtagccgtag      6933
ttaggccacc acttcaagaa ctctgtagca ccgcctacat acctcgctct gctaatcctg      6993
ttaccagtgg ctgctgccag tggcgataag tcgtgtctta ccgggttgga ctcaagacga      7053
tagttaccgg ataaggcgca gcggtcgggc tgaacggggg gttcgtgcac acagcccagc      7113
ttggagcgaa cgacctacac cgaactgaga tacctacagc gtgagctatg agaaagcgcc      7173
acgcttcccg aagggagaaa ggcggacagg tatccggtaa gcggcagggt cggaacagga      7233
gagcgcacga gggagcttcc aggggaaac gcctggtatc tttatagtcc tgtcgggttt       7293
cgccacctct gacttgagcg tcgattttg tgatgctcgt caggggggcg gagcctatgg       7353
aaaaacgcca gcaacgcggc cttttacgg ttcctggcct tttgctggcc ttttgctcac       7413
atgttctttc ctgcgttatc ccctgattct gtggataacc gtattaccgc ctttgagtga      7473
gctgataccg ctcgccgcag ccgaacgacc gagcgcagcg agtcagtgag cgaggaagcg      7533
gaagagcgcc caatacgcaa accgcctctc cccgcgcgtt ggccgattca ttaatgcagc      7593
tggcacgaca ggtttcccga ctggaaagcg ggcagtgagc gcaacgcaat taatgtgagt      7653
tagctcactc attaggcacc ccaggcttta cactttatgc ttccggctcg tatgttgtgt      7713
ggaattgtga gcggataaca atttcacaca ggaaacagct atgaccatga ttacgccaga      7773
tttaattaa                                                             7782
```

<210> SEQ ID NO 31
<211> LENGTH: 120
<212> TYPE: PRT
<213> ORGANISM: Artificial
<220> FEATURE:
<223> OTHER INFORMATION: Synthetic Construct

<400> SEQUENCE: 31

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ser Asn Tyr
            20                  25                  30

Tyr Trp Ser Trp Ile Arg Gln Ser Pro Gly Lys Gly Leu Glu Trp Ile
        35                  40                  45

Gly Phe Ile Tyr Tyr Gly Gly Asn Thr Lys Tyr Asn Pro Ser Leu Lys
    50                  55                  60

Ser Arg Val Thr Ile Ser Gln Asp Thr Ser Lys Ser Gln Val Ser Leu
65                  70                  75                  80

Thr Met Ser Ser Val Thr Ala Ala Glu Ser Ala Val Tyr Phe Cys Ala
                85                  90                  95

Arg Ala Ser Cys Ser Gly Gly Tyr Cys Ile Leu Asp Tyr Trp Gly Gln
            100                 105                 110

Gly Thr Leu Val Thr Val Ser Ser
        115                 120
```

<210> SEQ ID NO 32
<211> LENGTH: 98
<212> TYPE: PRT
<213> ORGANISM: Artificial
<220> FEATURE:
<223> OTHER INFORMATION: Synthetic Construct

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 33
<211> LENGTH: 129
<212> TYPE: PRT
<213> ORGANISM: Artificial
<220> FEATURE:
<223> OTHER INFORMATION: Synthetic Construct

<400> SEQUENCE: 33

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 34
<211> LENGTH: 107
<212> TYPE: PRT
<213> ORGANISM: Artificial
<220> FEATURE:
<223> OTHER INFORMATION: Synthetic Construct

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr 65                  70                  75                  80
            Tyr Ile Cys Asn Val Asn His Lys Pro Ser Asn Thr Lys Val Asp Lys
                            85                  90                  95
            Lys Val Glu Pro Lys Ser Cys Asp Lys Thr His
                        100                 105

<210> SEQ ID NO 35
<211> LENGTH: 223
<212> TYPE: PRT
<213> ORGANISM: Artificial
<220> FEATURE:
<223> OTHER INFORMATION: Synthetic Construct

<400> SEQUENCE: 35

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Glu Pro Asp
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 36
<211> LENGTH: 7814
<212> TYPE: DNA
<213> ORGANISM: Artificial sequence
<220> FEATURE:
<223> OTHER INFORMATION: FI6 and C05 immunoadhesins
<220> FEATURE:
<221> NAME/KEY: polyA_signal
<222> LOCATION: (201)..(432)
<223> OTHER INFORMATION: complement - SV40\polyA
<220> FEATURE:
<221> NAME/KEY: misc_feature
<222> LOCATION: (453)..(1121)
<223> OTHER INFORMATION: complement - CH'2-3
<220> FEATURE:
<221> NAME/KEY: misc_feature
<222> LOCATION: (1125)..(1457)
<223> OTHER INFORMATION: complement - C05\VL

```
<220> FEATURE:
<221> NAME/KEY: misc_feature
<222> LOCATION: (1458)..(1502)
<223> OTHER INFORMATION: SL\from\3bn201co
<220> FEATURE:
<221> NAME/KEY: misc_feature
<222> LOCATION: (1503)..(1916)
<223> OTHER INFORMATION: complement - C05\VH
<220> FEATURE:
<221> NAME/KEY: misc_feature
<222> LOCATION: (1965)..(1973)
<223> OTHER INFORMATION: leader
<220> FEATURE:
<221> NAME/KEY: misc_feature
<222> LOCATION: (2371)..(2412)
<223> OTHER INFORMATION: complement - CMV\mp2
<220> FEATURE:
<221> NAME/KEY: misc_feature
<222> LOCATION: (2413)..(2881)
<223> OTHER INFORMATION: enhancer
<220> FEATURE:
<221> NAME/KEY: misc_feature
<222> LOCATION: (2882)..(3007)
<223> OTHER INFORMATION: CMV\mp1
<220> FEATURE:
<221> NAME/KEY: misc_feature
<222> LOCATION: (3067)..(3055)
<223> OTHER INFORMATION: leader
<220> FEATURE:
<221> NAME/KEY: CDS
<222> LOCATION: (3124)..(3510)
<223> OTHER INFORMATION: FI6\VH
<220> FEATURE:
<221> NAME/KEY: misc_feature
<222> LOCATION: (3511)..(3555)
<223> OTHER INFORMATION: SL\from\3bn201co
<220> FEATURE:
<221> NAME/KEY: CDS
<222> LOCATION: (3556)..(3888)
<223> OTHER INFORMATION: FI6\VL
<220> FEATURE:
<221> NAME/KEY: CDS
<222> LOCATION: (3892)..(4560)
<223> OTHER INFORMATION: CH2-3
<220> FEATURE:
<221> NAME/KEY: polyA_signal
<222> LOCATION: (4581)..(4812)
<223> OTHER INFORMATION: SV40\polyA

<400> SEQUENCE: 36
ggccttaatt aggctgcgcg ctcgctcgct cactgaggcc gcccgggcaa agcccgggcg      60
tcgggcgacc tttggtcgcc cggcctcagt gagcgagcga gcgcgcagag agggagtggc     120
caactccatc actagggggtt ccttgtagtt aatgattaac ccgccatgct acttatctac     180
gtagccatgc tctaggaaga tcattttacc acatttgtag aggttttact tgctttaaaa     240
aacctcccac atctccccct gaacctgaaa cataaaatga atgcaattgt tgttgttaac     300
ttgtttattg cagcttataa tggttacaaa taaagcaata gcatcacaaa tttcacaaat     360
aaagcatttt tttcactgca ttctagttgt ggtttgtcca aactcatcaa tgtatcttat     420
catgtctgct cgaagcggcc gcaagcttat cacttcccgg ggctcaggct cagggacttc     480
tgggtgtagt ggttgtgcag ggcctcgtgc atcacgctgc agctgaacac gttgccctgc     540
tgccaccggc tcttgtccac ggtcagcttg ctatacagga agaatgagcc gtcgctgtcc     600
agcacagggg gggtggtctt gtagttgttc tcgggctggc cgttgctctc ccattccacg     660
gcgatctcgc tggggtagaa gcccttgacc aggcaggtca gggacacctg gttcttggtc     720
atctcttccc ggctgggggg cagtgtgtag acctgaggct cgcggggctg gcccttggcc     780
ttgctgatgg ttttctcgat gggggcaggc agggccttgt tggacacctt gcacttgtac     840
```

```
tctttgccgt tcagccagtc ctggtgcagc acggtcagca cggacaccac ccggtaggtg      900
ctgttgtact gttcctctct gggcttggtc ttggcgttgt gcacttccac gccgtccacg      960
taccaattga acttcacttc agggtcctcg tgggacacgt ccaccaccac gcaggtcact     1020
tcggggtcc ggctgatcat cagggtgtcc ttgggctttg ggggaacag gaacacgctg      1080
gggcctccca gcagttcagg ggcagggcag gggggacacg tggctagcac cgtacgcttg     1140
atctccagct tggttcctcc tccgaaggtg aatggcagtc catcgtactg ctggcagtag     1200
taggttccca catccttcag gctgcaggcc acgctgctgc tcaggctgat ctgtcccaga     1260
tccactccgc tgaaccggct tggcactccc cgctgcaggt tgctggcatc gtagatcagc     1320
agctttggtc cctttcctgg cttctgctgg taccagttca ggaacttcct gatgtcctgg     1380
ctggcctggc aggtcagggt cacccgatct cccacgctgg cgctcaggct gcttgggctc     1440
tgggtcagct ggatatcaga tcccccgcct ccggaccctc ctcctccgct gcctcctccg     1500
ccgctcgaga cggtcaccag ggttccctgt ccccacacat cgaaggcatc tcccaccaga     1560
tcggcccgct cccatccggc gctcaccacc tgctgcatgg acatgtgctt ggcgcagtag     1620
tacactccgg tatcctccac ccgcaggttg gtcatctgca ggtacagggt ctccttgctg     1680
ttatcccggc tgatggtgaa ccgtccctcc acgctatcgg cgtaatcaat gtctcctcct     1740
ccggcgttga tgatgctcag ccactccagt cccttttcctg gggcctgccg cacccagctc     1800
acggcgtagt agctcagggt gctctctccg aagctgcttc cgcttccac gcagctcagc      1860
cgcaggctct ctcctggctg caccagtcct cctccgctct cctgcagctg cacctgtgaa     1920
ttcgtcacca gggccaggct cagggcgatc agcagcagca gctgcatgcg catggtgggg     1980
cggcagagtc gcgtccttgc tcgggtgttg taagttccag tgcaaagtgc cctagcctat     2040
agtgagtcgt attaagtact ctagccttaa gagctgtaat tgaactggga gtggacacct     2100
gtggagagaa aggcaaagtg gatgtcagta agaccaatag gtgcctatca gaaacgcaag     2160
agtcttctct gtctcgacaa gcccagtttc tattggtctc cttaaacctg tcttgtaacc     2220
ttgatactta cctgcccagt gcctcacgac caacttctgc agcttaagtt cgagactgtt     2280
gtgtcagaag cactgactgc gttagcaatt taactgtgat aaactaccgc aataaagctt     2340
ctagtgatct gacggttcac taaacgagct ctgcttatat aggcctccca ccgtacacgc     2400
cacctcgaca tacctagtta ttaatagtaa tcaattacgg ggtcattagt tcatagccca     2460
tatatggagt tccgcgttac ataacttacg gtaaatggcc cgcctggctg accgcccaac     2520
gacccccgcc cattgacgtc aataatgacg tatgttccca tagtaacgcc aatagggact     2580
ttccattgac gtcaatgggt ggagtattta cggtaaactg cccacttggc agtacatcaa     2640
gtgtatcata tgccaagtac gccccctatt gacgtcaatg acggtaaatg gcccgcctgg     2700
cattatgccc agtacatgac cttatgggac tttcctactt ggcagtacat ctacgtatta     2760
gtcatcgcta ttaccatggt gatgcggttt tggcagtaca tcaatgggcg tggatagcgg     2820
tttgactcac ggggatttcc aagtctccac cccattgacg tcaatgggag tttgttttgg     2880
caccaaaatc aacgggactt tccaaaatgt cgtaacaact ccgccccatt gacgcaaatg     2940
ggcggtaggc gtgtacggtg ggaggtctat ataagcagag ctggtttagt gaaccgtcag     3000
atccgctggg cactttgcac tggaacttac aacacccgag caaggacgcg actctgccgc     3060
cccaccatgc gcatgcagct gctgctgctg atcgccctga gcctggccct ggtgaccaac     3120
agc cag gtg caa ttg gtg gag agc gga gga gga gtg gtg cag cca gga     3168
    Gln Val Gln Leu Val Glu Ser Gly Gly Gly Val Val Gln Pro Gly
     1               5                  10                  15
```

```
cgg agc ctg cgg ctg agc tgc gcc gcc agc gga ttc acc ttc agc acc    3216
Arg Ser Leu Arg Leu Ser Cys Ala Ala Ser Gly Phe Thr Phe Ser Thr
            20                  25                  30 tac gcc atg cac tgg gtg cgg cag gcc cca gga aag gga ctg gag tgg    3264
Tyr Ala Met His Trp Val Arg Gln Ala Pro Gly Lys Gly Leu Glu Trp
            35                  40                  45 gtg gcc gtg atc agc tac gat gcc aac tac aag tac tac gcc gat agc    3312
Val Ala Val Ile Ser Tyr Asp Ala Asn Tyr Lys Tyr Tyr Ala Asp Ser
            50                  55                  60 gtg aag gga cgg ttc acc atc agc cgg gat aac agc aag aac acc ctg    3360
Val Lys Gly Arg Phe Thr Ile Ser Arg Asp Asn Ser Lys Asn Thr Leu
65                  70                  75 tac ctg cag atg aac agc ctg cgg gcc gag gat acc gcc gtg tac tac    3408
Tyr Leu Gln Met Asn Ser Leu Arg Ala Glu Asp Thr Ala Val Tyr Tyr
80                  85                  90                  95 tgc gcc aag gat agc cag ctg cgg agc ctg ctg tac ttc gag tgg ctg    3456
Cys Ala Lys Asp Ser Gln Leu Arg Ser Leu Leu Tyr Phe Glu Trp Leu
                100                 105                 110 agc cag gga tac ttc gat tac tgg gga cag gga acc ctg gtg acc gtg    3504
Ser Gln Gly Tyr Phe Asp Tyr Trp Gly Gln Gly Thr Leu Val Thr Val
                115                 120                 125 agc agc ggcggaggag gcagcggagg aggagggtcc ggaggcgggg gatct gat atc   3561
Ser Ser                                                    Asp Ile
                                                               130 gtc atg acc cag agc cca gat agc ctg gcc gtg agc ctg gga gag cgg    3609
Val Met Thr Gln Ser Pro Asp Ser Leu Ala Val Ser Leu Gly Glu Arg
            135                 140                 145 gcc acc atc aac tgc aag agc agc cag agc gtg acc ttc aac tac aag    3657
Ala Thr Ile Asn Cys Lys Ser Ser Gln Ser Val Thr Phe Asn Tyr Lys
            150                 155                 160 aac tac ctg gcc tgg tac cag cag aag cca gga cag cca cca aag ctg    3705
Asn Tyr Leu Ala Trp Tyr Gln Gln Lys Pro Gly Gln Pro Pro Lys Leu
            165                 170                 175 ctg atc tac tgg gcc agc acc cgg gag agc gga gtg cca gat cgg ttc    3753
Leu Ile Tyr Trp Ala Ser Thr Arg Glu Ser Gly Val Pro Asp Arg Phe
180                 185                 190                 195 agc gga agc gga agc gga acc gat ttc acc ctg acc atc agc agc ctg    3801
Ser Gly Ser Gly Ser Gly Thr Asp Phe Thr Leu Thr Ile Ser Ser Leu
                200                 205                 210 cag gcc gag gat gtg gcc gtg tac tac tgc cag cag cac tac cgg acc    3849
Gln Ala Glu Asp Val Ala Val Tyr Tyr Cys Gln Gln His Tyr Arg Thr
                215                 220                 225 cca cca acc ttc gga cag gga acc aag gtg gag atc aag gcc acg tgc    3897
Pro Pro Thr Phe Gly Gln Gly Thr Lys Val Glu Ile Lys     Thr Cys
            230                 235                 240 cct cca tgt cca gcc ccc gaa ctg ctg ggc ggg cct agc gtg ttc ctg    3945
Pro Pro Cys Pro Ala Pro Glu Leu Leu Gly Gly Pro Ser Val Phe Leu
            245                 250                 255 ttt ccc cct aag cct aaa gat aca ctg atg att agt aga acc cca gag    3993
Phe Pro Pro Lys Pro Lys Asp Thr Leu Met Ile Ser Arg Thr Pro Glu
            260                 265                 270 gtc aca tgc gtg gtc gtg gac gtg tcc cac gaa gag cct gac gtg aag    4041
Val Thr Cys Val Val Val Asp Val Ser His Glu Glu Pro Asp Val Lys
275                 280                 285                 290 ttc aac tgg tac gtg gat ggc gtg gag gtg cac aat gct aag act aaa    4089
Phe Asn Trp Tyr Val Asp Gly Val Glu Val His Asn Ala Lys Thr Lys
                295                 300                 305 cca cgc gaa gag cag tat aat agt aca tac cga gtc gtg tca gtc ctg    4137
Pro Arg Glu Glu Gln Tyr Asn Ser Thr Tyr Arg Val Val Ser Val Leu
```

```
                  310                 315                 320
aca gtg ctg cac cag gat tgg ctg aac ggc aag gag tat aag tgc aag      4185
Thr Val Leu His Gln Asp Trp Leu Asn Gly Lys Glu Tyr Lys Cys Lys
            325                 330                 335 gtg tct aac aag gcc ctg ccc gcc cct atc gag aaa aca att agc aag      4233
Val Ser Asn Lys Ala Leu Pro Ala Pro Ile Glu Lys Thr Ile Ser Lys
340                 345                 350 gcc aaa ggg cag cca cgg gaa ccc cag gtc tac act ctg cca ccc tca      4281
Ala Lys Gly Gln Pro Arg Glu Pro Gln Val Tyr Thr Leu Pro Pro Ser
355                 360                 365                 370 aga gat gaa ctg act aag aac cag gtc agc ctg acc tgt ctg gtg aaa      4329
Arg Asp Glu Leu Thr Lys Asn Gln Val Ser Leu Thr Cys Leu Val Lys
                375                 380                 385 ggc ttc tac ccc agc gac atc gcc gtg gag tgg gaa agt aac ggc cag      4377
Gly Phe Tyr Pro Ser Asp Ile Ala Val Glu Trp Glu Ser Asn Gly Gln
            390                 395                 400 cct gag aat aac tac aag act acc cct cca gtg ctg gat agc gac ggg      4425
Pro Glu Asn Asn Tyr Lys Thr Thr Pro Pro Val Leu Asp Ser Asp Gly
            405                 410                 415 tcc ttc ttc ctg tat agc aag ctg aca gtg gac aaa tcc cgc tgg cag      4473
Ser Phe Phe Leu Tyr Ser Lys Leu Thr Val Asp Lys Ser Arg Trp Gln
420                 425                 430 cag gga aac gtc ttt tcc tgt tct gtg atg cat gag gcc ctg cac aat      4521
Gln Gly Asn Val Phe Ser Cys Ser Val Met His Glu Ala Leu His Asn
435                 440                 445                 450 cat tac acc cag aag agt ctg tca ctg agc ccc ggc aaa tgataagctt       4570
His Tyr Thr Gln Lys Ser Leu Ser Leu Ser Pro Gly Lys
                455                 460 gcggccgctt cgagcagaca tgataagata cattgatgag tttggacaaa ccacaactag    4630
aatgcagtga aaaaaatgct ttatttgtga aatttgtgat gctattgctt tatttgtaac    4690
cattataagc tgcaataaac aagttaacaa caacaattgc attcatttta tgtttcaggt    4750 tcaggggag atgtgggagg ttttttaaag caagtaaaac ctctacaaat gtggtaaaat     4810
cgataaggat cttcctagag catggctacg tagataagta gcatggcggg ttaatcatta    4870
actacaagga accccagtg atggagttgg ccactccctc tctgcgcgct cgctcgctca     4930
ctgaggccgg gcgaccaaag gtcgcccgac gcccgggctt tgcccgggcg gcctcagtga    4990
gcgagcgagc gcgcagcctt aattaaccta attcactggc cgtcgtttta caacgtcgtg    5050
actgggaaaa ccctggcgtt acccaactta atcgccttgc agcacatccc ctttcgcca     5110 gctggcgtaa tagcgaagag gcccgcaccg atcgcccttc ccaacagttg cgcagcctga    5170
atggcgaatg gacgcgcccc tgtagcggcg cattaagcgc ggcgggtgtg gtggttacgc    5230
gcagcgtgac cgctacactt gccagcgccc tagcgcccgc tcctttcgct ttcttccctt    5290
cctttctcgc cacgttcgcc ggctttcccc gtcaagctct aaatcggggg ctccctttag    5350
ggttccgatt tagtgcttta cggcacctcg accccaaaaa acttgattag ggtgatggtt    5410
cacgtagtgg gccatcgccc tgatagacgg ttttcgccc tttgacgttg gagtccacgt     5470
tctttaatag tggactcttg ttccaaactg gaacaacact caaccctatc tcggtctatt    5530
cttttgattt ataagggatt ttgccgattt cggcctattg gttaaaaaat gagctgattt    5590
aacaaaaatt taacgcgaat tttaacaaaa tattaacgct tacaatttag gtggcacttt    5650
tcggggaaat gtgcgcggaa cccctatttg tttatttttc taaatacatt caaatatgta    5710
tccgctcatg agacaataac cctgataaat gcttcaataa tattgaaaaa ggaagagtat    5770
gagtattcaa catttccgtg tcgcccttat tcccttttttt gcggcatttt gccttcctgt    5830
```

```
ttttgctcac ccagaaacgc tggtgaaagt aaaagatgct gaagatcagt tgggtgcacg      5890
agtgggttac atcgaactgg atctcaacag cggtaagatc cttgagagtt ttcgccccga      5950
agaacgtttt ccaatgatga gcactttttaa agttctgcta tgtggcgcgg tattatcccg      6010
tattgacgcc gggcaagagc aactcggtcg ccgcatacac tattctcaga atgacttggt      6070
tgagtactca ccagtcacag aaaagcatct tacggatggc atgacagtaa gagaattatg      6130
cagtgctgcc ataaccatga gtgataacac tgcggccaac ttacttctga caacgatcgg      6190
aggaccgaag gagctaaccg cttttttgca acatggggg  gatcatgtaa ctcgccttga      6250
tcgttgggaa ccgagctga  atgaagccat accaaacgac gagcgtgaca ccacgatgcc      6310
tgtagcaatg gcaacaacgt tgcgcaaact attaactggc gaactactta ctctagcttc      6370
ccggcaacaa ttaatagact ggatggaggc ggataaagtt gcaggaccac ttctgcgctc      6430
ggcccttccg gctggctggt ttattgctga taaatctgga gccggtgagc gtgggtctcg      6490
cggtatcatt gcagcactgg ggccagatgg taagccctcc cgtatcgtag ttatctacac      6550
gacggggagt caggcaacta tggatgaacg aaatagacag atcgctgaga taggtgcctc      6610
actgattaag cattggtaac tgtcagacca agtttactca tatatacttt agattgattt      6670
aaaacttcat ttttaattta aaaggatcta ggtgaagatc ctttttgata atctcatgac      6730
caaaatccct taacgtgagt tttcgttcca ctgagcgtca gacccccgtag aaaagatcaa      6790 aggatcttct tgagatcctt ttttttctgcg cgtaatctgc tgcttgcaaa caaaaaaacc      6850
accgctacca gcggtggttt gtttgccgga tcaagagcta ccaactcttt ttccgaaggt      6910
aactggcttc agcagagcgc agataccaaa tactgttctt ctagtgtagc cgtagttagg      6970
ccaccacttc aagaactctg tagcaccgcc tacatacctc gctctgctaa tcctgttacc      7030
agtggctgct gccagtggcg ataagtcgtg tcttaccggg ttggactcaa gacgatagtt      7090
accggataag gcgcagcggt cgggctgaac ggggggttcg tgcacacagc ccagcttgga      7150
gcgaacgacc tacaccgaac tgagatacct acagcgtgag ctatgagaaa gcgccacgct      7210
tcccgaaggg agaaaggcgg acaggtatcc ggtaagcggc agggtcggaa caggagagcg      7270
cacgagggag cttccagggg gaaacgcctg gtatctttat agtcctgtcg ggtttcgcca      7330
cctctgactt gagcgtcgat ttttgtgatg ctcgtcaggg gggcggagcc tatgaaaaa      7390 cgccagcaac gcggcctttt tacggttcct ggccttttgc tggccttttg ctcacatgtt      7450
ctttcctgcg ttatcccctg attctgtgga taaccgtatt accgcctttg agtgagctga      7510
taccgctcgc cgcagccgaa cgaccgagcg cagcgagtca gtgagcgagg aagcggaaga      7570
gcgcccaata cgcaaaccgc ctctccccgc gcgttggccg attcattaat gcagctggca      7630
cgacaggttt cccgactgga aagcgggcag tgagcgcaac gcaattaatg tgagttagct      7690
cactcattag gcaccccagg ctttacactt tatgcttccg gctcgtatgt tgtgtggaat      7750
tgtgagcgga taacaatttc acacaggaaa cagctatgac catgattacg ccagatttaa      7810
ttaa                                                                  7814
```

<210> SEQ ID NO 37
<211> LENGTH: 129
<212> TYPE: PRT
<213> ORGANISM: Artificial sequence
<220> FEATURE:
<223> OTHER INFORMATION: Synthetic Construct

<400> SEQUENCE: 37

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
                115                 120                 125

Ser
```

<210> SEQ ID NO 38
<211> LENGTH: 111
<212> TYPE: PRT
<213> ORGANISM: Artificial sequence
<220> FEATURE:
<223> OTHER INFORMATION: Synthetic Construct

<400> SEQUENCE: 38

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys
            100                 105                 110
```

<210> SEQ ID NO 39
<211> LENGTH: 223
<212> TYPE: PRT
<213> ORGANISM: Artificial sequence
<220> FEATURE:
<223> OTHER INFORMATION: Synthetic Construct

<400> SEQUENCE: 39

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Glu Pro Asp
        35                  40                  45

Val Lys Phe Asn Trp Tyr Val Asp Gly Val Glu Val His Asn Ala Lys
    50                  55                  60
```

```
Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 40
<211> LENGTH: 7784
<212> TYPE: DNA
<213> ORGANISM: Artificial sequence
<220> FEATURE:
<223> OTHER INFORMATION: FI6 and CR8033 immunoadhesins
<220> FEATURE:
<221> NAME/KEY: polyA_signal
<222> LOCATION: (201)..(432)
<223> OTHER INFORMATION: complement - SV40\polyA
<220> FEATURE:
<221> NAME/KEY: misc_feature
<222> LOCATION: (453)..(1121)
<223> OTHER INFORMATION: complement - CH'2-3
<220> FEATURE:
<221> NAME/KEY: misc_feature
<222> LOCATION: (1125)..(1460)
<223> OTHER INFORMATION: complement - 033\VL
<220> FEATURE:
<221> NAME/KEY: misc_feature
<222> LOCATION: (1461)..(1505)
<223> OTHER INFORMATION: SL\from\3bn201co
<220> FEATURE:
<221> NAME/KEY: misc_feature
<222> LOCATION: (1506)..(1886)
<223> OTHER INFORMATION: complement - 033\VH
<220> FEATURE:
<221> NAME/KEY: misc_feature
<222> LOCATION: (1935)..(1946)
<223> OTHER INFORMATION: complement - leader
<220> FEATURE:
<221> NAME/KEY: misc_feature
<222> LOCATION: (2341)..(2382)
<223> OTHER INFORMATION: complement - CMV\mp2
<220> FEATURE:
<221> NAME/KEY: misc_feature
<222> LOCATION: (2383)..(2851)
<223> OTHER INFORMATION: enhancer
<220> FEATURE:
<221> NAME/KEY: misc_feature
<222> LOCATION: (2852)..(2977)
<223> OTHER INFORMATION: CMV\mp1
<220> FEATURE:
<221> NAME/KEY: misc_feature
<222> LOCATION: (3073)..(3045)
<223> OTHER INFORMATION: leader
<220> FEATURE:
<221> NAME/KEY: CDS
```

```
<222> LOCATION: (3094)..(3480)
<223> OTHER INFORMATION: FI6\VH
<220> FEATURE:
<221> NAME/KEY: misc_feature
<222> LOCATION: (3481)..(3525)
<223> OTHER INFORMATION: SL\from\3bn201co
<220> FEATURE:
<221> NAME/KEY: CDS
<222> LOCATION: (3526)..(3858)
<223> OTHER INFORMATION: FI6\VL
<220> FEATURE:
<221> NAME/KEY: misc_feature
<222> LOCATION: (3862)..(4530)
<223> OTHER INFORMATION: CH2-3
<220> FEATURE:
<221> NAME/KEY: polyA_signal
<222> LOCATION: (4551)..(4782)
<223> OTHER INFORMATION: SV40\polyA

<400> SEQUENCE: 40
```

| | | | | | |
|---|---|---|---|---|---|
| ggccttaatt | aggctgcgcg | ctcgctcgct | cactgaggcc | gcccgggcaa | agcccgggcg | 60 |
| tcgggcgacc | tttggtcgcc | cggcctcagt | gagcgagcga | gcgcgcagag | agggagtggc | 120 |
| caactccatc | actaggggtt | ccttgtagtt | aatgattaac | ccgccatgct | acttatctac | 180 |
| gtagccatgc | tctaggaaga | tcattttacc | acatttgtag | aggttttact | tgctttaaaa | 240 |
| aacctcccac | atctccccct | gaacctgaaa | cataaaatga | atgcaattgt | tgttgttaac | 300 |
| ttgtttattg | cagcttataa | tggttacaaa | taaagcaata | gcatcacaaa | tttcacaaat | 360 |
| aaagcatttt | tttcactgca | ttctagttgt | ggtttgtcca | aactcatcaa | tgtatcttat | 420 |
| catgtctgct | cgaagcggcc | gcaagcttat | cacttcccgg | ggctcaggct | cagggacttc | 480 |
| tgggtgtagt | ggttgtgcag | ggcctcgtgc | atcacgctgc | agctgaacac | gttgccctgc | 540 |
| tgccaccggc | tcttgtccac | ggtcagcttg | ctatacagga | agaatgagcc | gtcgctgtcc | 600 |
| agcacagggg | gggtggtctt | gtagttgttc | tcgggctggc | cgttgctctc | ccattccacg | 660 |
| gcgatctcgc | tggggtagaa | gcccttgacc | aggcaggtca | gggacacctg | gttcttggtc | 720 |
| atctcttccc | ggctgggggg | cagtgtgtag | acctgaggct | cgcggggctg | gcccttggcc | 780 |
| ttgctgatgg | ttttctcgat | gggggcaggc | agggccttgt | tggacacctt | gcacttgtac | 840 |
| tctttgccgt | tcagccagtc | ctggtgcagc | acggtcagca | cggacaccac | ccggtaggtg | 900 |
| ctgttgtact | gttcctctct | gggcttggtc | ttggcgttgt | gcacttccac | gccgtccacg | 960 |
| taccaattga | acttcacttc | agggtcctcg | tgggacacgt | ccaccaccac | gcaggtcact | 1020 |
| tcggggggtcc | ggctgatcat | cagggtgtcc | ttgggctttg | ggggaacag | gaacacgctg | 1080 |
| gggcctccca | gcagttcagg | ggcagggcag | ggggacacg | tggctagcac | cgtacgcttg | 1140 |
| atctccacct | tggttccctg | tccgaaggtc | caagggctgc | ttccgtactg | ctggcagtag | 1200 |
| tacacggcca | gatcctctgg | ctccagccgg | ctgatggtca | gggtgaaatc | ggttccgctt | 1260 |
| ccgcttccgc | tgaaccgggc | tgggattccg | gtggcccggg | tgctggctcc | gtagatcagc | 1320 |
| agccgtgggg | cctgtcctgg | cttctgctgg | taccaggcca | ggtagctgct | gctcacgctc | 1380 |
| tggctggccc | ggcagctcag | ggtggcccgc | tctcctgggc | tcaggctcag | ggttcctggg | 1440 |
| ctctgggtca | gcacgatctc | agatcccccg | cctccggacc | ctcctcctcc | gctgcctcct | 1500 |
| ccgccgctgc | tcacggtcac | catggttccc | tgtccccaga | tatcgaaggt | tcctccctcc | 1560 |
| aggatatcca | tggcgctgct | ctccagccga | tccttggcgc | agtagtacag | ggcggtatcc | 1620 |
| tcggcccgca | ggctgttcat | ctgcaggtac | aggctgttct | ttccgttatc | ccggctgatg | 1680 |
| gtgaaccgtc | cctgcacgct | atcggcgtat | cccatgaagt | ttcccttcca | gttgattccg | 1740 |

```
gccacccact ccagtccctt tcctggggcc tgccgcaccc agtgcatggt gtactcatcg    1800
aagctgaatc cgctggcggc gcagctcagc cgcaggctcc gtcctggctg caccagtcct    1860
cctccggtct ccaccagctg cacctctgaa ttcgtcacca gggccaggct cagggcgatc    1920
agcagcagca gctgcatgcg catggtgggg cggcagagtc gcgtccttgc tcgggtgttg    1980
taagttccag tgcaaagtgc cctagcctat agtgagtcgt attaagtact ctagccttaa    2040
gagctgtaat tgaactggga gtggacacct gtggagagaa aggcaaagtg gatgtcagta    2100
agaccaatag gtgcctatca gaaacgcaag agtcttctct gtctcgacaa gcccagtttc    2160
tattggtctc cttaaacctg tcttgtaacc ttgatactta cctgcccagt gcctcacgac    2220
caacttctgc agcttaagtt cgagactgtt gtgtcagaag cactgactgc gttagcaatt    2280
taactgtgat aaactaccgc ataaagctt ctagtgatct gacggttcac taaacgagct    2340
ctgcttatat aggcctccca ccgtacacgc cacctcgaca tacctagtta ttaatagtaa    2400
tcaattacgg ggtcattagt tcatagccca tatatggagt tccgcgttac ataacttacg    2460
gtaaatggcc cgcctggctg accgcccaac gacccccgcc cattgacgtc aataatgacg    2520
tatgttccca tagtaacgcc aatagggact ttccattgac gtcaatgggt ggagtattta    2580
cggtaaactg cccacttggc agtacatcaa gtgtatcata tgccaagtac gccccctatt    2640
gacgtcaatg acggtaaatg gcccgcctgg cattatgccc agtacatgac cttatgggac    2700
tttcctactt ggcagtacat ctacgtatta gtcatcgcta ttaccatggt gatgcggttt    2760
tggcagtaca tcaatgggcg tggatagcgg tttgactcac ggggatttcc aagtctccac    2820
cccattgacg tcaatgggag tttgttttgg caccaaaatc aacgggactt tccaaaatgt    2880
cgtaacaact ccgccccatt gacgcaaatg ggcggtaggc gtgtacggtg ggaggtctat    2940
ataagcagag ctggtttagt gaaccgtcag atccgctggg cactttgcac tggaacttac    3000
aacacccgag caaggacgcg actctgccgc cccaccatgc gcatgcagct gctgctgctg    3060
atcgccctga gcctggccct ggtgaccaac agc cag gtg caa ttg gtg gag agc    3114
                                   Gln Val Gln Leu Val Glu Ser
                                    1               5 gga gga gga gtg gtg cag cca gga cgg agc ctg cgg ctg agc tgc gcc    3162
Gly Gly Gly Val Val Gln Pro Gly Arg Ser Leu Arg Leu Ser Cys Ala
         10                  15                  20 gcc agc gga ttc acc ttc agc acc tac gcc atg cac tgg gtg cgg cag    3210
Ala Ser Gly Phe Thr Phe Ser Thr Tyr Ala Met His Trp Val Arg Gln
 25                  30                  35 gcc cca gga aag gga ctg gag tgg gtg gcc gtg atc agc tac gat gcc    3258
Ala Pro Gly Lys Gly Leu Glu Trp Val Ala Val Ile Ser Tyr Asp Ala
 40                  45                  50                  55 aac tac aag tac tac gcc gat agc gtg aag gga cgg ttc acc atc agc    3306
Asn Tyr Lys Tyr Tyr Ala Asp Ser Val Lys Gly Arg Phe Thr Ile Ser
                 60                  65                  70 cgg gat aac agc aag aac acc ctg tac ctg cag atg aac agc ctg cgg    3354
Arg Asp Asn Ser Lys Asn Thr Leu Tyr Leu Gln Met Asn Ser Leu Arg
             75                  80                  85 gcc gag gat acc gcc gtg tac tac tgc gcc aag gat agc cag ctg cgg    3402
Ala Glu Asp Thr Ala Val Tyr Tyr Cys Ala Lys Asp Ser Gln Leu Arg
         90                  95                 100 agc ctg ctg tac ttc gag tgg ctg agc cag gga tac ttc gat tac tgg    3450
Ser Leu Leu Tyr Phe Glu Trp Leu Ser Gln Gly Tyr Phe Asp Tyr Trp
    105                 110                 115 gga cag gga acc ctg gtg acc gtg agc agc ggcggaggag gcagcggagg    3500
Gly Gln Gly Thr Leu Val Thr Val Ser Ser
120                 125
```

```
aggagggtcc ggaggcgggg gatct gat atc gtc atg acc cag agc cca gat      3552
                              Asp Ile Val Met Thr Gln Ser Pro Asp
                              130             135 agc ctg gcc gtg agc ctg gga gag cgg gcc acc atc aac tgc aag agc      3600
Ser Leu Ala Val Ser Leu Gly Glu Arg Ala Thr Ile Asn Cys Lys Ser
140                 145                 150 agc cag agc gtg acc ttc aac tac aag aac tac ctg gcc tgg tac cag      3648
Ser Gln Ser Val Thr Phe Asn Tyr Lys Asn Tyr Leu Ala Trp Tyr Gln
155                 160                 165                 170 cag aag cca gga cag cca cca aag ctg ctg atc tac tgg gcc agc acc      3696
Gln Lys Pro Gly Gln Pro Pro Lys Leu Leu Ile Tyr Trp Ala Ser Thr
                175                 180                 185 cgg gag agc gga gtg cca gat cgg ttc agc gga agc gga agc gga acc      3744
Arg Glu Ser Gly Val Pro Asp Arg Phe Ser Gly Ser Gly Ser Gly Thr
                190                 195                 200 gat ttc acc ctg acc atc agc agc ctg cag gcc gag gat gtg gcc gtg      3792
Asp Phe Thr Leu Thr Ile Ser Ser Leu Gln Ala Glu Asp Val Ala Val
                205                 210                 215 tac tac tgc cag cag cac tac cgg acc cca cca acc ttc gga cag gga      3840
Tyr Tyr Cys Gln Gln His Tyr Arg Thr Pro Pro Thr Phe Gly Gln Gly
220                 225                 230 acc aag gtg gag atc aag gccacgtgcc ctccatgtcc agcccccgaa             3888
Thr Lys Val Glu Ile Lys
235                 240 ctgctgggcg ggcctagcgt gttcctgttt cccctaagc ctaaagatac actgatgatt     3948
agtagaaccc cagaggtcac atgcgtggtc gtggacgtgt cccacgaaga gcctgacgtg    4008
aagttcaact ggtacgtgga tggcgtggag gtgcacaatg ctaagactaa accacgcgaa    4068
gagcagtata atagtacata ccgagtcgtg tcagtcctga cagtgctgca ccaggattgg    4128
ctgaacggca aggagtataa gtgcaaggtg tctaacaagg ccctgccgc ccctatcgag     4188
aaaacaatta gcaaggccaa agggcagcca cgggaacccc aggtctacac tctgccaccc    4248
tcaagagatg aactgactaa gaaccaggtc agcctgacct gtctggtgaa aggcttctac    4308
cccagcgaca tcgccgtgga gtgggaaagt aacggccagc ctgagaataa ctacaagact    4368
accccctccag tgctggatag cgacgggtcc ttcttcctgt atagcaagct gacagtggac    4428
aaatcccgct ggcagcaggg aaacgtcttt tcctgttctg tgatgcatga ggccctgcac    4488
aatcattaca cccagaagag tctgtcactg agccccggca atgataagc ttgcggccgc     4548
ttcgagcaga catgataaga tacattgatg agtttggaca accacaact agaatgcagt     4608
gaaaaaaatg ctttatttgt gaaatttgtg atgctattgc tttatttgta accattataa    4668
gctgcaataa acaagttaac aacaacaatt gcattcattt tatgtttcag gttcaggggg    4728
agatgtggga ggttttttaa agcaagtaaa acctctacaa atgtggtaaa atcgataagg    4788
atcttcctag agcatggcta cgtagataag tagcatggcg ggttaatcat taactacaag    4848
gaaccctag tgatggagtt ggccactccc tctctgcgcg ctcgctcgct cactgaggcc     4908
gggcgaccaa aggtcgcccg acgcccgggc tttgcccggg cggcctcagt gagcgagcga    4968
gcgcgcagcc ttaattaacc taattcactg gccgtcgttt tacaacgtcg tgactgggaa    5028
aaccctggcg ttacccaact taatcgcctt gcagcacatc ccctttcgc cagctggcgt     5088
aatagcgaag aggcccgcac cgatcgccct tcccaacagt tgcgcagcct gaatggcgaa    5148
tgggacgcgc cctgtagcgg cgcattaagc gcggcgggtg tggtggttac gcgcagcgtg    5208
accgctacac ttgccagcgc cctagcgccc gctcctttcg ctttcttccc ttcctttctc    5268
```

```
gccacgttcg ccggctttcc ccgtcaagct ctaaatcggg ggctccctttt agggttccga    5328 tttagtgctt tacggcacct cgaccccaaa aaacttgatt agggtgatgg ttcacgtagt    5388
gggccatcgc cctgatagac ggttttttcgc cctttgacgt tggagtccac gttctttaat    5448
agtggactct tgttccaaac tggaacaaca ctcaaccctta tctcggtcta ttcttttgat    5508
ttataaggga ttttgccgat tcggcctat tggttaaaaa atgagctgat ttaacaaaaa    5568
tttaacgcga atttttaacaa aatattaacg cttacaattt aggtggcact tttcggggaa    5628
atgtgcgcgg aaccccctatt tgttttatttt tctaaataca ttcaaatatg tatccgctca    5688
tgagacaata acccctgataa atgcttcaat aatattgaaa aaggaagagt atgagtattc    5748
aacatttccg tgtcgccctt attcccttttt ttgcggcatt ttgccttcct gtttttgctc    5808
acccagaaac gctggtgaaa gtaaaagatg ctgaagatca gttgggtgca cgagtgggtt    5868
acatcgaact ggatctcaac agcggtaaga tccttgagag ttttcgcccc gaagaacgtt    5928
ttccaatgat gagcactttt aaagttctgc tatgtggcgc ggtattatcc cgtattgacg    5988
ccgggcaaga gcaactcggt cgccgcatac actattctca gaatgacttg gttgagtact    6048
caccagtcac agaaaagcat cttacggatg gcatgacagt aagagaatta tgcagtgctg    6108
ccataaccat gagtgataac actgcggcca acttacttct gacaacgatc ggaggaccga    6168
aggagctaac cgcttttttg cacaacatgg gggatcatgt aactcgcctt gatcgttggg    6228
aaccggagct gaatgaagcc ataccaaacg acgagcgtga caccacgatg cctgtagcaa    6288
tggcaacaac gttgcgcaaa ctattaactg gcgaactact tactctagct tcccggcaac    6348
aattaataga ctggatggag gcggataaag ttgcaggacc acttctgcgc tcggcccttc    6408
cggctggctg gtttattgct gataaatctg gagccggtga gcgtgggtct cgcggtatca    6468
ttgcagcact ggggccagat ggtaagccct cccgtatcgt agttatctac acgacgggga    6528
gtcaggcaac tatggatgaa cgaaatagac agatcgctga gataggtgcc tcactgatta    6588
agcattggta actgtcagac caagtttact catatatact ttagattgat ttaaaacttc    6648
atttttaatt taaaaggatc taggtgaaga tccttttttga taatctcatg accaaaatcc    6708
cttaacgtga gttttcgttc cactgagcgt cagaccccgt agaaaagatc aaaggatctt    6768
cttgagatcc tttttttctg cgcgtaatct gctgcttgca acaaaaaaa ccaccgctac    6828 cagcggtggt ttgtttgccg gatcaagagc taccaactct ttttccgaag gtaactggct    6888
tcagcagagc gcagatacca aatactgttc ttctagtgta gccgtagtta ggccaccact    6948
tcaagaactc tgtagcaccg cctacatacc tcgctctgct aatcctgtta ccagtggctg    7008
ctgccagtgg cgataagtcg tgtcttaccg ggttggactc aagacgatag ttaccggata    7068
aggcgcagcg gtcgggctga acggggggtt cgtgcacaca gcccagcttg gagcgaacga    7128
cctacaccga actgagatac ctacagcgtg agctatgaga aagcgccacg cttcccgaag    7188
ggagaaaggc ggacaggtat ccggtaagcg gcagggtcgg aacaggagag cgcacgaggg    7248
agcttccagg gggaaacgcc tggtatcttt atagtcctgt cgggtttcgc cacctctgac    7308
ttgagcgtcg atttttgtga tgctcgtcag ggggcggag cctatggaaa aacgccagca    7368
acgcggcctt tttacggttc ctggccttttt gctggccttt tgctcacatg ttctttcctg    7428
cgttatcccc tgattctgtg gataaccgta ttaccgcctt tgagtgagct gataccgctc    7488
gccgcagccg aacgaccgag cgcagcgagt cagtgagcga ggaagcggaa gagcgcccaa    7548
tacgcaaacc gcctctcccc gcgcgttggc cgattcatta atgcagctgg cacgacaggt    7608
ttcccgactg gaaagcgggc agtgagcgca acgcaattaa tgtgagttag ctcactcatt    7668
```
aggcacccca ggctttacac tttatgcttc cggctcgtat gttgtgtgga attgtgagcg    7728
gataacaatt tcacacagga aacagctatg accatgatta cgccagattt aattaa    7784

<210> SEQ ID NO 41
<211> LENGTH: 129
<212> TYPE: PRT
<213> ORGANISM: Artificial sequence
<220> FEATURE:
<223> OTHER INFORMATION: Synthetic Construct

<400> SEQUENCE: 41

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 42
<211> LENGTH: 111
<212> TYPE: PRT
<213> ORGANISM: Artificial sequence
<220> FEATURE:
<223> OTHER INFORMATION: Synthetic Construct

<400> SEQUENCE: 42

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys
            100                 105                 110

<210> SEQ ID NO 43
<211> LENGTH: 7782
<212> TYPE: DNA
<213> ORGANISM: Artificial sequence
<220> FEATURE:
<223> OTHER INFORMATION: Plasmid carrying TCN032 and Fi6 monoclonal

```
                  antibodies
<220> FEATURE:
<221> NAME/KEY: repeat_region
<222> LOCATION: (14)..(143)
<220> FEATURE:
<221> NAME/KEY: polyA_signal
<222> LOCATION: (204)..(252)
<223> OTHER INFORMATION: synthetic polyA
<220> FEATURE:
<221> NAME/KEY: misc_feature
<222> LOCATION: (261)..(267)
<223> OTHER INFORMATION: stop cassette (complement)
<220> FEATURE:
<221> NAME/KEY: misc_feature
<222> LOCATION: (268)..(588)
<223> OTHER INFORMATION: constant light (on complementary strand)
<220> FEATURE:
<221> NAME/KEY: misc_feature
<222> LOCATION: (967)..(971)
<223> OTHER INFORMATION: Kozak (located on complementary strand)
<220> FEATURE:
<221> NAME/KEY: misc_feature
<222> LOCATION: (972)..(1019)
<223> OTHER INFORMATION: c-myc 5' UTR (located on complementary strand)
<220> FEATURE:
<221> NAME/KEY: misc_feature
<222> LOCATION: (1026)..(1094)
<223> OTHER INFORMATION: CMV\mp2
<220> FEATURE:
<221> NAME/KEY: enhancer
<222> LOCATION: (1026)..(1094)
<220> FEATURE:
<221> NAME/KEY: misc_feature
<222> LOCATION: (1564)..(1689)
<220> FEATURE:
<221> NAME/KEY: misc_feature
<222> LOCATION: (1696)..(1743)
<223> OTHER INFORMATION: c-myc 5' UTR
<220> FEATURE:
<221> NAME/KEY: misc_feature
<222> LOCATION: (1744)..(1748)
<223> OTHER INFORMATION: Kozak
<220> FEATURE:
<221> NAME/KEY: misc_feature
<222> LOCATION: (1749)..(1805)
<223> OTHER INFORMATION: leader
<220> FEATURE:
<221> NAME/KEY: CDS
<222> LOCATION: (1806)..(2165)
<223> OTHER INFORMATION: TCN032 variable heavy
<220> FEATURE:
<221> NAME/KEY: repeat_region
<222> LOCATION: (1845)..(4974)
<223> OTHER INFORMATION: inverted terminal repeat
<220> FEATURE:
<221> NAME/KEY: repeat_region
<222> LOCATION: (1845)..(4974)
<223> OTHER INFORMATION: inverted terminal repeat (located on
      complement)
<220> FEATURE:
<221> NAME/KEY: CDS
<222> LOCATION: (2166)..(2459)
<223> OTHER INFORMATION: CH1
<220> FEATURE:
<221> NAME/KEY: misc
<222> LOCATION: (2166)..(2459)
<223> OTHER INFORMATION: CH1
<220> FEATURE:
<221> NAME/KEY: CDS
<222> LOCATION: (2460)..(3152)
<223> OTHER INFORMATION: hinge-CH2'-CH3'
<220> FEATURE:
<221> NAME/KEY: misc_feature
<222> LOCATION: (3153)..(3164)
<223> OTHER INFORMATION: furin cleavage site
<220> FEATURE:
<221> NAME/KEY: misc_feature
<222> LOCATION: (3165)..(3236)
<223> OTHER INFORMATION: F2A linker
```

```
<220> FEATURE:
<221> NAME/KEY: misc_feature
<222> LOCATION: (3239)..(3296)
<220> FEATURE:
<221> NAME/KEY: misc_feature
<222> LOCATION: (3239)..(3296)
<220> FEATURE:
<221> NAME/KEY: CDS
<222> LOCATION: (3297)..(3683)
<223> OTHER INFORMATION: FI6 VH
<220> FEATURE:
<221> NAME/KEY: CDS
<222> LOCATION: (3684)..(4004)
<223> OTHER INFORMATION: CH1
<220> FEATURE:
<221> NAME/KEY: CDS
<222> LOCATION: (4005)..(4673)
<223> OTHER INFORMATION: CH2-3
<220> FEATURE:
<221> NAME/KEY: misc_feature
<222> LOCATION: (4674)..(4680)
<223> OTHER INFORMATION: Stop cassette
<220> FEATURE:
<221> NAME/KEY: misc_feature
<222> LOCATION: (4674)..(4680)
<220> FEATURE:
<221> NAME/KEY: polyA_signal
<222> LOCATION: (4693)..(4770)
<223> OTHER INFORMATION: TKpAshort
<220> FEATURE:
<221> NAME/KEY: rep_origin
<222> LOCATION: (5151)..(5606)
<220> FEATURE:
<221> NAME/KEY: CDS
<222> LOCATION: (5737)..(6594)
<223> OTHER INFORMATION: Amp-R
<220> FEATURE:
<221> NAME/KEY: misc_feature
<222> LOCATION: (6768)..(.7356)
<223> OTHER INFORMATION: col\E1\origin

<400> SEQUENCE: 43
```

| | | | | | |
|---|---|---|---|---|---|
| ggccttaatt | aggctgcgcg | ctcgctcgct | cactgaggcc | gcccgggcaa | agcccgggcg | 60 |
| tcgggcgacc | tttggtcgcc | cggcctcagt | gagcgagcga | gcgcgcagag | agggagtggc | 120 |
| caactccatc | actaggggtt | ccttgtagtt | aatgattaac | cgccatgct | acttatctac | 180 |
| gtagccatgc | tctaggaaga | tctcacacaa | aaaaccaaca | cacagatgta | atgaaaataa | 240 |
| agatatttta | ttgcggccgc | tttatcagca | ctctccgcgg | ttgaagctct | tggtcactgg | 300 |
| gctgctcagt | ccctggtggg | tcacctcgca | ggcgtacacc | ttgtgcttct | cgtaatcggc | 360 |
| cttgctcagg | gtcagggtgc | tgctcaggct | gtaggtgcta | tccttgctat | cctgctcggt | 420 |
| cacgctctcc | tggctgtttc | cgctctgcag | ggcgttatcc | accttccact | gcaccttggc | 480 |
| ctcccgtggg | tagaagttgt | tcagcaggca | caccacgctg | gcggttccgc | tcttcagctg | 540 |
| ctcatcgctt | ggtgggaaga | tgaacacgct | tgggcggcc | accgtacgct | tgatctccac | 600 |
| ccgggttcct | cctccgaagg | tcagtggtgg | gctgtagctc | tgctggcagt | agtaggtggc | 660 |
| gaaatcctct | ggctgcaggc | tggtgatggt | cagggtgaaa | tcggttccgc | ttccgcttcc | 720 |
| gctgaaccgg | cttggcactc | cgctctgcag | tccgctggcg | gcgctgatca | gtcccttgg | 780 |
| ggcctttcct | ggccgctgct | ggtaccagtt | caggtacttg | tagatgttct | ggctggcccg | 840 |
| gcaggtgatg | gtcacccgat | ctcccacgct | ggcgctcagg | ctgcttgggc | tctgggtcat | 900 |
| ctggatatcg | ctgttggtca | ccagggccag | gctcagggcg | atcagcagca | gcagctgcat | 960 |
| tctcatggtg | gagagtcgcg | tccttgctcg | ggtgttgtaa | gttccagtgc | aaagtgcccc | 1020 |
| aattggcgat | ctgacggttc | actaaacgag | ctctgcttat | ataggcctcc | caccgtacac | 1080 |

```
gccacctcga catacctagt tattaatagt aatcaattac ggggtcatta gttcatagcc      1140
catatatgga gttccgcgtt acataactta cggtaaatgg cccgcctggc tgaccgccca      1200
acgaccccg cccattgacg tcaataatga cgtatgttcc catagtaacg ccaataggga      1260
ctttccattg acgtcaatgg gtggagtatt tacggtaaac tgcccacttg gcagtacatc      1320
aagtgtatca tatgccaagt acgccccta ttgacgtcaa tgacggtaaa tggcccgcct       1380
ggcattatgc ccagtacatg accttatggg actttcctac ttggcagtac atctacgtat      1440
tagtcatcgc tattaccatg gtgatgcggt tttggcagta catcaatggg cgtggatagc      1500
ggtttgactc acggggattt ccaagtctcc accccattga cgtcaatggg agtttgtttt      1560
ggcaccaaaa tcaacgggac tttccaaaat gtcgtaacaa ctccgcccca ttgacgcaaa      1620
tgggcggtag gcgtgtacgg tgggaggtct atataagcag agctggttta gtgaaccgtc      1680
agatccgctg ctagcgggca ctttgcactg gaacttacaa caccgagca aggacgcgac       1740
tctccaccat gcgcatgcag ctgctgctgc tgatcgccct gagcctggcc ctggtgacca      1800
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| acagc | cag | gtg | cag | ctg | cag | gag | agc | gga | cca | gga | ctg | gtg | aag | cca | agc | 1850 |
|       | Gln | Val | Gln | Leu | Gln | Glu | Ser | Gly | Pro | Gly | Leu | Val | Lys | Pro | Ser |      |
|       | 1   |     |     |     | 5   |     |     |     |     | 10  |     |     |     |     | 15  |      |
| gag acc ctg agc ctg acc tgc acc gtg agc gga agc agc atc agc aac | 1898 |
| Glu Thr Leu Ser Leu Thr Cys Thr Val Ser Gly Ser Ser Ile Ser Asn |      |
|                     20                  25                  30  |      |
| tac tac tgg agc tgg atc cgg cag agc cca gga aag gga ctg gag tgg | 1946 |
| Tyr Tyr Trp Ser Trp Ile Arg Gln Ser Pro Gly Lys Gly Leu Glu Trp |      |
|                 35                  40                  45      |      |
| atc gga ttc atc tac tac gga gga aac acc aag tac aac cca agc ctg | 1994 |
| Ile Gly Phe Ile Tyr Tyr Gly Gly Asn Thr Lys Tyr Asn Pro Ser Leu |      |
|             50                  55                  60          |      |
| aag agc cgg gtg acc atc agc cag gat acc agc aag agc cag gtg agc | 2042 |
| Lys Ser Arg Val Thr Ile Ser Gln Asp Thr Ser Lys Ser Gln Val Ser |      |
|         65                  70                  75              |      |
| ctg acc atg agc agc gtg acc gcc gcc gag agc gcc gtg tac ttc tgc | 2090 |
| Leu Thr Met Ser Ser Val Thr Ala Ala Glu Ser Ala Val Tyr Phe Cys |      |
| 80                  85                  90                  95  |      |
| gcc cgg gcc agc tgc agc gga gga tac tgc atc ctg gat tac tgg gga | 2138 |
| Ala Arg Ala Ser Cys Ser Gly Gly Tyr Cys Ile Leu Asp Tyr Trp Gly |      |
|                 100                 105                 110     |      |
| cag gga acc ctg gtg acc gtg agc agc gcg tcg acc aag gga cct tcg | 2186 |
| Gln Gly Thr Leu Val Thr Val Ser Ser Ala Ser Thr Lys Gly Pro Ser |      |
|             115                 120                 125         |      |
| gtc ttc ccc ctg gca ccc tcc tcc aag agc acc tct ggg ggc aca gcg | 2234 |
| Val Phe Pro Leu Ala Pro Ser Ser Lys Ser Thr Ser Gly Gly Thr Ala |      |
|         130                 135                 140             |      |
| gcc ctg ggc tgc ctg gtc aag gac tac ttc ccc gaa ccg gtg acg gtg | 2282 |
| Ala Leu Gly Cys Leu Val Lys Asp Tyr Phe Pro Glu Pro Val Thr Val |      |
|     145                 150                 155                 |      |
| tcg tgg aac tca ggc gcc ctg acc agc ggc gtg cac acc ttc ccg gct | 2330 |
| Ser Trp Asn Ser Gly Ala Leu Thr Ser Gly Val His Thr Phe Pro Ala |      |
| 160                 165                 170                 175 |      |
| gtc cta cag tcc tca gga ctc tac tcc ctc agc agc gtg gtg acc gtg | 2378 |
| Val Leu Gln Ser Ser Gly Leu Tyr Ser Leu Ser Ser Val Val Thr Val |      |
|                 180                 185                 190     |      |
| ccc tcc agc agc ttg ggc acc cag acc tac atc tgc aac gtg aat cac | 2426 |
| Pro Ser Ser Ser Leu Gly Thr Gln Thr Tyr Ile Cys Asn Val Asn His |      |
|             195                 200                 205         |      |
| aag ccc agc aac acc aag gtg gac aag aaa gtt gaa cca aag agc tgc | 2474 |
| Lys Pro Ser Asn Thr Lys Val Asp Lys Lys Val Glu Pro Lys Ser Cys |      |
|         210                 215                 220             |      |

-continued

```
gac aag acc cac acg tgt ccc ccc tgc cct gcc cct gaa ctg ctg gga      2522
Asp Lys Thr His Thr Cys Pro Pro Cys Pro Ala Pro Glu Leu Leu Gly
    225                 230                 235 ggc ccc agc gtg ttc ctg ttc ccc cca aag ccc aag gac acc ctg atg      2570
Gly Pro Ser Val Phe Leu Phe Pro Pro Lys Pro Lys Asp Thr Leu Met
240                 245                 250                 255 atc agc cgg acc ccc gaa gtg acc tgc gtg gtg gtg gac gtg tcc cac      2618
Ile Ser Arg Thr Pro Glu Val Thr Cys Val Val Val Asp Val Ser His
                260                 265                 270 gag gac cct gaa gtg aag ttt aat tgg tac gtg gac ggc gtg gaa gtg      2666
Glu Asp Pro Glu Val Lys Phe Asn Trp Tyr Val Asp Gly Val Glu Val
            275                 280                 285 cac aac gcc aag acc aag ccc aga gag gaa cag tac aac agc acc tac      2714
His Asn Ala Lys Thr Lys Pro Arg Glu Glu Gln Tyr Asn Ser Thr Tyr
        290                 295                 300 cgg gtg gtg tcc gtg ctg acc gtg ctg cac cag gac tgg ctg aac ggc      2762
Arg Val Val Ser Val Leu Thr Val Leu His Gln Asp Trp Leu Asn Gly
305                 310                 315 aaa gag tac aag tgc aag gtg tcc aac aag gcc ctg cct gcc ccc atc      2810
Lys Glu Tyr Lys Cys Lys Val Ser Asn Lys Ala Leu Pro Ala Pro Ile
320                 325                 330                 335 gag aaa acc atc agc aag gcc aag ggc cag ccc cgc gag cct cag gtc      2858
Glu Lys Thr Ile Ser Lys Ala Lys Gly Gln Pro Arg Glu Pro Gln Val
                340                 345                 350 tac aca ctg ccc ccc agc cgg gaa gag atg acc aag aac cag gtg tcc      2906
Tyr Thr Leu Pro Pro Ser Arg Glu Glu Met Thr Lys Asn Gln Val Ser
            355                 360                 365 ctg acc tgc ctg gtc aag ggc ttc tac ccc agc gac atc gcc gtg gaa      2954
Leu Thr Cys Leu Val Lys Gly Phe Tyr Pro Ser Asp Ile Ala Val Glu
        370                 375                 380 tgg gag agc aac ggc cag ccc gag aac aac tac aag acc acc ccc cct      3002
Trp Glu Ser Asn Gly Gln Pro Glu Asn Asn Tyr Lys Thr Thr Pro Pro
385                 390                 395 gtg ctg gac agc gac ggc tca ttc ttc ctg tat agc aag ctg acc gtg      3050
Val Leu Asp Ser Asp Gly Ser Phe Phe Leu Tyr Ser Lys Leu Thr Val
400                 405                 410                 415 gac aag agc cgg tgg cag cag ggc aac gtg ttc agc tgc agc gtg atg      3098
Asp Lys Ser Arg Trp Gln Gln Gly Asn Val Phe Ser Cys Ser Val Met
                420                 425                 430 cac gag gcc ctg cac aac cac tac acc cag aag tcc ctg agc ctg agc      3146
His Glu Ala Leu His Asn His Tyr Thr Gln Lys Ser Leu Ser Leu Ser
            435                 440                 445 ccc ggc agaaagcgga gagccccgt gaagcagacc ctgaacttcg acctgctgaa       3202
Pro Gly gctggccggc gacgtggaaa gcaaccctgg ccctatgtac agaatgcagc tgctgagctg   3262
catcgccctg agcctggccc tggtgaccaa cagc cag gtg caa cta gtg gag agc   3317
                                      Gln Val Gln Leu Val Glu Ser
                                              450                 455 gga gga gga gtg gtg cag cca gga cgg agc ctg cgg ctg agc tgc gcc      3365
Gly Gly Gly Val Val Gln Pro Gly Arg Ser Leu Arg Leu Ser Cys Ala
            460                 465                 470 gcc agc gga ttc acc ttc agc acc tac gcc atg cac tgg gtg cgg cag      3413
Ala Ser Gly Phe Thr Phe Ser Thr Tyr Ala Met His Trp Val Arg Gln
        475                 480                 485 gcc cca gga aag gga ctg gag tgg gtg gcc gtg atc agc tac gat gcc      3461
Ala Pro Gly Lys Gly Leu Glu Trp Val Ala Val Ile Ser Tyr Asp Ala
    490                 495                 500 aac tac aag tac tac gcc gat agc gtg aag gga cgg ttc acc atc agc      3509
Asn Tyr Lys Tyr Tyr Ala Asp Ser Val Lys Gly Arg Phe Thr Ile Ser
```

```
                Asn Tyr Lys Tyr Tyr Ala Asp Ser Val Lys Gly Arg Phe Thr Ile Ser
                505                 510                 515                 520 cgg gat aac agc aag aac acc ctg tac ctg cag atg aac agc ctg cgg        3557
Arg Asp Asn Ser Lys Asn Thr Leu Tyr Leu Gln Met Asn Ser Leu Arg
                    525                 530                 535 gcc gag gat acc gcc gtg tac tac tgc gcc aag gat agc cag ctg cgg        3605
Ala Glu Asp Thr Ala Val Tyr Tyr Cys Ala Lys Asp Ser Gln Leu Arg
540                 545                 550 agc ctg ctg tac ttc gag tgg ctg agc cag gga tac ttc gat tac tgg        3653
Ser Leu Leu Tyr Phe Glu Trp Leu Ser Gln Gly Tyr Phe Asp Tyr Trp
            555                 560                 565 gga cag gga acc ctg gtg acc gtg agc agc gcc agc acc aag ggg ccc        3701
Gly Gln Gly Thr Leu Val Thr Val Ser Ser Ala Ser Thr Lys Gly Pro
        570                 575                 580 agc gtg ttc cca ctg gcc cca agc agc aag agc acc agc gga gga acc        3749
Ser Val Phe Pro Leu Ala Pro Ser Ser Lys Ser Thr Ser Gly Gly Thr
585                 590                 595                 600 gcc gcc ctg gga tgc ctg gtg aag gat tac ttc cca gag cca gtg acc        3797
Ala Ala Leu Gly Cys Leu Val Lys Asp Tyr Phe Pro Glu Pro Val Thr
                    605                 610                 615 gtg agc tgg aac agc gga gcc ctg acc agc gga gtg cac acc ttc cca        3845
Val Ser Trp Asn Ser Gly Ala Leu Thr Ser Gly Val His Thr Phe Pro
                620                 625                 630 gcc gtg ctg cag agc agc gga ctg tat agc ctg agc agc gtg gtg acc        3893
Ala Val Leu Gln Ser Ser Gly Leu Tyr Ser Leu Ser Ser Val Val Thr
            635                 640                 645 gtg cca agc agc agc ctg gga acc cag acc tac atc tgc aac gtg aac        3941
Val Pro Ser Ser Ser Leu Gly Thr Gln Thr Tyr Ile Cys Asn Val Asn
        650                 655                 660 cac aag cca agc aac acc aag gtg gat aag aag gtg gag cca aag agc        3989
His Lys Pro Ser Asn Thr Lys Val Asp Lys Lys Val Glu Pro Lys Ser
665                 670                 675                 680 tgc gat aag acc cac acg tgc cct cca tgt cca gcc ccc gaa ctg ctg        4037
Cys Asp Lys Thr His Thr Cys Pro Pro Cys Pro Ala Pro Glu Leu Leu
                    685                 690                 695 ggc ggg cct agc gtg ttc ctg ttt ccc cct aag cct aaa gat aca ctg        4085
Gly Gly Pro Ser Val Phe Leu Phe Pro Pro Lys Pro Lys Asp Thr Leu
                700                 705                 710 atg att agt aga acc cca gag gtc aca tgc gtg gtc gtg gac gtg tcc        4133
Met Ile Ser Arg Thr Pro Glu Val Thr Cys Val Val Val Asp Val Ser
            715                 720                 725 cac gaa gag cct gac gtg aag ttc aac tgg tac gtg gat ggc gtg gag        4181
His Glu Glu Pro Asp Val Lys Phe Asn Trp Tyr Val Asp Gly Val Glu
        730                 735                 740 gtg cac aat gct aag act aaa cca cgc gaa gag cag tat aat agt aca        4229
Val His Asn Ala Lys Thr Lys Pro Arg Glu Glu Gln Tyr Asn Ser Thr
745                 750                 755                 760 tac cga gtc gtg tca gtc ctg aca gtg ctg cac cag gat tgg ctg aac        4277
Tyr Arg Val Val Ser Val Leu Thr Val Leu His Gln Asp Trp Leu Asn
                    765                 770                 775 ggc aag gag tat aag tgc aag gtg tct aac aag gcc ctg ccc gcc cct        4325
Gly Lys Glu Tyr Lys Cys Lys Val Ser Asn Lys Ala Leu Pro Ala Pro
                780                 785                 790 atc gag aaa aca att agc aag gcc aaa ggg cag cca cgg gaa ccc cag        4373
Ile Glu Lys Thr Ile Ser Lys Ala Lys Gly Gln Pro Arg Glu Pro Gln
            795                 800                 805 gtc tac act ctg cca ccc tca aga gat gaa ctg act aag aac cag gtc        4421
Val Tyr Thr Leu Pro Pro Ser Arg Asp Glu Leu Thr Lys Asn Gln Val
        810                 815                 820
```

-continued

```
agc ctg acc tgt ctg gtg aaa ggc ttc tac ccc agc gac atc gcc gtg     4469
Ser Leu Thr Cys Leu Val Lys Gly Phe Tyr Pro Ser Asp Ile Ala Val
825                 830                 835                 840 gag tgg gaa agt aac ggc cag cct gag aat aac tac aag act acc cct     4517
Glu Trp Glu Ser Asn Gly Gln Pro Glu Asn Asn Tyr Lys Thr Thr Pro
        845                 850                 855 cca gtg ctg gat agc gac ggg tcc ttc ttc ctg tat agc aag ctg aca     4565
Pro Val Leu Asp Ser Asp Gly Ser Phe Phe Leu Tyr Ser Lys Leu Thr
            860                 865                 870 gtg gac aaa tcc cgc tgg cag cag gga aac gtc ttt tcc tgt tct gtg     4613
Val Asp Lys Ser Arg Trp Gln Gln Gly Asn Val Phe Ser Cys Ser Val
                875                 880                 885 atg cat gag gcc ctg cac aat cat tac acc cag aag agt ctg tca ctg     4661
Met His Glu Ala Leu His Asn His Tyr Thr Gln Lys Ser Leu Ser Leu
            890                 895                 900 agc ccc ggc aaa tgataaaaag cttctcgaga aggaacccgc gctatgacgg         4713
Ser Pro Gly Lys
905 caataaaaag acagaataaa acccacgggt gttgggtcgt ttgttcataa acccgggaag   4773 cttatcgata aggatcttcc tagagcatgg ctacgtagat aagtagcatg gcgggttaat   4833 cattaactac aaggaacccc tagtgatgga gttggccact ccctctctgc gcgctcgctc   4893 gctcactgag gccgggcgac caaaggtcgc ccgacgcccg gctttgccc gggcggcctc    4953 agtgagcgag cgagcgcgca gccttaatta acctaattca ctggccgtcg ttttacaacg   5013 tcgtgactgg gaaaaccctg gcgttaccca acttaatcgc cttgcagcac atccccttt    5073 cgccagctgg cgtaatagcg aagaggcccg caccgatcgc ccttcccaac agttgcgcag   5133 cctgaatggc gaatgggacg cgccctgtag cggcgcatta agcgcggcgg gtgtggtggt   5193 tacgcgcagc gtgaccgcta cacttgccag cgccctagcg cccgctcctt tcgctttctt   5253 cccttccttt ctcgccacgt tcgccggctt tccccgtcaa gctctaaatc ggggggctccc  5313 tttagggttc cgatttagtg ctttacggca cctcgacccc aaaaaacttg attagggtga   5373 tggttcacgt agtgggccat cgccctgata acggtttttt cgccctttga cgttggagtc   5433 cacgttcttt aatagtggac tcttgttcca aactggaaca cactcaacc ctatctcggt    5493 ctattctttt gatttataag ggattttgcc gatttcggcc tattggttaa aaatgagct    5553 gatttaacaa aaatttaacg cgaattttaa caaaatatta acgcttacaa tttaggtggc   5613 acttttcggg gaaatgtgcg cggaacccct atttgtttat ttttctaaat acattcaaat   5673 atgtatccgc tcatgagaca ataaccctga taaatgcttc aataatattg aaaaaggaag   5733 agt atg agt att caa cat ttc cgt gtc gcc ctt att ccc ttt ttt gcg     5781
    Met Ser Ile Gln His Phe Arg Val Ala Leu Ile Pro Phe Phe Ala
    910                 915                 920 gca ttt tgc ctt cct gtt ttt gct cac cca gaa acg ctg gtg aaa gta     5829
Ala Phe Cys Leu Pro Val Phe Ala His Pro Glu Thr Leu Val Lys Val
925                 930                 935 aaa gat gct gaa gat cag ttg ggt gca cga gtg ggt tac atc gaa ctg     5877
Lys Asp Ala Glu Asp Gln Leu Gly Ala Arg Val Gly Tyr Ile Glu Leu
940                 945                 950                 955 gat ctc aac agc ggt aag atc ctt gag agt ttt cgc ccc gaa gaa cgt     5925
Asp Leu Asn Ser Gly Lys Ile Leu Glu Ser Phe Arg Pro Glu Glu Arg
                960                 965                 970 ttt cca atg atg agc act ttt aaa gtt ctg cta tgt ggc gcg gta tta     5973
Phe Pro Met Met Ser Thr Phe Lys Val Leu Leu Cys Gly Ala Val Leu
                975                 980                 985 tcc cgt att gac gcc ggg caa gag caa ctc ggt cgc cgc ata cac tat     6021
```

|  |  |  |  |  |  |  |  |  |  |  |  |  |
|--|--|--|--|--|--|--|--|--|--|--|--|--|
| Ser | Arg | Ile | Asp | Ala | Gly | Gln | Glu | Gln | Leu | Gly | Arg | Arg | Ile | His | Tyr |
|  |  | 990 |  |  |  | 995 |  |  |  |  | 1000 |  |  |  |  |

```
tct cag aat gac ttg gtt gag tac tca cca gtc aca gaa aag cat      6066
Ser Gln Asn Asp Leu Val Glu Tyr Ser Pro Val Thr Glu Lys His
    1005                1010                1015 ctt acg gat ggc atg aca gta aga gaa tta tgc agt gct gcc ata      6111
Leu Thr Asp Gly Met Thr Val Arg Glu Leu Cys Ser Ala Ala Ile
1020                1025                1030 acc atg agt gat aac act gcg gcc aac tta ctt ctg aca acg atc      6156
Thr Met Ser Asp Asn Thr Ala Ala Asn Leu Leu Leu Thr Thr Ile
    1035                1040                1045 gga gga ccg aag gag cta acc gct ttt ttg cac aac atg ggg gat      6201
Gly Gly Pro Lys Glu Leu Thr Ala Phe Leu His Asn Met Gly Asp
1050                1055                1060 cat gta act cgc ctt gat cgt tgg gaa ccg gag ctg aat gaa gcc      6246
His Val Thr Arg Leu Asp Arg Trp Glu Pro Glu Leu Asn Glu Ala
    1065                1070                1075 ata cca aac gac gag cgt gac acc acg atg cct gta gca atg gca      6291
Ile Pro Asn Asp Glu Arg Asp Thr Thr Met Pro Val Ala Met Ala
1080                1085                1090 aca acg ttg cgc aaa cta tta act ggc gaa cta ctt act cta gct      6336
Thr Thr Leu Arg Lys Leu Leu Thr Gly Glu Leu Leu Thr Leu Ala
    1095                1100                1105 tcc cgg caa caa tta ata gac tgg atg gag gcg gat aaa gtt gca      6381
Ser Arg Gln Gln Leu Ile Asp Trp Met Glu Ala Asp Lys Val Ala
1110                1115                1120 gga cca ctt ctg cgc tcg gcc ctt ccg gct ggc tgg ttt att gct      6426
Gly Pro Leu Leu Arg Ser Ala Leu Pro Ala Gly Trp Phe Ile Ala
    1125                1130                1135 gat aaa tct gga gcc ggt gag cgt ggg tct cgc ggt atc att gca      6471
Asp Lys Ser Gly Ala Gly Glu Arg Gly Ser Arg Gly Ile Ile Ala
1140                1145                1150 gca ctg ggg cca gat ggt aag ccc tcc cgt atc gta gtt atc tac      6516
Ala Leu Gly Pro Asp Gly Lys Pro Ser Arg Ile Val Val Ile Tyr
    1155                1160                1165 acg acg ggg agt cag gca act atg gat gaa cga aat aga cag atc      6561
Thr Thr Gly Ser Gln Ala Thr Met Asp Glu Arg Asn Arg Gln Ile
1170                1175                1180 gct gag ata ggt gcc tca ctg att aag cat tgg taactgtcag           6604
Ala Glu Ile Gly Ala Ser Leu Ile Lys His Trp
    1185                1190 accaagttta ctcatatata ctttagattg atttaaaact tcattttaa tttaaaagga   6664 tctaggtgaa gatccttttt gataatctca tgaccaaaat cccttaacgt gagttttcgt   6724
tccactgagc gtcagacccc gtagaaaaga tcaaggatc ttcttgagat cctttttttc    6784
tgcgcgtaat ctgctgcttg caaacaaaaa aaccaccgct accagcggtg tttgtttgc    6844 cggatcaaga gctaccaact ctttttccga aggtaactgg cttcagcaga gcgcagatac   6904
caaatactgt tcttctagtg tagccgtagt taggccacca cttcaagaac tctgtagcac   6964
cgcctacata cctcgctctg ctaatcctgt taccagtggc tgctgccagt ggcgataagt   7024
cgtgtcttac cgggttggac tcaagacgat agttaccgga taaggcgcag cggtcgggct   7084 gaacggggggg ttcgtgcaca cagcccagct tggagcgaac gacctacacc gaactgagat   7144
acctacagcg tgagctatga gaaagcgcca cgcttcccga agggagaaag gcggacaggt   7204
atccggtaag cggcagggtc ggaacaggag agcgcacgag ggagcttcca ggggggaaacg   7264 cctggtatct ttatagtcct gtcgggtttc gccacctctg acttgagcgt cgatttttgt   7324
```

```
gatgctcgtc aggggggcgg agcctatgga aaaacgccag caacgcggcc tttttacggt    7384
tcctggcctt ttgctggcct tttgctcaca tgttctttcc tgcgttatcc cctgattctg    7444
tggataaccg tattaccgcc tttgagtgag ctgataccgc tcgccgcagc cgaacgaccg    7504
agcgcagcga gtcagtgagc gaggaagcgg aagagcgccc aatacgcaaa ccgcctctcc    7564
ccgcgcgttg gccgattcat taatgcagct ggcacgacag gtttcccgac tggaaagcgg    7624
gcagtgagcg caacgcaatt aatgtgagtt agctcactca ttaggcaccc caggctttac    7684
actttatgct tccggctcgt atgttgtgtg gaattgtgag cggataacaa tttcacacag    7744
gaaacagcta tgaccatgat tacgccagat ttaattaa    7782
```

<210> SEQ ID NO 44
<211> LENGTH: 120
<212> TYPE: PRT
<213> ORGANISM: Artificial sequence
<220> FEATURE:
<223> OTHER INFORMATION: Synthetic Construct

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ser Asn Tyr
            20                  25                  30

Tyr Trp Ser Trp Ile Arg Gln Ser Pro Gly Lys Gly Leu Glu Trp Ile
        35                  40                  45

Gly Phe Ile Tyr Tyr Gly Gly Asn Thr Lys Tyr Asn Pro Ser Leu Lys
    50                  55                  60

Ser Arg Val Thr Ile Ser Gln Asp Thr Ser Lys Ser Gln Val Ser Leu
65                  70                  75                  80

Thr Met Ser Ser Val Thr Ala Ala Glu Ser Ala Val Tyr Phe Cys Ala
                85                  90                  95

Arg Ala Ser Cys Ser Gly Gly Tyr Cys Ile Leu Asp Tyr Trp Gly Gln
            100                 105                 110

Gly Thr Leu Val Thr Val Ser Ser
        115                 120

<210> SEQ ID NO 45
<211> LENGTH: 98
<212> TYPE: PRT
<213> ORGANISM: Artificial sequence
<220> FEATURE:
<223> OTHER INFORMATION: Synthetic Construct

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

```
<210> SEQ ID NO 46
<211> LENGTH: 231
<212> TYPE: PRT
<213> ORGANISM: Artificial sequence
<220> FEATURE:
<223> OTHER INFORMATION: Synthetic Construct

<400> SEQUENCE: 46

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly
225                 230

<210> SEQ ID NO 47
<211> LENGTH: 129
<212> TYPE: PRT
<213> ORGANISM: Artificial sequence
<220> FEATURE:
<223> OTHER INFORMATION: Synthetic Construct

<400> SEQUENCE: 47

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 48
<211> LENGTH: 107
<212> TYPE: PRT
<213> ORGANISM: Artificial sequence
<220> FEATURE:
<223> OTHER INFORMATION: Synthetic Construct

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

<210> SEQ ID NO 49
<211> LENGTH: 223
<212> TYPE: PRT
<213> ORGANISM: Artificial sequence
<220> FEATURE:
<223> OTHER INFORMATION: Synthetic Construct

<400> SEQUENCE: 49

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Glu Pro Asp
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140
```

```
Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 50
<211> LENGTH: 286
<212> TYPE: PRT
<213> ORGANISM: Artificial sequence
<220> FEATURE:
<223> OTHER INFORMATION: Synthetic Construct

<400> SEQUENCE: 50

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
                100                 105                 110

Asp Gly Met Thr Val Arg Glu Leu Cys Ser Ala Ala Ile Thr Met Ser
            115                 120                 125

Asp Asn Thr Ala Ala Asn Leu Leu Leu Thr Thr Ile Gly Gly Pro Lys
        130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```